(12) United States Patent
Senff et al.

(10) Patent No.: US 12,186,147 B2
(45) Date of Patent: *Jan. 7, 2025

(54) REDUCED FORM FACTOR ORAL IRRIGATOR

(71) Applicant: WATER PIK, INC., Fort Collins, CO (US)

(72) Inventors: Oscar Senff, Broomfield, CO (US); Robert Wagner, Firestone, CO (US)

(73) Assignee: WATER PIK, INC., Fort Collins, CO (US)

( * ) Notice: Subject to any disclaimer, the term of this patent is extended or adjusted under 35 U.S.C. 154(b) by 95 days.

This patent is subject to a terminal disclaimer.

(21) Appl. No.: 17/536,574

(22) Filed: Nov. 29, 2021

(65) Prior Publication Data

US 2022/0079728 A1    Mar. 17, 2022

Related U.S. Application Data

(62) Division of application No. 15/415,750, filed on Jan. 25, 2017, now Pat. No. 11,213,376.
(Continued)

(51) Int. Cl.
*A61C 17/02* (2006.01)
*A61C 1/00* (2006.01)
(Continued)

(52) U.S. Cl.
CPC ........ *A61C 17/0202* (2013.01); *A61C 1/0092* (2013.01); *A61C 17/024* (2019.05);
(Continued)

(58) Field of Classification Search
CPC .................. A61C 1/0092; A61C 17/02; A61C 17/0212; A61C 17/0214; A61C 17/0202;
(Continued)

(56) References Cited

U.S. PATENT DOCUMENTS

| 555,588 A | 3/1896 | Spencer |
| 1,278,225 A | 9/1918 | Schamberg |

(Continued)

FOREIGN PATENT DOCUMENTS

| CA | 851479 | 9/1970 |
| CA | 3046973 A1 | 6/2018 |

(Continued)

OTHER PUBLICATIONS

US RE27,274 E, 01/1972, Mattingly (withdrawn)
(Continued)

*Primary Examiner* — Justine R Yu
*Assistant Examiner* — Matthew R Moon

(57) ABSTRACT

An oral irrigator has a base unit housing a motor and a pump, a removable reservoir defining a reservoir cavity configured to mechanically couple to a top surface of the base unit and fluidly couple the reservoir cavity to the pump, and a belt drive assembly connecting the motor to the pump. The belt drive assembly includes a drive pulley connected to an output shaft of the motor, a driven pulley spaced apart from the drive pulley and mechanically connected to a piston that drives the pump, and a continuous belt connecting the drive pulley to the driven pulley. A handle for the oral irrigator may include a housing defining a slot formed in an outer wall of the housing.

16 Claims, 46 Drawing Sheets

Related U.S. Application Data

(60) Provisional application No. 62/416,926, filed on Nov. 3, 2016, provisional application No. 62/286,925, filed on Jan. 25, 2016.

(51) Int. Cl.
*A61C 17/024* (2006.01)
*A61H 13/00* (2006.01)
*A61M 3/02* (2006.01)
*A61M 39/26* (2006.01)
*A61C 17/22* (2006.01)
*A61M 39/24* (2006.01)

(52) U.S. Cl.
CPC ......... *A61H 13/005* (2013.01); *A61M 3/0258* (2013.01); *A61M 39/26* (2013.01); *A61C 17/225* (2013.01); *A61H 2201/1246* (2013.01); *A61M 2039/242* (2013.01); *A61M 2205/0272* (2013.01)

(58) Field of Classification Search
CPC ..... A61C 17/225; A61C 17/16; A61C 1/0061; A61C 1/0084; A61C 17/0211; A61C 17/028; A61C 17/36; A61M 39/26; A61M 3/0258; A61M 2205/0272; A61M 2039/242; A61M 2210/0625; A61H 13/005; A61H 2201/1246; F16L 37/40
See application file for complete search history.

(56) References Cited

U.S. PATENT DOCUMENTS

| | | |
|---|---|---|
| 1,452,258 A | 4/1923 | Smith |
| 1,464,419 A | 8/1923 | Gill |
| 1,480,310 A | 1/1924 | Smith |
| 1,498,267 A | 6/1924 | Man |
| 1,602,742 A | 10/1926 | Bennet |
| 1,650,686 A | 11/1927 | Binks |
| 1,669,889 A | 5/1928 | Andrews et al. |
| 1,681,320 A | 8/1928 | Bergl et al. |
| 1,933,454 A | 10/1933 | Sidney |
| 1,940,111 A | 12/1933 | Austin |
| D93,019 S | 8/1934 | Hose |
| 1,977,782 A | 10/1934 | Roy |
| 2,107,686 A | 2/1938 | Bramsen et al. |
| 2,124,747 A | 7/1938 | Pieper |
| 2,171,292 A | 8/1939 | Pieper |
| D159,872 S | 8/1950 | Skold |
| 2,531,730 A | 11/1950 | Henderson |
| 2,595,666 A | 5/1952 | Hutson |
| 2,669,233 A | 2/1954 | Friend |
| 2,709,227 A | 5/1955 | Foley et al. |
| 2,733,713 A | 2/1956 | Kabnick |
| 2,783,919 A | 3/1957 | Ansell |
| 2,794,437 A | 6/1957 | Tash |
| 2,870,932 A | 1/1959 | Davis |
| 2,984,452 A | 5/1961 | Hooper |
| 3,089,490 A | 5/1963 | Goldberg |
| 3,096,913 A | 7/1963 | Jousson |
| 3,144,867 A | 8/1964 | Trupp et al. |
| D202,041 S | 8/1965 | Burzlaff |
| 3,209,956 A | 10/1965 | McKenzie |
| 3,216,619 A | 11/1965 | Richards et al. |
| 3,225,759 A | 12/1965 | Drapen et al. |
| 3,227,158 A | 1/1966 | Mattingly |
| 3,266,623 A | 8/1966 | Poferl |
| 3,297,558 A | 1/1967 | Hillquist |
| D208,778 S | 10/1967 | Koch |
| D209,202 S | 11/1967 | Fulton et al. |
| D209,203 S | 11/1967 | Mattingly et al. |
| D209,204 S | 11/1967 | St. Clair et al. |
| D209,395 S | 11/1967 | Gilbert |
| 3,357,599 A | 12/1967 | Douglas ................ A45D 19/02 222/144.5 |
| D210,018 S | 1/1968 | Mattingly et al. |
| D210,019 S | 1/1968 | Johnson et al. |
| 3,370,214 A | 2/1968 | Aymar |
| 3,391,696 A | 7/1968 | Woodward |
| 3,393,673 A | 7/1968 | Mattingly et al. |
| 3,393,676 A | 7/1968 | Kummer et al. |
| 3,400,999 A | 9/1968 | Goldstein |
| 3,418,552 A | 12/1968 | Holmes |
| 3,420,228 A | 1/1969 | Kalbfeld |
| 3,425,410 A | 2/1969 | Cammack |
| 3,453,969 A | 7/1969 | Mattingly |
| 3,465,751 A | 9/1969 | Powers |
| 3,467,083 A | 9/1969 | Mattingly |
| 3,467,286 A | 9/1969 | Ostrowsky |
| D215,920 S | 11/1969 | McCarty et al. |
| 3,487,828 A | 1/1970 | Troy |
| 3,489,268 A | 1/1970 | Meierhoefer |
| 3,495,587 A | 2/1970 | Freedman |
| 3,496,933 A | 2/1970 | Lloyd |
| 3,499,440 A | 3/1970 | Gibbs |
| 3,500,824 A | 3/1970 | Gilbert |
| 3,501,203 A | 3/1970 | Falk |
| 3,502,072 A | 3/1970 | Stillman |
| 3,517,669 A | 6/1970 | Buono et al. |
| D218,270 S | 8/1970 | Soper |
| 3,522,801 A | 8/1970 | Robinson |
| 3,532,221 A | 10/1970 | Kaluhiokalani et al. |
| 3,536,065 A | 10/1970 | Moret |
| 3,537,444 A | 11/1970 | Garn |
| 3,538,950 A | 11/1970 | Porteners |
| 3,547,110 A | 12/1970 | Balamuth |
| 3,561,433 A | 2/1971 | Kovach |
| D220,334 S | 3/1971 | Mackay et al. |
| 3,570,525 A | 3/1971 | Borsum |
| 3,572,375 A | 3/1971 | Rosenberg |
| 3,578,884 A | 5/1971 | Jacobson |
| D220,996 S | 6/1971 | Irons |
| 3,583,609 A | 6/1971 | Oppenheimer |
| 3,590,813 A | 7/1971 | Roszyk |
| 3,608,548 A | 9/1971 | Lewis |
| D222,862 S | 1/1972 | Cook |
| 3,636,947 A | 1/1972 | Balamuth |
| 3,651,576 A | 3/1972 | Massa |
| 3,669,101 A | 6/1972 | Kleiner |
| 3,703,170 A | 11/1972 | Ryckman, Jr. |
| 3,718,974 A | 3/1973 | Buchtel et al. |
| 3,747,595 A | 7/1973 | Grossan |
| 3,768,472 A | 10/1973 | Hodosh et al. |
| 3,771,186 A | 11/1973 | Moret et al. |
| 3,783,364 A | 1/1974 | Gallanis et al. |
| 3,809,506 A | 5/1974 | Malcosky |
| 3,809,977 A | 5/1974 | Balamuth et al. |
| 3,811,432 A | 5/1974 | Moret |
| 3,820,532 A | 6/1974 | Eberhardt et al. |
| 3,827,147 A | 8/1974 | Condon |
| 3,837,166 A | 9/1974 | Hiraoka |
| 3,840,795 A | 10/1974 | Roszyk et al. |
| 3,847,145 A | 11/1974 | Grossan |
| 3,851,643 A | 12/1974 | Musy |
| 3,854,209 A | 12/1974 | Franklin et al. |
| 3,863,628 A | 2/1975 | Vit |
| 3,871,560 A | 3/1975 | Crippa |
| 3,874,506 A | 4/1975 | Hill et al. |
| 3,911,796 A | 10/1975 | Hull et al. |
| 3,912,125 A | 10/1975 | Acklin |
| 3,921,297 A | 11/1975 | Vit |
| 3,943,628 A | 3/1976 | Kronman et al. |
| 3,959,883 A | 6/1976 | Walls et al. |
| 3,973,558 A | 8/1976 | Stouffer et al. |
| 3,977,084 A | 8/1976 | Sloan |
| 4,001,526 A | 1/1977 | Olson |
| 4,004,302 A | 1/1977 | Hori |
| 4,007,739 A | 2/1977 | Bron et al. |
| 4,013,227 A | 3/1977 | Herrera |
| 4,015,336 A | 4/1977 | Johnson |
| 4,022,114 A | 5/1977 | Hansen, III |
| 4,052,002 A | 10/1977 | Stouffer et al. |
| D246,667 S | 12/1977 | Mackay et al. |
| 4,060,870 A | 12/1977 | Cannarella |

(56) References Cited

U.S. PATENT DOCUMENTS

| | | |
|---|---|---|
| 4,075,761 A | 2/1978 | Behne et al. |
| 4,078,558 A | 3/1978 | Woog et al. |
| 4,094,311 A | 6/1978 | Hudson |
| 4,108,167 A | 8/1978 | Hickman et al. |
| 4,108,178 A | 8/1978 | Betush |
| 4,109,650 A | 8/1978 | Peclard |
| 4,122,845 A | 10/1978 | Stouffer et al. |
| 4,133,971 A | 1/1979 | Boyd et al. |
| 4,135,501 A | 1/1979 | Leunissan |
| 4,141,352 A | 2/1979 | Ebner et al. |
| 4,144,646 A | 3/1979 | Takemoto et al. |
| 4,149,315 A | 4/1979 | Page, Jr. et al. |
| 4,154,375 A | 5/1979 | Bippus |
| 4,160,383 A | 7/1979 | Rauschenberger |
| 4,171,572 A | 10/1979 | Nash |
| 4,182,038 A | 1/1980 | Fleer |
| 4,200,235 A | 4/1980 | Monschke |
| 4,201,200 A | 5/1980 | Hubner |
| 4,210,380 A | 7/1980 | Brzostek |
| 4,215,476 A | 8/1980 | Armstrong |
| 4,219,618 A | 8/1980 | Leonard |
| 4,227,878 A | 10/1980 | Lohn |
| 4,229,634 A | 10/1980 | Hickman et al. |
| 4,236,889 A | 12/1980 | Wright |
| D258,097 S | 2/1981 | Wistrand |
| 4,248,589 A | 2/1981 | Lewis |
| 4,249,899 A | 2/1981 | Davis |
| 4,257,458 A | 3/1981 | Kondo et al. |
| 4,262,799 A | 4/1981 | Perrett |
| 4,266,934 A | 5/1981 | Pernot |
| 4,276,023 A | 6/1981 | Phillips et al. |
| 4,276,880 A | 7/1981 | Malmin |
| 4,302,186 A | 11/1981 | Cammack et al. |
| 4,303,064 A | 12/1981 | Buffa |
| 4,303,070 A | 12/1981 | Ichikawa et al. |
| 4,306,862 A | 12/1981 | Knox |
| 4,315,741 A | 2/1982 | Reichl |
| 4,319,568 A | 3/1982 | Tregoning |
| 4,331,422 A | 5/1982 | Heyman |
| 4,337,040 A | 6/1982 | Cammack et al. |
| 4,340,365 A | 7/1982 | Pisanu |
| 4,340,368 A | 7/1982 | Lococo |
| D266,117 S | 9/1982 | Oberheim |
| 4,353,694 A | 10/1982 | Pelerin |
| 4,363,626 A | 12/1982 | Schmidt et al. |
| 4,365,376 A | 12/1982 | Oda et al. |
| 4,370,131 A | 1/1983 | Banko |
| 4,374,354 A | 2/1983 | Petrovic et al. |
| 4,382,167 A | 5/1983 | Maruyama et al. |
| 4,382,786 A | 5/1983 | Lohn |
| D270,000 S | 8/1983 | Ketler |
| 4,396,011 A | 8/1983 | Mack et al. |
| 4,412,823 A | 11/1983 | Sakai et al. |
| 4,416,628 A | 11/1983 | Cammack |
| 4,442,830 A | 4/1984 | Markau |
| 4,442,831 A | 4/1984 | Trenary |
| 4,452,238 A | 6/1984 | Kerr |
| 4,454,866 A | 6/1984 | Fayen |
| 4,512,769 A | 4/1985 | Kozam et al. |
| 4,517,962 A | 5/1985 | Heckele |
| 4,531,912 A | 7/1985 | Schuss et al. |
| 4,531,913 A | 7/1985 | Taguchi |
| 4,534,340 A | 8/1985 | Kerr et al. |
| 4,552,130 A | 11/1985 | Kinoshita |
| 4,561,214 A | 12/1985 | Inoue |
| D283,374 S | 4/1986 | Cheuk-Yiu |
| 4,585,415 A | 4/1986 | Hommann |
| 4,591,777 A | 5/1986 | McCarty et al. |
| 4,592,728 A | 6/1986 | Davis |
| 4,602,906 A | 7/1986 | Grunenfelder |
| 4,607,627 A | 8/1986 | Leber et al. |
| 4,613,074 A | 9/1986 | Schulze |
| 4,619,009 A | 10/1986 | Rosenstatter |
| 4,619,612 A | 10/1986 | Weber et al. |
| 4,629,425 A | 12/1986 | Detsch |
| 4,636,198 A | 1/1987 | Stade |
| 4,642,037 A | 2/1987 | Fritchman |
| 4,644,937 A | 2/1987 | Hommann |
| 4,645,488 A | 2/1987 | Matukas |
| 4,647,831 A | 3/1987 | O'Malley et al. |
| 4,648,838 A | 3/1987 | Schlachter |
| 4,650,475 A | 3/1987 | Smith et al. |
| 4,655,198 A | 4/1987 | Hommann |
| 4,669,453 A | 6/1987 | Atkinson et al. |
| 4,672,953 A | 6/1987 | DiVito |
| 4,673,396 A | 6/1987 | Urbaniak |
| D291,354 S | 8/1987 | Camens |
| 4,716,352 A | 12/1987 | Hurn et al. |
| 4,749,340 A | 6/1988 | Ikeda et al. |
| 4,770,632 A | 9/1988 | Ryder et al. |
| D298,565 S | 11/1988 | Kohler, Jr. et al. |
| 4,783,321 A | 11/1988 | Spence |
| 4,787,845 A | 11/1988 | Valentine |
| 4,787,847 A | 11/1988 | Martin et al. |
| 4,798,292 A | 1/1989 | Hauze |
| 4,803,974 A | 2/1989 | Powell |
| 4,804,364 A | 2/1989 | Dieras et al. |
| 4,810,148 A | 3/1989 | Aisa et al. |
| 4,818,229 A | 4/1989 | Vasile |
| 4,820,152 A | 4/1989 | Warrin et al. |
| 4,821,923 A | 4/1989 | Skorka |
| 4,824,368 A | 4/1989 | Hickman |
| 4,826,431 A | 5/1989 | Fujimura et al. |
| 4,827,551 A | 5/1989 | Maser et al. |
| 4,832,683 A | 5/1989 | Idemoto et al. |
| 4,854,869 A | 8/1989 | Lawhorn |
| 4,861,340 A | 8/1989 | Smith et al. |
| 4,862,876 A | 9/1989 | Lih-Sheng |
| 4,864,918 A | 9/1989 | Martin |
| 4,869,720 A | 9/1989 | Chernack |
| 4,880,382 A | 11/1989 | Moret et al. |
| 4,886,452 A | 12/1989 | Lohn |
| 4,900,252 A | 2/1990 | Liefke et al. |
| 4,902,225 A | 2/1990 | Lohn |
| 4,903,687 A | 2/1990 | Lih-Sheng |
| 4,906,187 A | 3/1990 | Amadera |
| 4,907,744 A | 3/1990 | Jousson |
| 4,915,304 A | 4/1990 | Campani |
| 4,925,450 A | 5/1990 | Imonti et al. |
| 4,928,675 A | 5/1990 | Thornton |
| 4,930,660 A | 6/1990 | Porteous |
| 4,941,459 A | 7/1990 | Mathur |
| 4,950,159 A | 8/1990 | Hansen |
| 4,958,629 A | 9/1990 | Peace et al. |
| 4,958,751 A | 9/1990 | Curtis et al. |
| 4,959,199 A | 9/1990 | Brewer |
| 4,961,698 A | 10/1990 | Vlock |
| 4,966,551 A | 10/1990 | Betush |
| 4,969,874 A | 11/1990 | Michel et al. |
| 4,973,246 A | 11/1990 | Black |
| 4,973,247 A | 11/1990 | Varnes et al. |
| 4,973,250 A | 11/1990 | Milman |
| 4,975,054 A | 12/1990 | Esrock |
| 4,979,503 A | 12/1990 | Chernack |
| 4,979,504 A | 12/1990 | Mills |
| 4,989,590 A | 2/1991 | Baum et al. |
| 4,998,880 A | 3/1991 | Nerli |
| 5,013,241 A | 5/1991 | Von Gutfeld et al. |
| 5,013,300 A | 5/1991 | Williams |
| 5,014,884 A | 5/1991 | Wunsch |
| 5,019,054 A | 5/1991 | Clement et al. |
| 5,027,798 A | 7/1991 | Primiano |
| 5,029,576 A | 7/1991 | Evans, Sr. |
| 5,033,617 A | 7/1991 | Hartwein et al. |
| 5,033,961 A | 7/1991 | Kandler et al. |
| D318,918 S | 8/1991 | Hartwein |
| 5,046,486 A | 9/1991 | Grulke et al. |
| 5,049,071 A | 9/1991 | Davis et al. |
| 5,060,825 A | 10/1991 | Palmer et al. |
| 5,061,180 A | 10/1991 | Wiele |
| 5,062,795 A | 11/1991 | Woog |
| 5,064,168 A | 11/1991 | Raines et al. |
| D322,314 S | 12/1991 | Ohbayashi |
| 5,071,346 A | 12/1991 | Domaas |

(56) References Cited

U.S. PATENT DOCUMENTS

| | | | |
|---|---|---|---|
| 5,082,115 A | 1/1992 | Hutcheson | |
| 5,082,443 A | 1/1992 | Lohn | |
| 5,085,317 A | 2/1992 | Jensen et al. | |
| 5,086,756 A | 2/1992 | Powell | |
| 5,086,788 A | 2/1992 | Bally et al. | |
| 5,095,893 A | 3/1992 | Rawden, Jr. | |
| 5,098,291 A | 3/1992 | Curtis et al. | |
| 5,098,676 A | 3/1992 | Brooks, Jr. | |
| 5,100,319 A | 3/1992 | Baum | |
| 5,117,871 A | 6/1992 | Gardner et al. | |
| 5,125,835 A | 6/1992 | Young | |
| 5,127,831 A | 7/1992 | Bab | |
| 5,142,723 A | 9/1992 | Lustig et al. | |
| 5,150,841 A | 9/1992 | Silvenis et al. | |
| 5,172,810 A | 12/1992 | Brewer | |
| 5,173,273 A | 12/1992 | Brewer | |
| 5,183,035 A | 2/1993 | Weir | |
| 5,197,458 A | 3/1993 | Ito et al. | |
| 5,197,460 A | 3/1993 | Ito et al. | |
| 5,199,871 A | 4/1993 | Young | |
| 5,203,697 A | 4/1993 | Malmin | |
| 5,203,769 A | 4/1993 | Clement et al. | |
| 5,204,004 A | 4/1993 | Johnston et al. | |
| 5,208,933 A | 5/1993 | Lustig et al. | |
| 5,215,193 A | 6/1993 | Dennis | |
| 5,218,956 A | 6/1993 | Handler et al. | |
| 5,220,914 A | 6/1993 | Thompson | |
| 5,228,646 A | 7/1993 | Raines | |
| 5,230,624 A | 7/1993 | Wolf et al. | |
| 5,232,687 A | 8/1993 | Geimer | |
| 5,235,968 A | 8/1993 | Woog | |
| 5,241,714 A | 9/1993 | Barry | |
| 5,246,367 A | 9/1993 | Ito et al. | |
| 5,252,064 A | 10/1993 | Baum et al. | |
| D341,200 S | 11/1993 | Yoshimoto | |
| 5,257,933 A | 11/1993 | Jousson | |
| 5,261,448 A | 11/1993 | Furuya et al. | |
| D341,943 S | 12/1993 | Si-Hoe | |
| 5,267,586 A | 12/1993 | Jankavaara | |
| 5,269,684 A | 12/1993 | Fischer | |
| 5,281,137 A | 1/1994 | Jousson | |
| 5,281,139 A | 1/1994 | Frank et al. | |
| 5,282,745 A | 2/1994 | Wiltrout et al. | |
| 5,286,192 A | 2/1994 | Dixon | |
| 5,286,201 A | 2/1994 | Yu | |
| 5,295,832 A | 3/1994 | Evans | |
| 5,297,962 A | 3/1994 | O'Connor et al. | |
| D346,212 S | 4/1994 | Hosl | |
| 5,301,381 A | 4/1994 | Klupt | |
| 5,302,123 A | 4/1994 | Bechard | |
| 5,317,691 A | 5/1994 | Traeger | |
| 5,321,865 A | 6/1994 | Kaeser | |
| 5,323,770 A | 6/1994 | Ito et al. | |
| 5,331,704 A | 7/1994 | Rosen et al. | |
| 5,344,317 A | 9/1994 | Pacher et al. | |
| 5,346,677 A | 9/1994 | Risk | |
| 5,349,896 A | 9/1994 | Delaney | |
| D351,892 S | 10/1994 | Wolf et al. | |
| 5,360,338 A | 11/1994 | Waggoner | |
| 5,368,548 A | 11/1994 | Jousson | |
| 5,370,534 A | 12/1994 | Wolf et al. | |
| D354,168 S | 1/1995 | Hartwein | |
| D354,559 S | 1/1995 | Knute | |
| 5,378,149 A | 1/1995 | Stropko | |
| 5,380,201 A | 1/1995 | Kawata | |
| D356,864 S | 3/1995 | Woog | |
| 5,399,089 A | 3/1995 | Eichman et al. | |
| D358,883 S | 5/1995 | Vos | |
| 5,456,672 A | 10/1995 | Diederich et al. | |
| 5,465,445 A | 11/1995 | Yeh | |
| 5,467,495 A | 11/1995 | Boland et al. | |
| 5,468,148 A | 11/1995 | Ricks | |
| 5,470,305 A | 11/1995 | Arnett et al. | |
| 5,474,450 A | 12/1995 | Chronister | |
| 5,474,451 A | 12/1995 | Dalrymple et al. | |
| 5,476,379 A | 12/1995 | Disel | |
| 5,484,281 A | 1/1996 | Renow et al. | |
| 5,487,877 A | 1/1996 | Choi | |
| 5,490,779 A | 2/1996 | Malmin | |
| 5,505,916 A | 4/1996 | Berry, Jr. | |
| D369,656 S | 5/1996 | Vos | |
| D370,125 S | 5/1996 | Craft et al. | |
| 5,525,058 A | 6/1996 | Gallant et al. | |
| 5,526,841 A | 6/1996 | Detsch et al. | |
| 5,540,587 A | 7/1996 | Malmin | |
| 5,547,374 A | 8/1996 | Coleman | |
| D373,631 S | 9/1996 | Maeda et al. | |
| 5,554,014 A | 9/1996 | Becker | |
| 5,554,025 A | 9/1996 | Kinsel | |
| 5,556,001 A | 9/1996 | Weissman et al. | |
| 5,564,629 A | 10/1996 | Weissman et al. | |
| D376,893 S | 12/1996 | Gornet | |
| D377,091 S | 12/1996 | Scott, Sr. | |
| 5,613,259 A | 3/1997 | Craft et al. | |
| 5,616,028 A | 4/1997 | Hatele et al. | |
| 5,626,472 A | 5/1997 | Pennetta | |
| 5,634,791 A | 6/1997 | Matsuura et al. | |
| 5,636,904 A | 6/1997 | Bell | A46B 3/02 300/20 |
| 5,636,987 A | 6/1997 | Serfaty | |
| 5,640,735 A | 6/1997 | Manning | |
| D382,407 S | 8/1997 | Craft et al. | |
| 5,653,591 A | 8/1997 | Loge | |
| 5,659,995 A | 8/1997 | Hoffman | |
| 5,667,483 A | 9/1997 | Santos | |
| D386,576 S | 11/1997 | Wang et al. | |
| 5,683,192 A | 11/1997 | Kilfoil | |
| 5,685,829 A | 11/1997 | Allen | |
| 5,685,851 A | 11/1997 | Murphy et al. | |
| 5,697,784 A | 12/1997 | Hatele et al. | |
| D388,612 S | 1/1998 | Stutzer et al. | |
| D388,613 S | 1/1998 | Stutzer et al. | |
| D389,091 S | 1/1998 | Dickinson | |
| 5,709,545 A | 1/1998 | Johnston et al. | |
| D390,934 S | 2/1998 | McKeone | |
| 5,716,007 A | 2/1998 | Nottingham et al. | |
| 5,718,668 A | 2/1998 | Arnett et al. | |
| 5,746,595 A | 5/1998 | Ford | |
| 5,749,726 A | 5/1998 | Kinsel | |
| 5,759,502 A | 6/1998 | Spencer et al. | |
| 5,779,471 A | 7/1998 | Tseng et al. | |
| 5,779,654 A | 7/1998 | Foley et al. | |
| 5,788,289 A | 8/1998 | Cronley | F16L 37/105 137/533.17 |
| 5,795,153 A | 8/1998 | Rechmann | |
| 5,796,325 A | 8/1998 | Lundell et al. | |
| 5,833,065 A | 11/1998 | Burgess | |
| 5,836,030 A | 11/1998 | Hazeu et al. | |
| D402,744 S | 12/1998 | Zuege | |
| 5,851,079 A | 12/1998 | Horstman et al. | |
| D403,511 S | 1/1999 | Serbinski | |
| D406,334 S | 3/1999 | Rosenthal et al. | |
| 5,876,201 A | 3/1999 | Wilson et al. | |
| D408,511 S | 4/1999 | Allen et al. | |
| 5,901,397 A | 5/1999 | Häfele et al. | |
| 5,933,918 A | 8/1999 | Wallays | B25G 3/18 16/114.1 |
| 5,934,902 A | 8/1999 | Abahusayn | |
| D413,975 S | 9/1999 | Maeda | |
| D416,999 S | 11/1999 | Miyamoto | |
| D417,082 S | 11/1999 | Classen et al. | |
| 5,993,402 A | 11/1999 | Sauer et al. | |
| 6,030,215 A | 2/2000 | Ellion et al. | |
| 6,038,960 A | 3/2000 | Fukushima et al. | |
| 6,039,180 A | 3/2000 | Grant | |
| 6,047,429 A | 4/2000 | Wu | |
| D424,181 S | 5/2000 | Caplow | |
| D425,615 S | 5/2000 | Bachman et al. | |
| D425,981 S | 5/2000 | Bachman et al. | |
| 6,056,548 A | 5/2000 | Neuberger et al. | |
| 6,056,710 A | 5/2000 | Bachman et al. | |
| D426,633 S | 6/2000 | Bachman et al. | |
| 6,089,865 A | 7/2000 | Edgar | |
| 6,116,866 A | 9/2000 | Tomita et al. | |

(56) References Cited

U.S. PATENT DOCUMENTS

| | | |
|---|---|---|
| 6,120,755 A | 9/2000 | Jacobs |
| 6,124,699 A | 9/2000 | Suzuki et al. |
| D434,500 S | 11/2000 | Pollock et al. |
| 6,159,006 A * | 12/2000 | Cook .................... A61C 17/02 601/165 |
| 6,164,967 A | 12/2000 | Sale et al. |
| D435,905 S | 1/2001 | Bachman et al. |
| D437,049 S | 1/2001 | Hartwein |
| 6,193,512 B1 | 2/2001 | Wallace |
| 6,193,932 B1 | 2/2001 | Wu et al. |
| 6,199,239 B1 | 3/2001 | Dickerson |
| 6,200,134 B1 | 3/2001 | Kovac |
| D439,781 S | 4/2001 | Spore |
| 6,217,835 B1 | 4/2001 | Riley et al. |
| D441,861 S | 5/2001 | Hatliger |
| 6,233,773 B1 | 5/2001 | Karge et al. |
| 6,234,205 B1 | 5/2001 | D'Amelio et al. |
| 6,237,178 B1 | 5/2001 | Krammer et al. |
| 6,238,211 B1 | 5/2001 | Esrock ............... A61C 17/0202 433/80 |
| 6,247,929 B1 | 6/2001 | Bachman et al. |
| 6,280,190 B1 | 8/2001 | Hoffman |
| D448,236 S | 9/2001 | Murray |
| 6,293,792 B1 | 9/2001 | Hanson |
| D449,884 S | 10/2001 | Tobin et al. |
| 6,299,419 B1 | 10/2001 | Hunklinger |
| D453,453 S | 2/2002 | Lun |
| D455,201 S | 4/2002 | Jones |
| D455,203 S | 4/2002 | Jones |
| 6,363,565 B1 | 4/2002 | Paffrath |
| D457,949 S | 5/2002 | Krug |
| D464,799 S | 10/2002 | Crossman et al. |
| 6,468,482 B1 | 10/2002 | Frieze et al. |
| 6,475,173 B1 | 11/2002 | Bachman et al. |
| 6,485,451 B1 | 11/2002 | Roberts et al. |
| 6,497,375 B1 | 12/2002 | Srinath et al. |
| 6,497,572 B2 | 12/2002 | Hood et al. |
| 6,502,584 B1 | 1/2003 | Fordham |
| D470,660 S | 2/2003 | Schaber |
| 6,532,837 B1 | 3/2003 | Magussen, Jr. |
| 6,558,344 B2 | 5/2003 | McKinnon et al. |
| 6,561,808 B2 | 5/2003 | Neuberger et al. |
| D475,346 S | 6/2003 | McCurrach et al. |
| D476,743 S | 7/2003 | D'Silva |
| 6,589,477 B1 | 7/2003 | Frieze et al. |
| 6,602,071 B1 | 8/2003 | Ellion et al. |
| 6,632,091 B1 | 10/2003 | Cise et al. |
| D482,451 S | 11/2003 | Page et al. |
| 6,640,999 B2 | 11/2003 | Peterson |
| 6,647,577 B2 | 11/2003 | Tam |
| 6,659,674 B2 | 12/2003 | Carlucci et al. |
| 6,663,386 B1 | 12/2003 | Moelsgaard |
| 6,669,059 B2 | 12/2003 | Mehta |
| D484,971 S | 1/2004 | Hartwein |
| 6,681,418 B1 | 1/2004 | Bierend |
| D486,573 S | 2/2004 | Callaghan et al. |
| 6,689,078 B1 | 2/2004 | Rehkemper et al. |
| 6,699,208 B2 | 3/2004 | Bachman et al. |
| 6,719,561 B2 | 4/2004 | Gugel et al. |
| D489,183 S | 5/2004 | Akahori et al. |
| 6,739,782 B1 | 5/2004 | Rehkemper et al. |
| 6,740,053 B2 | 5/2004 | Kaplowitz |
| D490,899 S | 6/2004 | Gagnon |
| D491,728 S | 6/2004 | Jimenez |
| D492,996 S | 7/2004 | Rehkemper et al. |
| 6,761,324 B2 | 7/2004 | Chang |
| 6,766,549 B2 | 7/2004 | Klupt |
| D495,142 S | 8/2004 | Berde |
| D495,143 S | 8/2004 | Berde |
| 6,779,216 B2 | 8/2004 | Davies et al. |
| 6,783,004 B1 | 8/2004 | Rinner |
| 6,783,505 B1 | 8/2004 | Li |
| 6,796,796 B2 | 9/2004 | Segal |
| 6,808,331 B2 | 10/2004 | Hall et al. |
| D498,643 S | 11/2004 | Pryor |
| 6,814,259 B1 | 11/2004 | Foster et al. |
| D499,885 S | 12/2004 | Xi |
| 6,835,181 B2 | 12/2004 | Hippensteel |
| D500,599 S | 1/2005 | Callaghan |
| 6,836,917 B2 | 1/2005 | Blaustein et al. |
| 6,837,708 B2 | 1/2005 | Chen et al. |
| 6,884,069 B2 | 4/2005 | Goldman |
| 6,902,337 B1 | 6/2005 | Kuo |
| 6,907,879 B2 | 6/2005 | Drinan et al. |
| D509,585 S | 9/2005 | Kling et al. |
| D513,638 S | 1/2006 | Pan |
| D515,215 S | 2/2006 | Wang |
| 6,997,393 B1 | 2/2006 | Angold ................... B05B 15/74 239/205 |
| D522,652 S | 6/2006 | Massey |
| 7,080,980 B2 | 7/2006 | Klupt |
| D529,661 S | 10/2006 | Schmidt |
| D530,010 S | 10/2006 | Luettgen et al. |
| 7,117,555 B2 | 10/2006 | Fattori et al. |
| D532,570 S | 11/2006 | Vizcarra |
| 7,131,838 B2 | 11/2006 | Suzuki et al. |
| D533,720 S | 12/2006 | Vu |
| 7,147,468 B2 | 12/2006 | Snyder et al. |
| D538,474 S | 3/2007 | Sheppard et al. |
| 7,235,176 B1 | 6/2007 | Takagi |
| D548,334 S | 8/2007 | Izumi |
| D550,097 S | 9/2007 | Lepoitevin |
| D553,980 S | 10/2007 | VerWeyst |
| 7,276,035 B2 | 10/2007 | Lu |
| 7,314,456 B2 | 1/2008 | Shaw |
| D565,175 S | 3/2008 | Boyd et al. |
| 7,344,510 B1 | 3/2008 | Yande |
| D565,713 S | 4/2008 | Gao |
| 7,367,803 B2 | 5/2008 | Egeresi |
| D574,952 S | 8/2008 | Boyd et al. |
| 7,414,337 B2 | 8/2008 | Wilkinson et al. |
| D577,198 S | 9/2008 | Jimenez |
| D577,814 S | 9/2008 | Seki et al. |
| D581,279 S | 11/2008 | Oates |
| 7,455,521 B2 | 11/2008 | Fishburne, Jr. |
| 7,469,440 B2 | 12/2008 | Boland et al. |
| D585,132 S | 1/2009 | Pukall |
| D588,262 S | 3/2009 | Pukall |
| 7,500,584 B2 | 3/2009 | Schutz |
| D590,492 S | 4/2009 | Powell |
| D592,748 S | 5/2009 | Boulton |
| D595,136 S | 6/2009 | Canamasas Puigbo |
| D601,694 S | 10/2009 | Rocklin |
| D601,697 S | 10/2009 | Sobeich et al. |
| D603,708 S | 11/2009 | Handy |
| D608,430 S | 1/2010 | Slothower |
| 7,670,141 B2 | 3/2010 | Thomas et al. |
| 7,677,888 B1 | 3/2010 | Halm |
| D613,550 S | 4/2010 | Picozza et al. |
| D621,949 S | 8/2010 | Seki et al. |
| D622,928 S | 9/2010 | Griebel |
| D623,376 S | 9/2010 | Griebel |
| D625,406 S | 10/2010 | Seki et al. |
| 7,814,585 B1 | 10/2010 | Reich |
| D629,884 S | 12/2010 | Stephens |
| 7,857,623 B2 | 12/2010 | Grez |
| 7,862,536 B2 | 1/2011 | Chen et al. |
| 7,866,626 B1 | 1/2011 | MacLean-Blevins |
| 7,959,597 B2 | 6/2011 | Baker et al. |
| D640,872 S | 7/2011 | Nanda |
| D648,539 S | 11/2011 | Wai |
| D651,409 S | 1/2012 | Papenfu |
| D651,805 S | 1/2012 | Hay |
| D653,340 S | 1/2012 | Goerge et al. |
| 8,113,832 B2 | 2/2012 | Snyder et al. |
| D655,380 S | 3/2012 | Taylor |
| D658,381 S | 5/2012 | Gebski |
| D658,538 S | 5/2012 | Korzeniowski |
| 8,220,726 B2 | 7/2012 | Qiu et al. |
| D666,912 S | 9/2012 | Kawai |
| 8,256,979 B2 | 9/2012 | Hilscher et al. |
| D668,339 S | 10/2012 | Luoto |
| D669,169 S | 10/2012 | Washington et al. |
| 8,297,534 B2 | 10/2012 | Li et al. |

(56) References Cited

U.S. PATENT DOCUMENTS

| | | | |
|---|---|---|---|
| D670,373 S | 11/2012 | Taylor et al. |
| D670,958 S | 11/2012 | Picozza et al. |
| D671,637 S | 11/2012 | Gebski et al. |
| D672,018 S | 12/2012 | Bucher |
| 8,366,024 B2 | 2/2013 | Leber et al. |
| 8,403,577 B2 | 3/2013 | Khoshnevis |
| 8,403,665 B2 | 3/2013 | Thomas et al. |
| 8,408,483 B2 | 4/2013 | Boyd et al. |
| 8,418,300 B2 | 4/2013 | Miller et al. |
| D686,311 S | 7/2013 | Mori |
| D694,378 S | 11/2013 | Bates |
| D694,398 S | 11/2013 | Taylor |
| D700,343 S | 2/2014 | Liu |
| D702,819 S | 4/2014 | Garland |
| D702,821 S | 4/2014 | Garland |
| D707,350 S | 6/2014 | Woodard |
| D709,183 S | 7/2014 | Kemlein |
| D714,929 S | 10/2014 | Kim et al. |
| D714,930 S | 10/2014 | Kim et al. |
| D717,412 S | 11/2014 | Bucher |
| D717,427 S | 11/2014 | Kim |
| D718,855 S | 12/2014 | Kim et al. |
| D723,387 S | 3/2015 | Fath |
| D725,770 S | 3/2015 | Kim et al. |
| D731,640 S | 6/2015 | Kim et al. |
| D735,305 S | 7/2015 | Obara |
| D740,936 S | 10/2015 | Kim et al. |
| D745,329 S | 12/2015 | Ong |
| D746,975 S | 1/2016 | Schenck |
| D747,464 S | 1/2016 | Taylor |
| D754,330 S | 4/2016 | Kim et al. |
| D756,122 S | 5/2016 | Taylor |
| D764,051 S | 8/2016 | Wang |
| D766,423 S | 9/2016 | Kim et al. |
| D772,396 S | 11/2016 | Kim et al. |
| D772,397 S | 11/2016 | Kim et al. |
| D774,651 S | 12/2016 | Kaib |
| D776,253 S | 1/2017 | Li |
| D782,326 S | 3/2017 | Fath |
| D782,656 S | 3/2017 | Au |
| D786,422 S | 5/2017 | Au |
| 9,642,677 B2 | 5/2017 | Luettgen et al. |
| D788,907 S | 6/2017 | Kim |
| D798,440 S | 9/2017 | Kim |
| D802,119 S | 11/2017 | Kim |
| D809,650 S | 2/2018 | Kim |
| 10,779,922 B2 | 9/2020 | Wagner |
| 10,835,356 B2 | 11/2020 | Williams |
| 11,213,376 B2 * | 1/2022 | Senff ................ A61C 17/0202 |
| 2002/0090252 A1 | 7/2002 | Hall et al. |
| 2002/0108193 A1 | 8/2002 | Gruber |
| 2002/0119415 A1 | 8/2002 | Bailey |
| 2002/0152565 A1 | 10/2002 | Klupt |
| 2002/0193716 A1 | 12/2002 | Bachman et al. |
| 2003/0060743 A1 | 3/2003 | Chang |
| 2003/0098249 A1 | 5/2003 | Rollock |
| 2003/0162146 A1 | 8/2003 | Shortt et al. |
| 2003/0204155 A1 | 10/2003 | Egeresi |
| 2003/0213075 A1 | 11/2003 | Hui et al. |
| 2004/0045107 A1 | 3/2004 | Egeresi |
| 2004/0076921 A1 | 4/2004 | Gofman et al. |
| 2004/0122377 A1 | 6/2004 | Fischer et al. |
| 2004/0126730 A1 | 7/2004 | Panagotacos |
| 2004/0180569 A1 | 10/2004 | Chiou |
| 2004/0209222 A1 | 10/2004 | Snyder |
| 2005/0049620 A1 | 3/2005 | Chang |
| 2005/0064371 A1 | 3/2005 | Soukos et al. |
| 2005/0101894 A1 | 5/2005 | Hippensteel |
| 2005/0102773 A1 | 5/2005 | Obermann et al. |
| 2005/0144745 A1 | 7/2005 | Russell |
| 2005/0177079 A1 | 8/2005 | Pan |
| 2005/0271531 A1 | 12/2005 | Brown et al. |
| 2006/0008373 A1 | 1/2006 | Schutz |
| 2006/0010624 A1 | 1/2006 | Cleland |
| 2006/0026784 A1 | 2/2006 | Moskovich et al. |
| 2006/0057539 A1 | 3/2006 | Sodo |
| 2006/0078844 A1 | 4/2006 | Goldman et al. |
| 2006/0079818 A1 | 4/2006 | Yande |
| 2006/0207052 A1 | 9/2006 | Tran |
| 2007/0077810 A1 | 4/2007 | Gogel ................... H01R 13/60 |
| | | | 439/505 |
| 2007/0082316 A1 | 4/2007 | Zhadanov et al. |
| 2007/0082317 A1 | 4/2007 | Chuang |
| 2007/0113360 A1 | 5/2007 | Tsai |
| 2007/0199616 A1 | 8/2007 | Chotenovsky ...... A61M 16/183 |
| | | | 141/351 |
| 2007/0202459 A1 | 8/2007 | Boyd et al. |
| 2007/0203439 A1 | 8/2007 | Boyd et al. |
| 2007/0254260 A1 | 11/2007 | Alden |
| 2008/0189951 A1 | 8/2008 | Molema et al. |
| 2008/0213719 A1 | 9/2008 | Giniger et al. |
| 2008/0253906 A1 | 10/2008 | Strong |
| 2009/0070949 A1 | 3/2009 | Sagel et al. |
| 2009/0071267 A1 | 3/2009 | Mathus et al. |
| 2009/0082706 A1 | 3/2009 | Shaw |
| 2009/0124945 A1 | 5/2009 | Reich et al. |
| 2009/0139351 A1 | 6/2009 | Reichmuth |
| 2009/0142205 A1 | 6/2009 | Yajima |
| 2009/0163839 A1 | 6/2009 | Alexander |
| 2009/0188780 A1 | 7/2009 | Watanabe |
| 2009/0281454 A1 | 11/2009 | Baker et al. |
| 2010/0010524 A1 | 1/2010 | Barrington |
| 2010/0015566 A1 | 1/2010 | Shaw |
| 2010/0049177 A1 | 2/2010 | Boone, III et al. |
| 2010/0190132 A1 | 7/2010 | Taylor et al. |
| 2010/0239998 A1 | 9/2010 | Snyder et al. |
| 2010/0261134 A1 | 10/2010 | Boyd et al. |
| 2010/0261137 A1 * | 10/2010 | Boyd ................. A61C 17/0205 |
| | | | 433/88 |
| 2010/0326536 A1 | 12/2010 | Nan |
| 2010/0330527 A1 | 12/2010 | Boyd et al. |
| 2011/0027749 A1 | 2/2011 | Syed |
| 2011/0076090 A1 | 3/2011 | Wu et al. |
| 2011/0097683 A1 | 4/2011 | Boyd et al. |
| 2011/0139826 A1 | 6/2011 | Hair et al. |
| 2011/0144588 A1 | 6/2011 | Taylor et al. |
| 2011/0184341 A1 | 7/2011 | Baker et al. |
| 2011/0307039 A1 | 12/2011 | Cornell |
| 2012/0021374 A1 | 1/2012 | Cacka et al. |
| 2012/0045730 A1 | 2/2012 | Snyder et al. |
| 2012/0064480 A1 | 3/2012 | Hegemann |
| 2012/0077145 A1 | 3/2012 | Tsurukawa |
| 2012/0141952 A1 | 6/2012 | Snyder et al. |
| 2012/0179118 A1 | 7/2012 | Hair |
| 2012/0189976 A1 | 7/2012 | McDonough et al. |
| 2012/0266396 A1 | 10/2012 | Leung |
| 2012/0277663 A1 | 11/2012 | Millman et al. |
| 2012/0277677 A1 | 11/2012 | Taylor et al. |
| 2012/0277678 A1 | 11/2012 | Taylor et al. |
| 2012/0279002 A1 | 11/2012 | Sokol et al. |
| 2012/0295220 A1 | 11/2012 | Thomas et al. |
| 2013/0089832 A1 | 4/2013 | Lee |
| 2013/0140382 A1 | 6/2013 | Eley et al. |
| 2013/0295520 A1 | 11/2013 | Hsieh |
| 2013/0298340 A1 | 11/2013 | Suwanbutr |
| 2014/0106296 A1 | 4/2014 | Woodard et al. |
| 2014/0116261 A1 | 5/2014 | Chen .................... A47J 27/122 |
| | | | 99/339 |
| 2014/0193774 A1 | 7/2014 | Snyder et al. |
| 2014/0259474 A1 | 9/2014 | Sokol et al. |
| 2014/0272769 A1 | 9/2014 | Luettgen et al. |
| 2014/0272782 A1 | 9/2014 | Luettgen et al. |
| 2014/0352088 A1 | 12/2014 | Wu |
| 2014/0356810 A1 | 12/2014 | Novak |
| 2015/0004559 A1 | 1/2015 | Luettgen et al. |
| 2015/0147717 A1 | 5/2015 | Taylor et al. |
| 2015/0173850 A1 | 6/2015 | Garrigues et al. |
| 2015/0182319 A1 | 7/2015 | Wagner et al. |
| 2016/0100921 A1 | 4/2016 | Ungar |
| 2016/0151133 A1 | 6/2016 | Luettgen et al. |
| 2017/0049530 A1 | 2/2017 | Cacka |
| 2017/0114495 A1 | 4/2017 | Date et al. |

(56) References Cited

U.S. PATENT DOCUMENTS

| | | | |
|---|---|---|---|
| 2017/0239132 | A1 | 8/2017 | Luettgen et al. |
| 2020/0405463 | A1 | 12/2020 | Williams |

FOREIGN PATENT DOCUMENTS

| | | | | |
|---|---|---|---|---|
| CA | 3012050 | C | 12/2020 | |
| CH | 569905 | A5 | 11/1975 | |
| CH | 655237 | | 4/1986 | |
| CH | 666807 | A5 | 8/1988 | |
| CN | 87103004 | | 12/1987 | |
| CN | 2149184 | Y | 12/1993 | |
| CN | 2508721 | | 9/2002 | |
| CN | 2524708 | Y | 12/2002 | |
| CN | 2536202 | Y | 2/2003 | |
| CN | 1596842 | | 3/2005 | |
| CN | 2690629 | | 4/2005 | |
| CN | 101000026 | | 7/2007 | |
| CN | 201028082 | | 2/2008 | |
| CN | 101286668 | | 10/2008 | |
| CN | 201231191 | Y | 5/2009 | |
| CN | 201237779 | | 5/2009 | |
| CN | 100591625 | C | 2/2010 | |
| CN | 101680559 | | 3/2010 | |
| CN | 201691300 | U | 1/2011 | |
| CN | 201754925 | U | 3/2011 | |
| CN | 102297303 | | 12/2011 | |
| CN | 102406518 | | 4/2012 | |
| CN | 103069169 | | 4/2013 | |
| CN | 202982290 | | 6/2013 | |
| CN | 210727917 | | 6/2013 | |
| CN | 203057733 | | 7/2013 | |
| CN | 203539471 | | 4/2014 | |
| CN | 103813833 | | 5/2014 | |
| CN | 103883779 | | 6/2014 | |
| CN | 203641646 | | 6/2014 | |
| CN | 203693807 | | 6/2014 | |
| CN | 203693808 | U | 7/2014 | |
| CN | 203749625 | | 8/2014 | |
| CN | 203823181 | | 9/2014 | |
| CN | 203829079 | | 9/2014 | |
| CN | 203953860 | U | 11/2014 | |
| CN | 204049908 | | 12/2014 | |
| CN | 204049908 | U | 12/2014 | |
| CN | 204242510 | | 4/2015 | |
| CN | 204562437 | | 8/2015 | |
| CN | 104956069 | | 9/2015 | |
| CN | 204683825 | | 10/2015 | |
| CN | 105103070 | | 11/2015 | |
| CN | 204766008 | | 11/2015 | |
| CN | 105828745 | | 8/2016 | |
| CN | 108778182 | | 11/2018 | |
| CN | 211271294 | | 8/2020 | |
| CN | 215130643 | | 12/2021 | |
| CN | 217960366 | | 12/2022 | |
| DE | 1059879 | * | 6/1959 | |
| DE | 1059879 | B | 6/1959 | |
| DE | 1466963 | | 5/1969 | |
| DE | 2019003 | | 11/1971 | |
| DE | 2409752 | | 9/1975 | |
| DE | 2545936 | | 4/1977 | |
| DE | 2714876 | | 10/1978 | |
| DE | 2910982 | | 2/1980 | |
| DE | 3101941 | | 8/1982 | |
| DE | 3346651 | | 7/1985 | |
| DE | 10248338 | | 5/2004 | |
| DE | 102007030555 | | 1/2009 | |
| EP | 0023672 | | 7/1980 | |
| EP | 229207 | | 7/1987 | |
| EP | 0452474 | | 10/1991 | |
| EP | 0515983 | | 2/1992 | |
| EP | 1825827 | | 8/2007 | |
| EP | 1825827 | A2 | 8/2007 | |
| EP | 3407828 | B1 | 12/2020 | |
| EP | 3554420 | B1 | 5/2021 | |
| ES | 460563 | | 5/1978 | |
| FR | 2556954 | | 6/1982 | |
| FR | 2654627 | | 5/1991 | |
| GB | 472053 | | 9/1937 | |
| GB | 838564 | | 6/1960 | |
| GB | 1182031 | | 2/1970 | |
| GB | 1456322 | | 11/1976 | |
| GB | 2018605 | | 10/1979 | |
| JP | 55086451 | | 6/1980 | |
| JP | 55086451 | A | 6/1980 | |
| JP | 55148553 | | 11/1980 | |
| JP | S55148553 | | 11/1980 | |
| JP | 56090220 | | 7/1981 | |
| JP | 56115927 | | 9/1981 | |
| JP | 56115927 | U | 9/1981 | |
| JP | H01141668 | | 6/1989 | |
| JP | 02134150 | | 5/1990 | |
| JP | H0541516 | | 6/1993 | |
| JP | 06035569 | | 2/1994 | |
| JP | 10094747 | | 4/1998 | |
| JP | 10094747 | A | 4/1998 | |
| JP | 3140756 | B2 | 3/2001 | |
| JP | 2002532148 | | 10/2002 | |
| JP | 2002532148 | A | 10/2002 | |
| JP | 2006189068 | | 7/2006 | |
| JP | 2006226497 | | 8/2006 | |
| JP | 3140756 | U | 3/2008 | |
| JP | 2009-39455 | | 2/2009 | |
| JP | 2009275581 | | 11/2009 | |
| JP | 2016098679 | | 5/2016 | |
| JP | 6694965 | B2 | 4/2020 | |
| JP | 6889310 | | 5/2021 | |
| KR | 200319001 | | 7/2003 | |
| KR | 20050067949 | | 7/2005 | |
| KR | 20100028231 | | 3/2010 | |
| KR | 20100029231 | | 3/2010 | |
| KR | 20120126265 | | 11/2012 | |
| KR | 20140099673 | | 8/2014 | |
| KR | 102072661 | B1 | 2/2020 | |
| WO | WO95/016404 | | 6/1995 | |
| WO | WO2000035403 | | 6/2000 | |
| WO | WO01/10327 | | 2/2001 | |
| WO | WO0145631 | | 6/2001 | |
| WO | WO-0145631 | A2 | 6/2001 | ......... A61H 33/0095 |
| WO | WO04/021958 | | 3/2004 | |
| WO | WO04/039205 | | 5/2004 | |
| WO | WO2004/060259 | | 7/2004 | |
| WO | WO2004/062518 | | 7/2004 | |
| WO | WO2008/070730 | | 6/2008 | |
| WO | WO2008/157585 | | 12/2008 | |
| WO | WO2013/124691 | | 8/2013 | |

OTHER PUBLICATIONS

Suvo. "Helical Gears vs Spur Gears—Advantages and Disadvantages Compared." Brighthub Engineering, Aug. 18, 2010, www.brighthubengineering.com/manufacturing-technology/33535-helical-gears-vs-spur-gears/., 7 pages.

Waterpik ADA Accepted WP-663, posted at amazon.com, earliest date reviewed on Feb. 6, 2014, [online], acquired on Feb. 12, 2018. Available from Internet, <URL: https://www.amazon.com/Waterpik-Accepted-WP-663-Aquarius-Flosser/dp/B072JFVXSY/ref=cm_cr_arp_d_product_top?ie=UTF8&th=1> (Year: 2014).

Waterpik Classic Professional Water Flosser, WP-72, posted at amazon.com, earliest date reviewed on Mar. 5, 2016, [online], acquired on Feb. 23, 2018. Available from Internet, <URL: https://www.amazon.com/Waterpik-Classic-Professional-Flosser-WP-72/dp/B00HFQQOU6/ref=cm_cr_arp_d_product_top?ie=UTF8> (Year: 2016).

The Right Tool, Electron Fusion Devices, Inc., 2 pages, at least as early as Feb. 1991.

Japanese Packaging, 2 pages, at least as early as Dec. 2002.

Japanese Instruction Brochure, 20 pages, at least as early as Dec. 2002.

Brochure: Woog International, "You have a 98% chance of getting gum disease. Unless you read this.", Lancaster, Pennsylvania, 5 pages, Feb. 1987.

(56) References Cited

OTHER PUBLICATIONS

Brochure: Woog International, "We put the control of home dental care back into the hands of the professional", Lancaster, Pennsylvania, 2 pages, Feb. 1987.
Brochure: WOOG International, "Products at a Glance: Home Dental Care System" WOOG ORAJET, 3 pages, at least as early as Dec. 18, 1998.
Website: http://www.just4teeth.com/product/Panasonic/Panasonic_Portable_Irrigator.htm, 2 pages, at least as early as Jun. 20, 2003.
Website: http://www.videodirectstore.com/store/merchant.mv?Screen=PROD&Product_Code=EW1'...", 2 pages, at least as early as Jun. 20, 2003.
Website: http://products.consumerguide.com/cp/family/review/index.cfm/id/18742, 2 pages, at least as early as Jun. 20, 2003.
Website: http://www.racekarteng.com/images/walbroparts.gif and http://www.muller.net/mullermachine/docs/walbro1.html, 4 pages, at least as early as Jun. 20, 2003.
European Search Report, EPO Application No. 07250799.9, Jul. 5, 2007.
European Search Report, EPO Application No. 07252693.2, 14 pages, Apr. 28, 2008.
European Examination Report, EPO Application No. 07250799.9, Feb. 5, 2009.
International Search Report, Application No. PCT/US2010/028180, 2 pages, May 18, 2010.
International Search Report, PCT/US2010/060800, 2 pages, Feb. 11, 2011.
International Search Report, PCT/US2011/052795, 10 pages, Jan. 17, 2012.
Waterpik SinuSense Website: http://www.insightsbyapril.com/2012/03/waterpik-natural-remedy-for-sinus.html, 8 pages, retrieved on May 31, 2012.
Website: https://www.waterpik.com/about-us/, 3 pages.
Waterpik WP 350W Oral Irrigator. Dentist.net. Copyright date 2013. Date accessed: Mar. 30, 2017, 2 pages <http://www.dentalhoo.com/waterpik-wp350.asp>.
IPik Portable Oral Irrigator. AliExpress. Date reviewed: Oct. 5, 2016. <https://www.allexpress.com/ . . . e-Oral-Care-Product-Nasal-Irrigator-Tooth-Flosser-Water/1525541997.html?aft_platform=aaf&cpt=1490913714609&sk=yfAeyJa&aft_trace_key=c5a300c4f02e46d08c04215292e1762f-1490913714609-07517-ytAeyJa>, 18 pages.
Brite Leafs Professional Portable 2-in-1 Nasal Sinus & Oral Irrigator. Brite Leafs. Copyright date 2012, <http://www.briteleafs.com/product6.html> , 1 page.
AliExpress. Date reviewed: Jan. 12, 2017. <https://www.aliexpress.com/item/Cordless-Water-Floss-Portable-Oral-Irrigator-Dental-Water-Flosser-Waterpic-Whatpick-Dental-Water-Pic-Whater-Pick/32769416341.html?spm=2114.40010308.4.75.Owuzfj>.

* cited by examiner

REDUCED FORM FACTOR ORAL IRRIGATOR

CROSS REFERENCE TO RELATED APPLICATIONS

This application is a continuation application of U.S. non-provisional application Ser. No. 15/415,750, filed on Jan. 25, 2017, entitled "Reduced Form Factor Oral Irrigator," which claims priority to U.S. provisional application No. 62/286,925 filed on 25 Jan. 2016 entitled "Reduced Form Factor Oral Irrigator," and U.S. provisional application No. 62/416,926 filed on 3 Nov. 2016 entitled "Reduced Form Factor Oral Irrigator," each of which is incorporated by reference herein in its entirety.

This application is related to U.S. provisional application No. 62/286,792 filed on 25 Jan. 2016 entitled "Swivel Assembly for Oral Irrigator Handle," which is incorporated by reference herein in its entirety.

TECHNICAL FIELD

The present disclosure relates generally to health and personal hygiene equipment and more particularly, to oral irrigators.

BACKGROUND

Oral irrigators typically are used to clean a user's teeth and gums by discharging a pressurized fluid stream into a user's oral cavity. The fluid impacts the teeth and gums to remove debris. Countertop oral irrigator units include a large reservoir that connects to a base unit housing the pump and other internal components. These units are typically too large to be easily portable and therefore many users do not travel with countertop units. Handheld oral irrigator units are smaller than most countertop units and may include a handle housing internal components, such as a pump, motor, etc., and a reservoir integrated with the handle or connected to the handle. While handheld irrigator units are typically smaller than countertop units and more easily portable, because the reservoir is connected to the handle, it often is smaller than countertop unit reservoirs and thus may not provide as much fluid for irrigating as desired by a user.

The information included in this Background section of the specification, including any references cited herein and any description or discussion thereof, is included for technical reference purposes only and is not to be regarded subject matter by which the scope of the invention as defined in the claims is to be bound.

SUMMARY

In one implementation, an oral irrigator may be composed of a removable reservoir defining a reservoir cavity, a base unit housing a motor and a pump, and a handle for directing fluid flow from the pump removably connected to the base unit and fluidly coupled to the pump by a hose. The handle may further include a housing defining a slot formed in an outer wall of the housing. The slot may be bounded by two opposing walls spaced apart from each other and a transverse wall at a terminal interior end of the opposing walls such that the outer wall of the housing is open to the slot at lateral sides of the two opposing walls and at a base end of the opposing walls opposite the transverse wall. In a first configuration the reservoir is coupled to a top surface of the base unit and the reservoir cavity is fluidly coupled to the pump. In a second configuration, the base unit is fluidly decoupled from the reservoir cavity and the base unit is positioned within the reservoir cavity.

In another implementation, a handle for an oral irrigator for directing a focused stream of fluid has a housing defining a slot formed in an outer wall of the housing. The slot may be bounded by two opposing walls spaced apart from each other and a transverse wall at a terminal interior end of the opposing walls such that the outer wall of the housing is open to the slot at lateral sides of the two opposing walls and at a base end of the opposing walls opposite the transverse wall. In some implementations, the opposing walls are parallel to each other. In other implementations, the two opposing walls are planar. In some implementations, the opposing walls are both planar and parallel to each other. In further implementations, the handle may extend from a first end to a second end in a generally elongate form along a longitudinal axis and the opposing walls defining the slot extend at an angle with respect to the longitudinal axis.

In another implementation, an oral irrigator may include a removable reservoir defining a reservoir cavity, a base unit housing a motor and a pump, and a power assembly in selective communication with the motor. In a first configuration the reservoir is coupled to a top surface of the base unit, the reservoir cavity is fluidly coupled to the pump, and the power assembly is electrically connected to the motor. In a second configuration, the base unit is fluidly decoupled from the reservoir cavity, the base unit is positioned within the reservoir cavity, and the power assembly is electrically disconnected from the motor and is received within a cavity defined in the base unit. In further implementations, the base unit may include a base magnetic material. The power assembly may similarly include a retaining magnetic material. The base magnetic material and the retaining magnetic material may be aligned opposite to each other when the oral irrigator is in the second configuration and attract each other to thereby secure the power assembly within the base unit.

In a further implementation, an oral irrigator may include a base unit, a removable reservoir, and a belt drive assembly. The base unit may house a motor and a pump. The removable reservoir may define a reservoir cavity configured to mechanically couple to a top surface of the base unit and fluidly couple the reservoir cavity to the pump. The belt drive assembly may connect the motor to the pump. The belt drive assembly may further include a drive pulley connected to an output shaft of the motor, a driven pulley spaced apart from the drive pulley and mechanically connected to a piston that drives the pump, and a continuous belt connecting the drive pulley to the driven pulley. In a further implementation, a tensioning structure may exert a tension force on the belt. In yet a further implementation, the tensioning structure may include an idler pulley and a tension member. The idler pulley may be positioned between and pivotably mounted with respect to the drive pulley and the driven pulley and positioned in contact with the belt. The tension member connected to the idler pulley and configured to pull the idler pulley about a pivot to maintain a contact force with the belt. In a further implementation, the base unit may include a chassis to which each of the motor, the driven pulley, and the idler pulley are attached. A bracket may be pivotably attached to the chassis. The idler pulley may be rotationally attached to the bracket. The tension member may be connected to the bracket at a first end and connected to the chassis at a second end. IN an additional implementation, the tension member is a torsion spring, the bracket is L-shaped, the idler pulley is attached to a first terminal end of the L-shaped bracket, and a first end of the torsion spring is attached to a second terminal end of the L-shaped bracket. A center axis of the torsion spring may be aligned with a pivot point of the L-shaped bracket.

In another implementation, an oral irrigator may include a base unit and a removable reservoir. The base unit may be encased by a housing covering a motor and drive system positioned in a first, dry compartment formed in the base unit housing and a pump positioned in a second, wet compartment formed in the base unit housing. The removable reservoir may define a reservoir cavity configured to mechanically couple to a top surface of the base unit and fluidly couple the reservoir cavity to the pump. A piston may be connected at a first end to the drive system and connected at a second end to the pump. A diaphragm seal may be positioned between the dry compartment and the wet compartment through which the piston passes. The diaphragm seal may further include a frame, two elastomeric bead seals, and an elastomeric bellows. The frame may be made of a rigid material, define a center aperture, and have a dry face oriented toward the dry compartment and a wet face oriented toward the wet compartment. A first elastomeric bead seal may be formed at least partially along and adjacent to at least a portion of a perimeter edge of the dry face. A second elastomeric bead seal may be formed at least partially along and adjacent to at least a portion of a perimeter edge of the wet face. The elastomeric bellows may seal against and extend across the center aperture. The bellows may further define a center opening configured to receive and seal about a shaft portion of the piston.

In a further implementation, an oral irrigator may include a base unit, a removable reservoir, a handle, a first poppet valve, and a second poppet valve. The base unit may house a motor and a pump. The removable reservoir may define a reservoir cavity configured to mechanically couple to a top surface of the base unit and fluidly couple the reservoir cavity to the pump. The handle may be removably connected to the base unit and fluidly coupled to the pump by a hose to direct fluid flow from the pump. The first poppet valve may be positioned in a removable connector attached at a first end to the hose and releasably attached at a second end to a port in the base unit in fluid communication with the pump. The first poppet valve may be configured to open in response to fluid under pressure received from the pump to allow fluid to flow through the hose to the handle. The first poppet valve may also be configured to close in the absence of fluid under pressure received from the pump. The second poppet valve may be positioned in the port and configured to open in response to connection with the connector and configured to close when the connector is removed from the port. In additional implementations, a shuttle valve may be positioned in the base unit in fluid communication with the pump at a first end and with the reservoir at a second end. The shuttle valve may be configured to block a primary fluid flow passage to the reservoir when the pump provides a positive pressure stroke and configured to open the primary fluid flow passage to the reservoir when the pump provides a negative pressure stroke. A third poppet valve may be housed in a valve cavity defined within the shuttle valve. The third poppet valve may be configured to block fluid flow from the reservoir through the valve cavity and configured to open and allow fluid flow through the valve cavity toward the reservoir when fluid pressure at the first end of the shuttle valve exceeds a threshold pressure.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments of the invention and illustrated in the accompanying drawings.

DETAILED DESCRIPTION

Figure 1A:
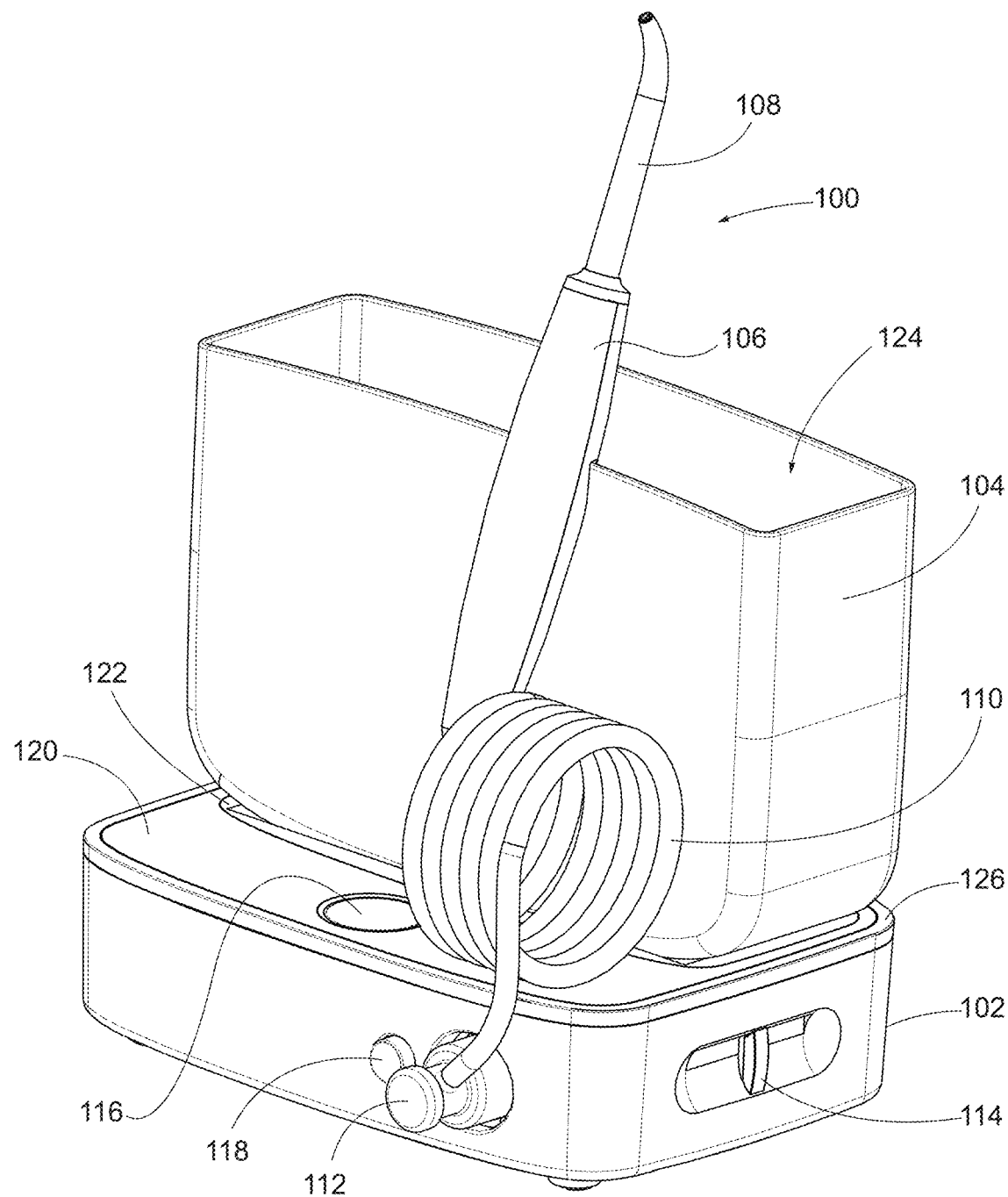
FIG. 1A is a front isometric view of an oral irrigator.

An example of the present disclosure includes an oral irrigator having a reduced form factor as compared to conventional countertop oral irrigators. The oral irrigator includes a base, a removable reservoir, a power assembly, a drive assembly, a handle, and a pump assembly. In one embodiment the reservoir and power assembly are each reconfigurable from a storage or collapsed position to a use or expanded position. For example, the reservoir can transition from being seated on a top surface of the base in the use position to the storage position where it is disconnected from the base unit and the base unit is inserted into the reservoir cavity for storage. Similarly, the power assembly stores within a compartment in the base but is removed from the base and connected to an electrical source, such as a power outlet, for use. The handle can also be selectively connected with and disconnected from the base and reservoir to allow the handle to be removed and stored when desired. Countertop irrigators use regular outlets (100-240V outlets) and are therefore more powerful and potentially more desirable to a user than handheld units, which typically use a 2.4V battery pack. In addition, countertop irrigators are ready for use at any time as long as an outlet is available. In contrast, handheld irrigators must be charged before they can be used. For travel, a user may forget to charge the unit before departure and the unit may not be operational when the user arrives at his destination The oral irrigator may also include a drive assembly having reduced noise as compared to conventional oral irrigators. The drive assembly includes a pinion pulley driven by a motor, a driven pulley indirectly driven by a pinion pulley, and a belt connected to the pinion pulley and the driven pulley to transfer motion from the pinion pulley to the driven pulley. The belt seats on the outer surface of the two pulleys and reduces noise generated by the drive assembly as the pulleys, unlike gears, do not physically mesh with one another in order to transfer motion therebetween. The drive assembly may also include a tension assembly to insure that the belt drive tension remains at an appropriate level based upon the load on the motor.

The driven pulley is connected to a connecting rod that drives a piston to pump fluid between a reservoir and a handle. In one embodiment, the connecting rod includes a bend or elbow extension. The bend allows a seal structure to seat around and seal against the connecting rod.

The oral irrigator includes a number of different valves for preventing fluid leakage in the storage and use configurations. For example, the base and the handle each include connectors for sealing inlets and outlets when the handle and base are disconnected from one another. These connectors prevent the hose connected to the handle and the aperture in the base for receiving the hose from leaking fluid when the oral irrigator is not in use.

Overview of the Oral Irrigator

With reference now to the figures, the oral irrigator of the present disclosure will be discussed in more detail. FIGS. 1A-1D illustrate various views of an oral irrigator. With reference to FIGS. 1A-1D, the oral irrigator 100 includes a base 102, a reservoir 104, a handle 106 connected to a tip 108, and a hose 110 fluidly connecting the handle 106 to the base 102. The oral irrigator 100 also includes a power assembly 134 removably connected to the base 102 and configured to electrically connect to the base 102 to provide power to various components within the oral irrigator 100. The reservoir 104, handle 106, and hose 110 are removably connected to the base 102, allowing the oral irrigator 100 to be collapsed to a storage configuration and inserted into a travel carry bag or other container for storage or transport.

The base 102 houses a motor, a pump assembly, a pressure assembly, and various connectors to fluidly connect the handle 106 to the reservoir 104 and to pull fluid from the reservoir 104 and expel it from the outlet of the tip 108. Each of the various components of the oral irrigator 100 will be discussed in detail below.

Reservoir

Figure 2:
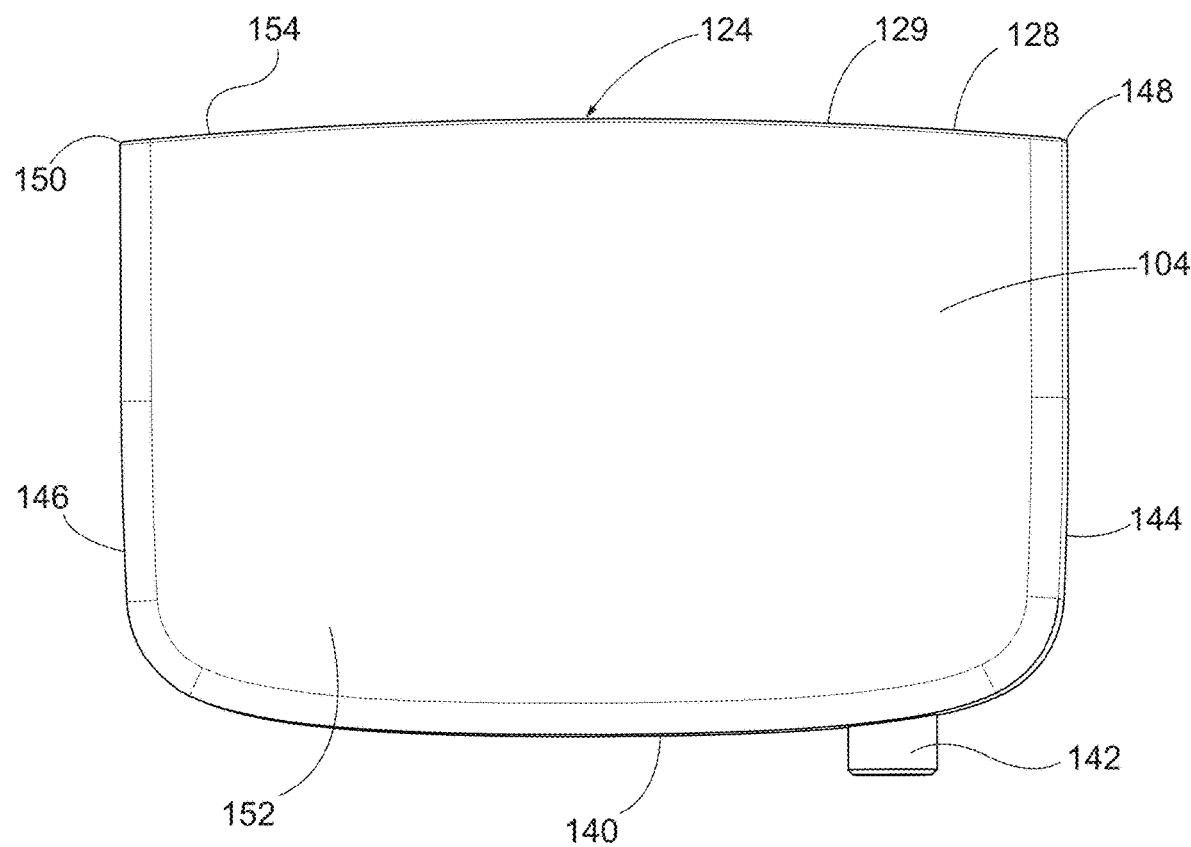
FIG. 2 is a front elevation view of a reservoir for the oral irrigator.

The reservoir 104 stores fluid, such as water, mouthwash, etc., for use with the oral irrigator 100. FIG. 2 is a front elevation view of the reservoir 104. The reservoir 104 is generally rectangular in shape and includes a front wall 152, rear wall 154, bottom wall 140, and two sidewalls 144, 144. The top end of the reservoir 104 is open and each of the front, rear, and side walls include a top edge 128, 129, 148, 150 at the top end of the reservoir 104. In one embodiment, the top edges 128, 129 of the front and rear walls 152, 154 vary in height along their length and curve upward toward a center of the reservoir 104. In other words, the front and rear walls 152, 154 have an increased height toward the center as compared to the edges. In this manner, the top end of the reservoir 104 bows or arcs upward in the middle and downward toward each of the sidewalls 144, 146.

Each of the walls is interconnected to define a reservoir compartment 124 for holding fluid. In some embodiments, the edges interconnecting the front wall 152, rear wall 154, bottom wall 140, and sidewalls 144, 146 are curved to define a soft angle, rather than a right angle that would define a sharp edge. This curvature is not only aesthetically pleasing, but also allows the reservoir 104 and the oral irrigator 100 to slide into and out of a packaging or container as the edges will not snag on the material and also will distribute impact forces more evenly across the reservoir 104.

The reservoir compartment 124 is dimensioned and shaped not only to hold a desired amount of fluid, but also to correspond to the shape and dimensions of the base unit 102. In particular, the reservoir compartment 124 is shaped such that the base unit 102 can fit easily within the reservoir compartment 124. A reservoir port 142 extends downward from the bottom wall 140 and is fluidly connected to the reservoir compartment 124 via an aperture defined through the bottom wall 140.

Base

Figure 3A:
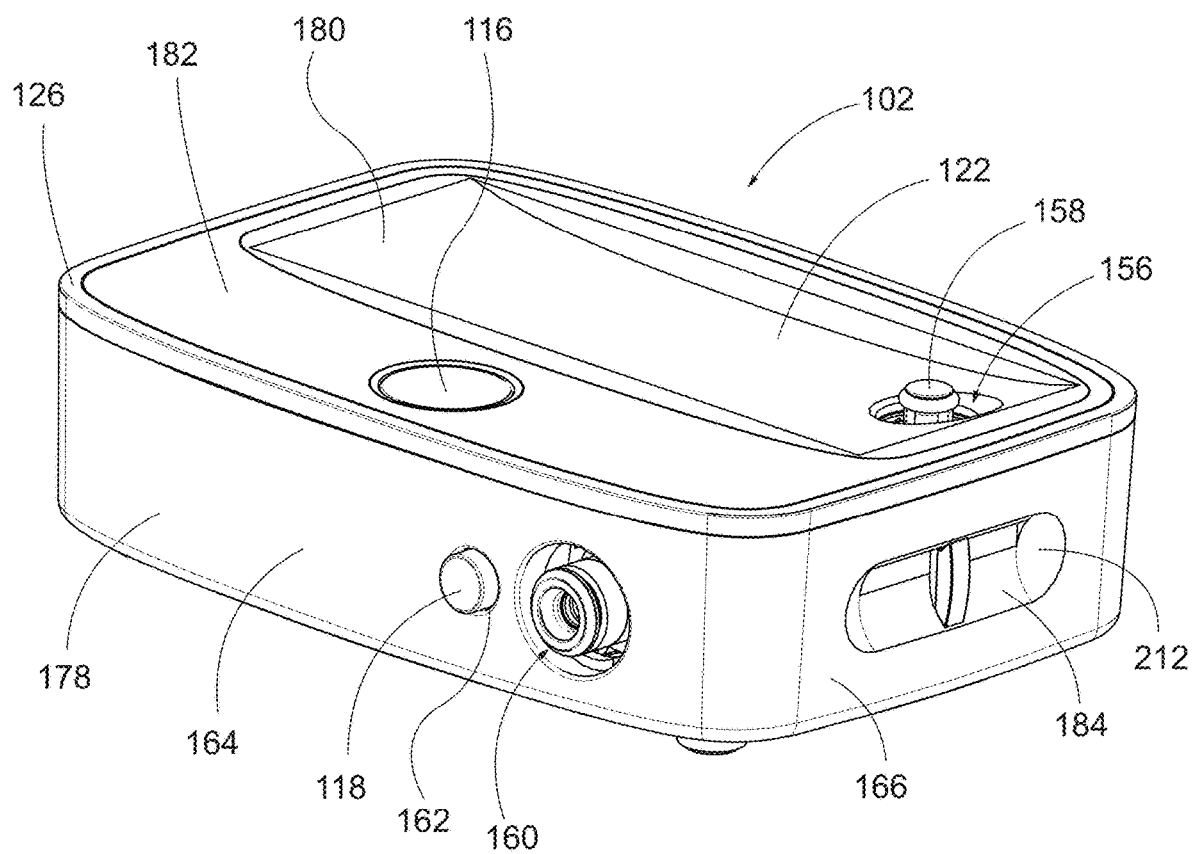
FIG. 3A is a front isometric view of a base for the oral irrigator.
Figure 3B:
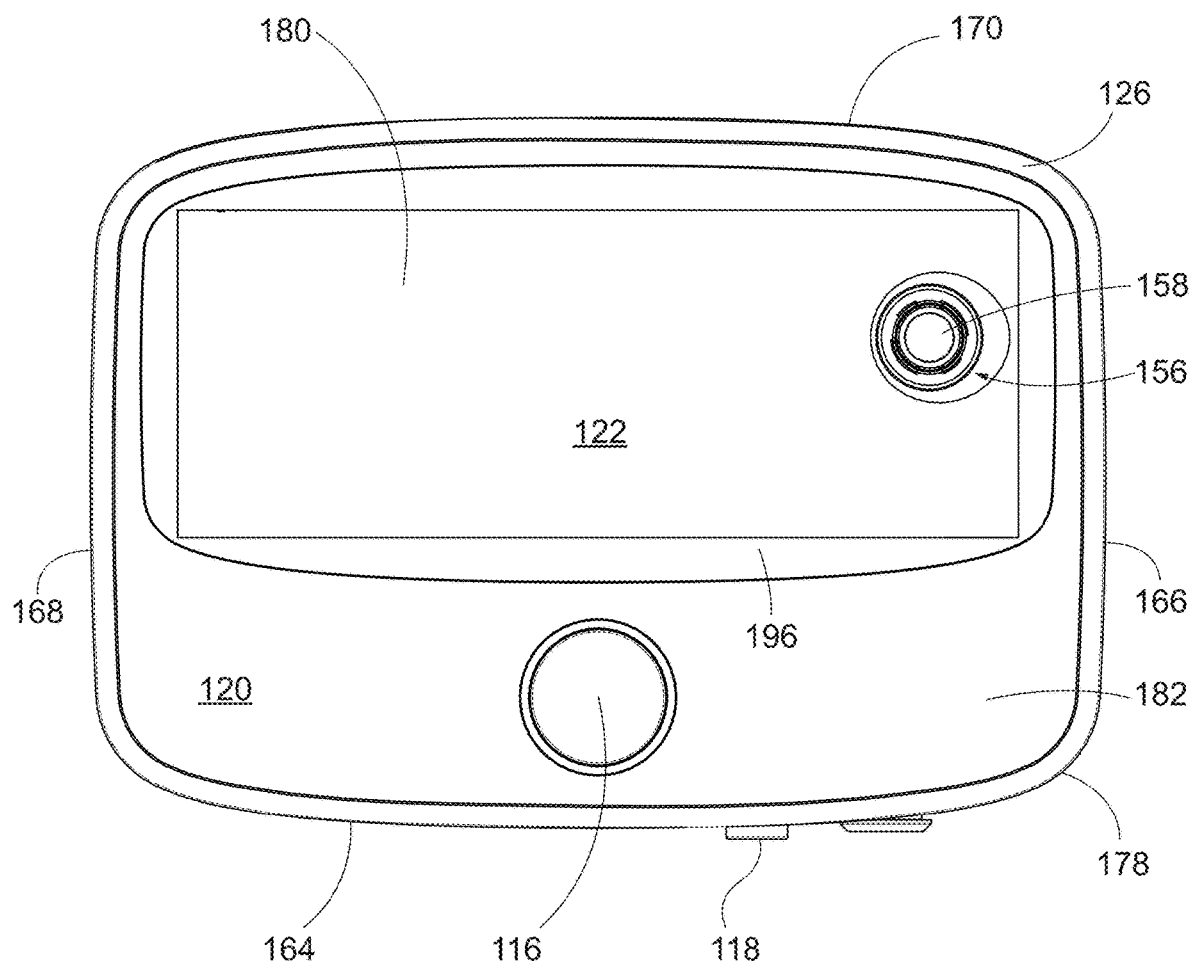
FIG. 3B is a top plan view of the base of FIG. 3A.
Figure 4:
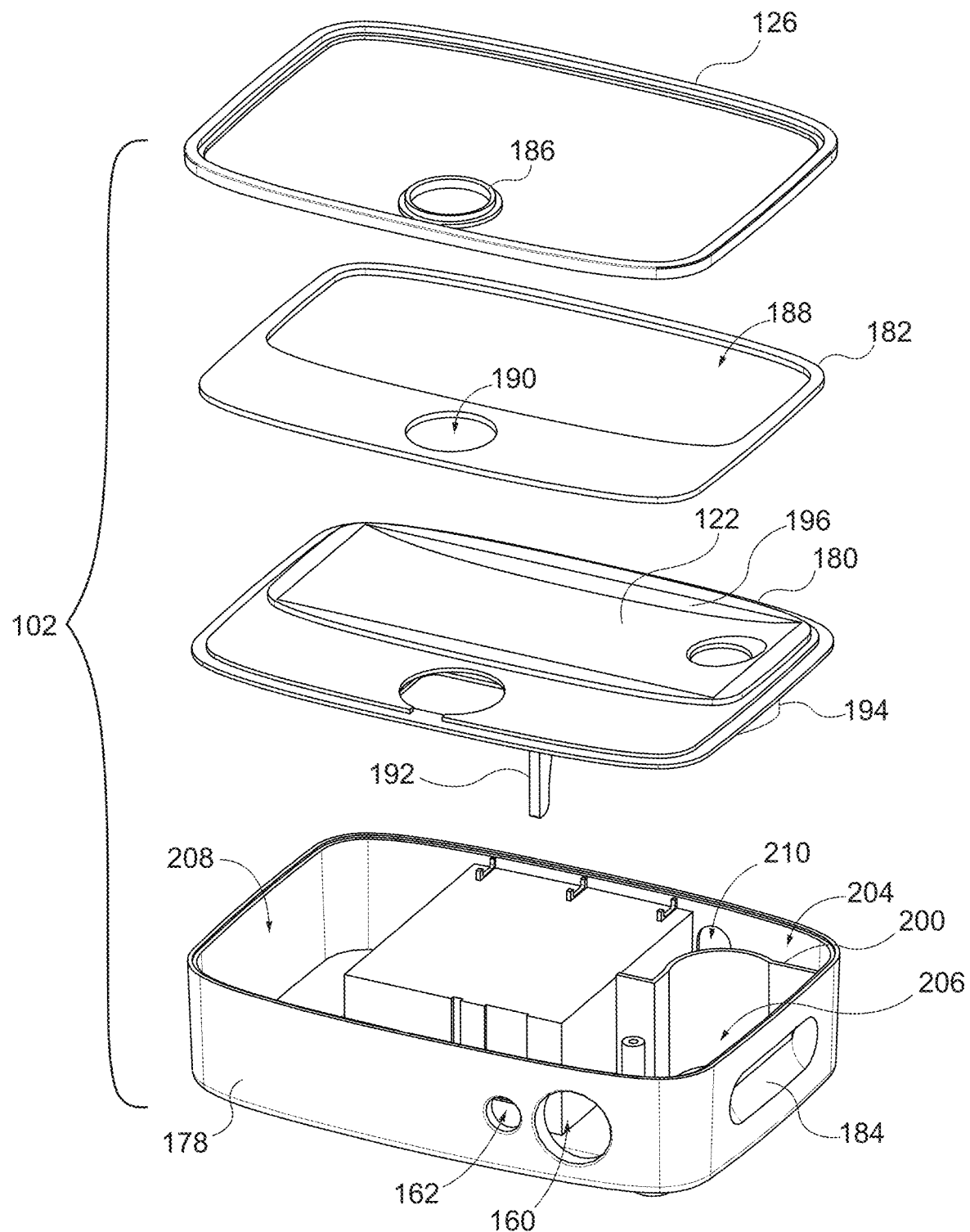
FIG. 4 is an exploded view of the base of FIG. 3A.
Figure 5:
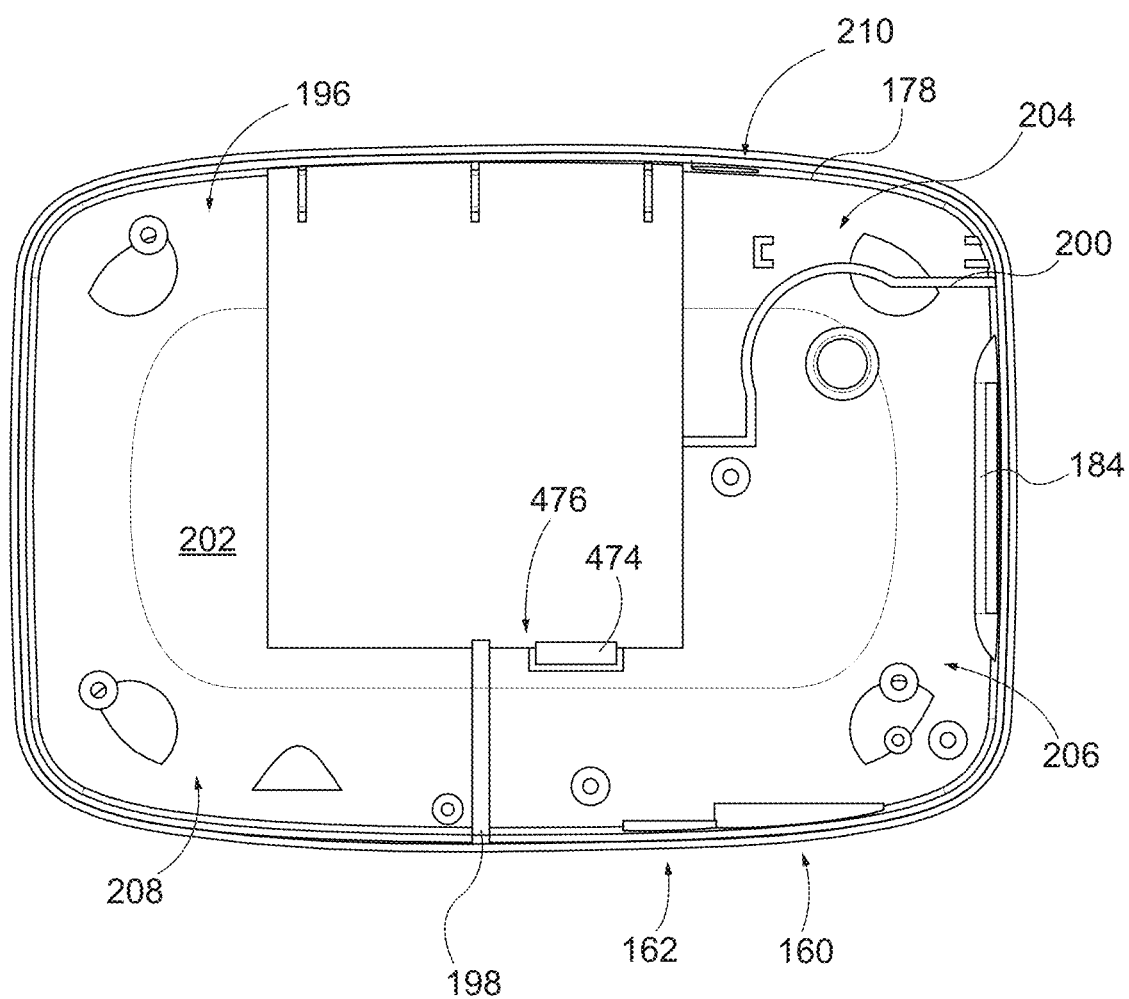
FIG. 5 is a top plan view of a lower housing for the base.

The base 102 supports the reservoir 104 and encloses the pumping and operating assemblies of the oral irrigator 100. FIGS. 3A-3D illustrate various views of the base 102 with the reservoir and the power assembly hidden. FIG. 3D differs from FIG. 3B in that a portion of the hose connector 112 is shown. FIG. 4 is an exploded view of the base. FIG. 5 is a top plan view of a lower housing of the base 102. With reference to FIGS. 3A-4, the base 102 includes a lower housing 178, an upper housing 180, a face plate 182, and a trim ring 126, each of which interconnect together.

The trim ring 126 is an accent ring of material and includes a button ring 186 connected thereto. In many embodiments the trim ring 126 is a different material from the other components of the base unit to provide an aesthetically pleasing appearance. The trim ring 126 helps to secure the various base components together and may include ribs, flanges, and other fastening elements to press fit or otherwise connect to the other components.

With reference to FIG. 4, the face plate 182 defines the top surface 120 of the base 102 and assists in enclosing the interior compartments of the base 102. The face plate 182 may include cutouts, such as the upper housing aperture 188 and button aperture 190 for exposing select components of the oral irrigator 100, but may be differently configured as desired. In some embodiments, the face plate 182 may be a transparent material, such as transparent plastic, and include a paint or coating on the interior surface thereof. As the painted color is beneath the top outer surface, the outer surface of the transparent face plate 182 has a high gloss appearance. Additionally because the painted color is below the outer surface it will be less exposed to environmental wear and tear and thus last longer and be less likely to chip.

The upper housing 180 forms the sealing surface to substantially enclose the internal compartment of the lower housing 178. The upper housing 180 may also define a support surface for the reservoir 104 when the reservoir 104 is seated on top of the base 102. For example, the upper housing 180 may include an engagement surface 122 having a concave shape that bows downward toward the center and raises upward toward the sidewalls of the upper housing 180. A lip 196 may surround the perimeter of the engagement surface 122 and help to align the reservoir 104 with respect to the engagement surface 122, as well as prevent fluids from exiting the engagement surface 122 (such as those that leak from the reservoir 104 or down the sides of the reservoir).

The upper housing 180 may also include a sealing wall 192 and a port wall 194 extending downward from a bottom surface. The sealing wall 192 may be a substantially planar member positioned toward the front middle end of the upper housing 180. The port wall 194 may be a generally cylindrically shaped wall positioned near the rear end of the upper housing 180 and configured to receive elements for connecting the reservoir 104 to the base 102, such as valves and connectors.

With reference to FIGS. 3A-3D, and 5, the lower housing 178 of the base unit 102 includes a front wall 164, a back wall 170, two sidewalls 166, 168, and a bottom wall 202. The combination of the walls 164, 166, 168, 170, 202 defines a base cavity 196 in which the pump assembly, pressure assembly, drive assembly, and other components are received and as such may be varied to accommodate those components as desired. In one embodiment, the lower housing 178 includes a power block cavity 174 defined in the back wall 170 (see FIG. 3C). The power block cavity 174 is configured to receive the power assembly 134, which can be removed from the lower housing 178 as discussed below. In these embodiments, the lower housing 178 may include alignment and securing features, such as alignment ribs 176 extending along a length of the walls defining the power block cavity 174. The alignment ribs 176 are configured to engage corresponding grooves on the power assembly 134.

With reference to FIGS. 4 and 5, the lower housing 178 may also include a groove 198 defined on the upper surface of the bottom wall 202. A contoured sealing wall 200 extends upward from the bottom wall 202 and is configured to correspond to a shape of the reservoir valve connector and pressure actuator. The sealing wall 200 and the groove 198 are sealing components that assist in defining dry compartments 204, 208 and a wet compartment 206. The dry compartments 204, 208 are sealed from the external environment, as well as the components that are fluidly connected to the reservoir 104 to reduce damage to components stored therein.

With reference to FIGS. 3A and 4, the lower housing 178 also includes a hose aperture 160, a button aperture 162, a slide recess 184, and a power connector aperture 210 for connecting elements to the base unit 102. The hose aperture 160 and the button aperture 162 are both defined through the front wall 164 and extend into the wet compartment 206. Similarly, the slide recess 184 defines a recessed track on sidewall 166 and includes openings 212 (see FIG. 3A) for connecting an actuator to components stored within the lower housing 178. The power connector aperture 210 is defined through the back wall 170 and extends into the dry compartment 204.

Additionally, with reference to FIG. 5, in some embodiments, the lower housing 178 includes a pocket 476 defined in the back wall 170 in the power block cavity 174. The pocket 476 is defined in the internal compartment of the lower housing 178 and is configured to receive a magnet 474. As will be discussed in more detail below, the magnet 474 is configured to interact with the power assembly to secure it in position.

Operating Components

Figure 6A:
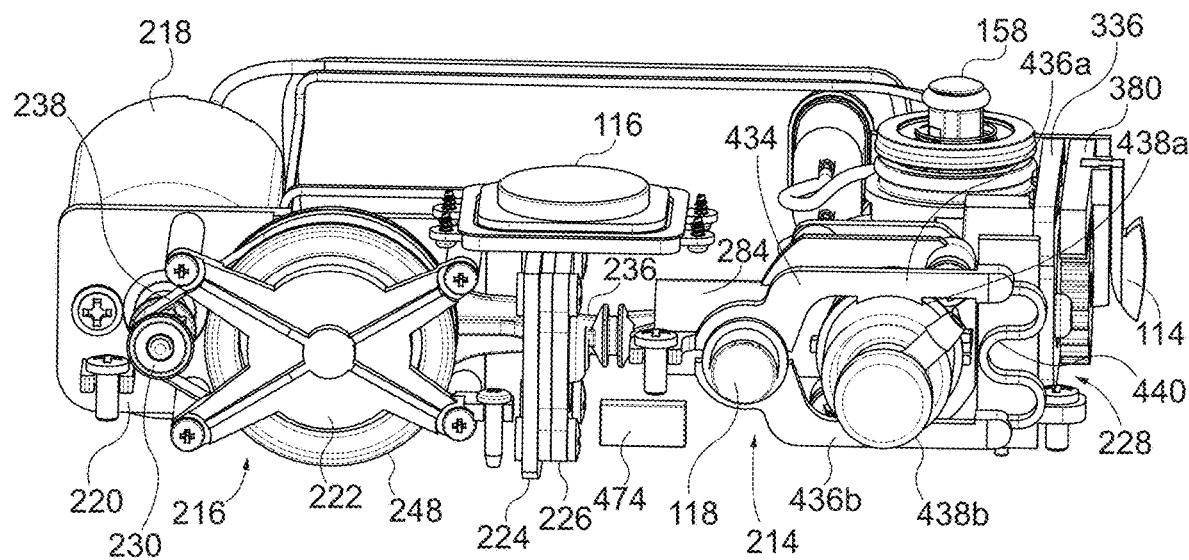
FIG. 6A is a front elevation view of operating components for the oral irrigator as arranged in the base.
Figure 6B:
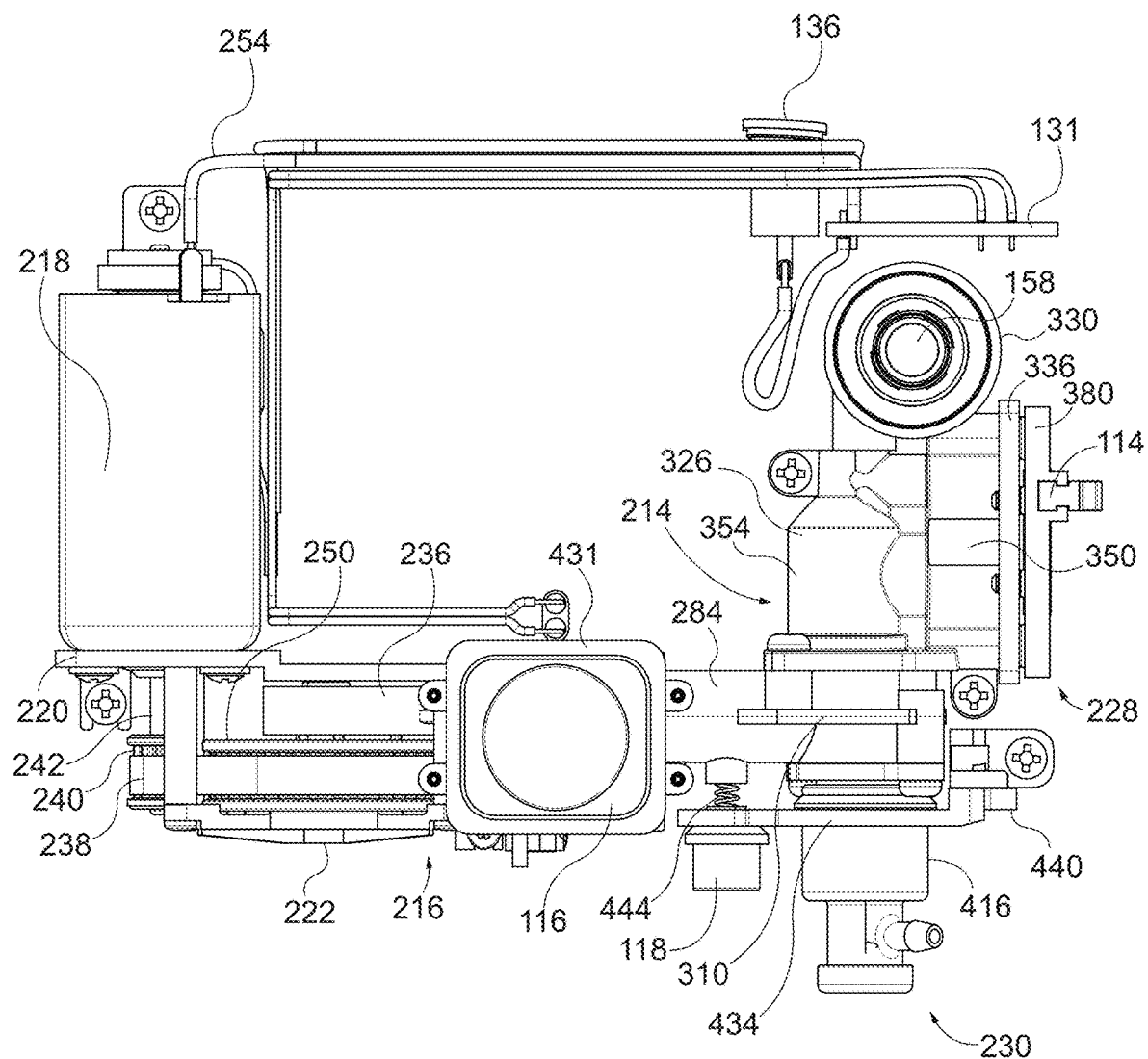
FIG. 6B is a top plan view of the operating components of FIG. 6A illustrating their layout in the base.

The operating components of the oral irrigator 100 will now be discussed in more detail. FIGS. 6A and 6B illustrate various views of the main operating components of the oral irrigator with the various housings removed to better illustrate the internal components. As shown in FIGS. 6A and 6B, the oral irrigator 100 may include a drive assembly 216, a pump assembly 214, a pressure assembly 228, and a connection assembly 230, each of which will be discussed, in turn, below. Each of the assemblies may be interconnected together and received within respective compartments within the lower housing 178.

Mechanical Power Transmission Assembly

Figure 7A:
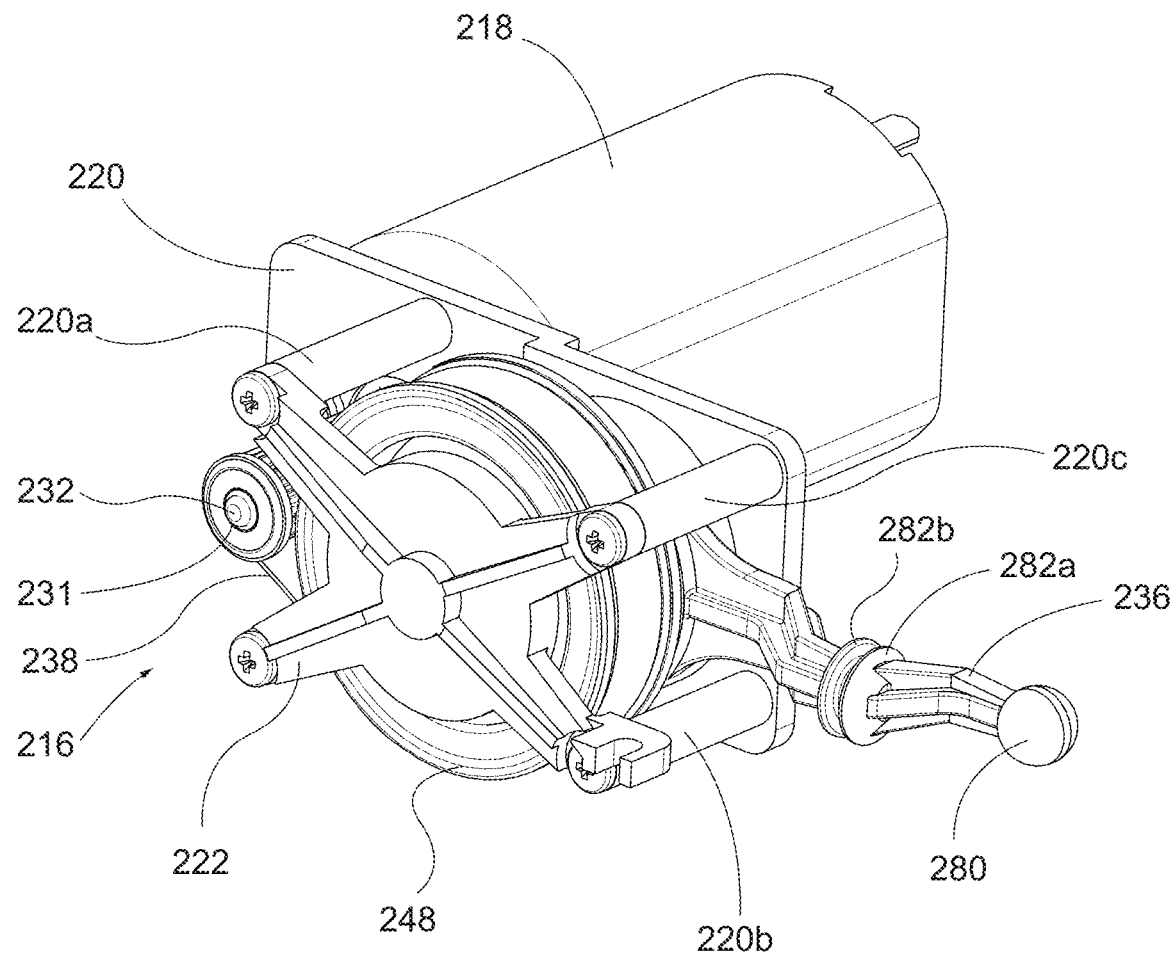
FIG. 7A is a front isometric view of a drive assembly for the oral irrigator.
Figure 7B:
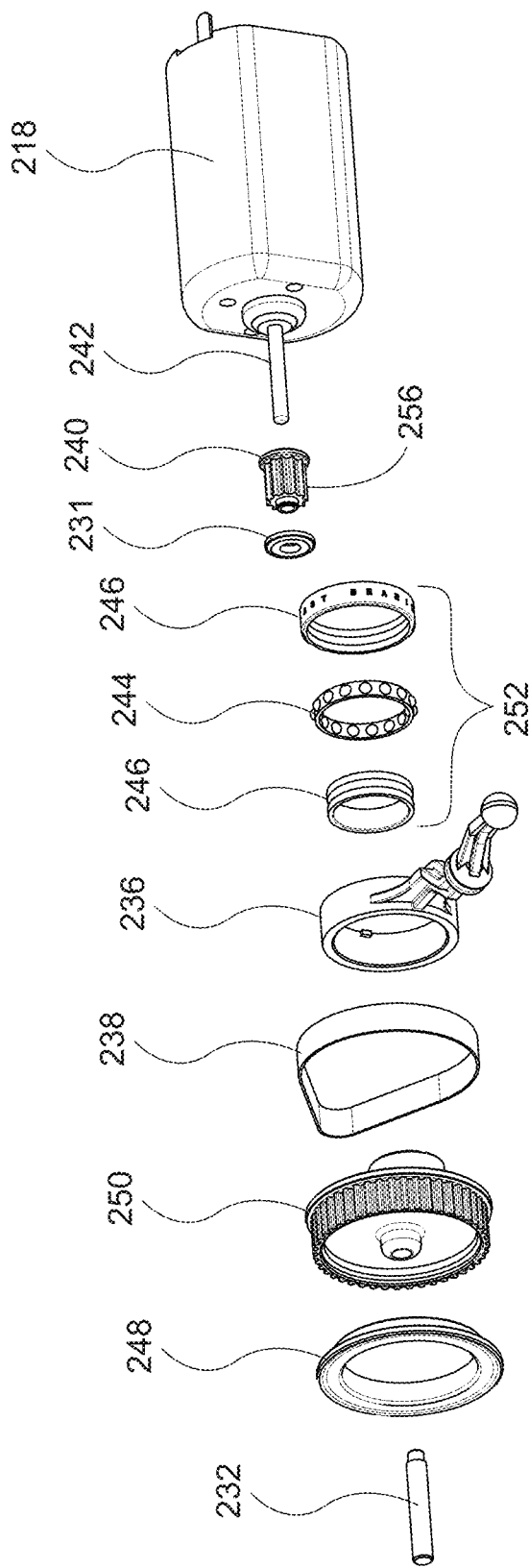
FIG. 7B is an exploded view of the drive assembly.

The drive assembly 216 converts rotational movement from a motor into translational mechanical movement that drives the pump assembly 214. FIG. 7A illustrates a front isometric view of the drive assembly 216. FIG. 7B illustrates an exploded view of the drive assembly 216. The drive assembly 216 includes a motor 218, a pinion pulley 240, a driven pulley 250, a belt 238, a ball bearing race 252 having inner and outer rings encompassing a ball bearing ring 244, belt securing flanges 231, 248, a gear pin 232, and a connecting rod 236. The motor 218 includes a drive shaft 242 and, as shown in FIG. 6B, is electrically connected to the male power connector socket 136 forming a power inlet of the base 102 via wires 254.

The motor 218 may be substantially any type of device that converts electricity into motion. In one embodiment, the motor 218 includes a signal conditioner such as a varistor.

The pinion pulley 240 is received around or otherwise secured to the drive shaft 242 such that the pinion pulley 240 rotates with the drive shaft 242. The pinion pulley 240 optionally may include a plurality of teeth 256 or grip elements for enhancing a frictional engagement with the belt 238. However, depending on the configuration of the belt 238, the pinion pulley may not include teeth or may include other engagement features.

Figure 8A:
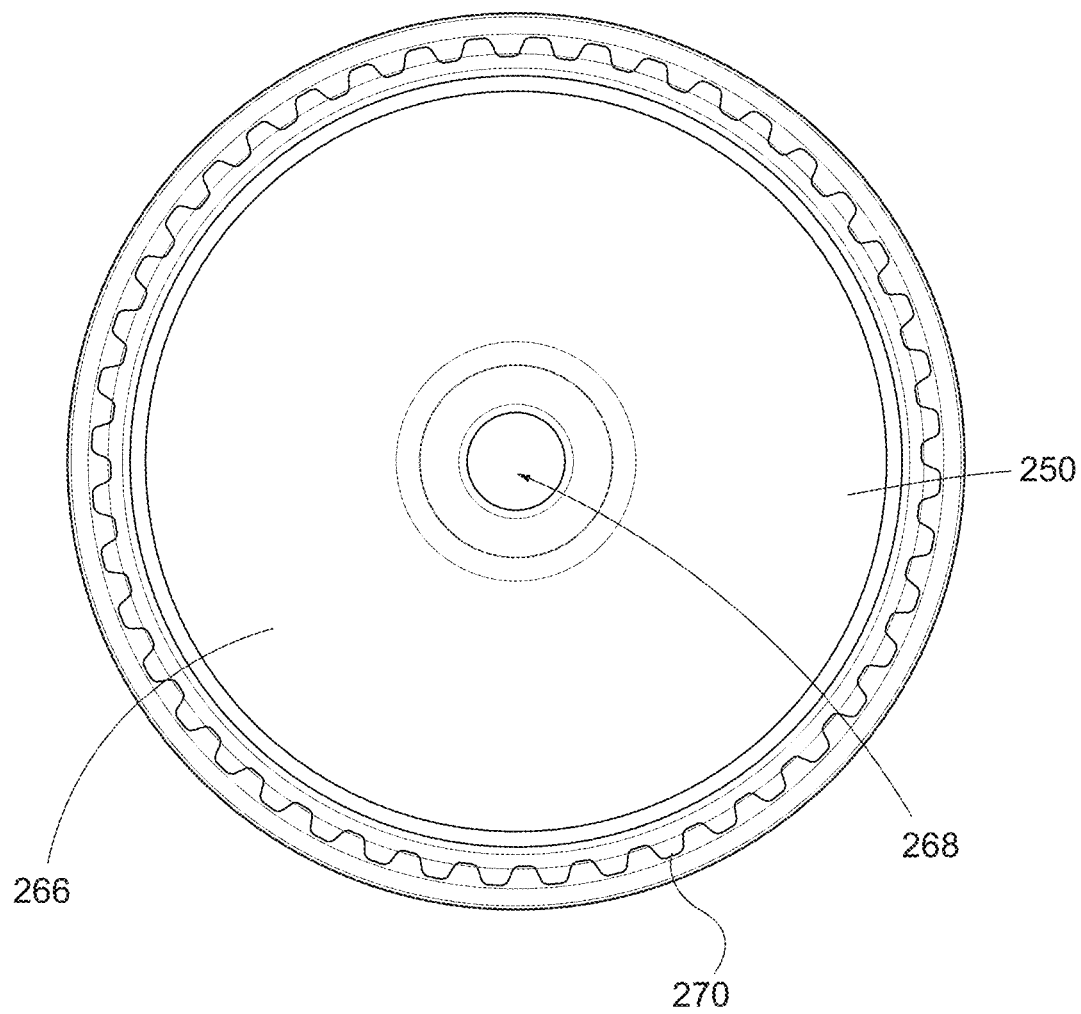
FIG. 8A is first side elevation view of a driven pulley for the drive assembly.
Figure 8B:
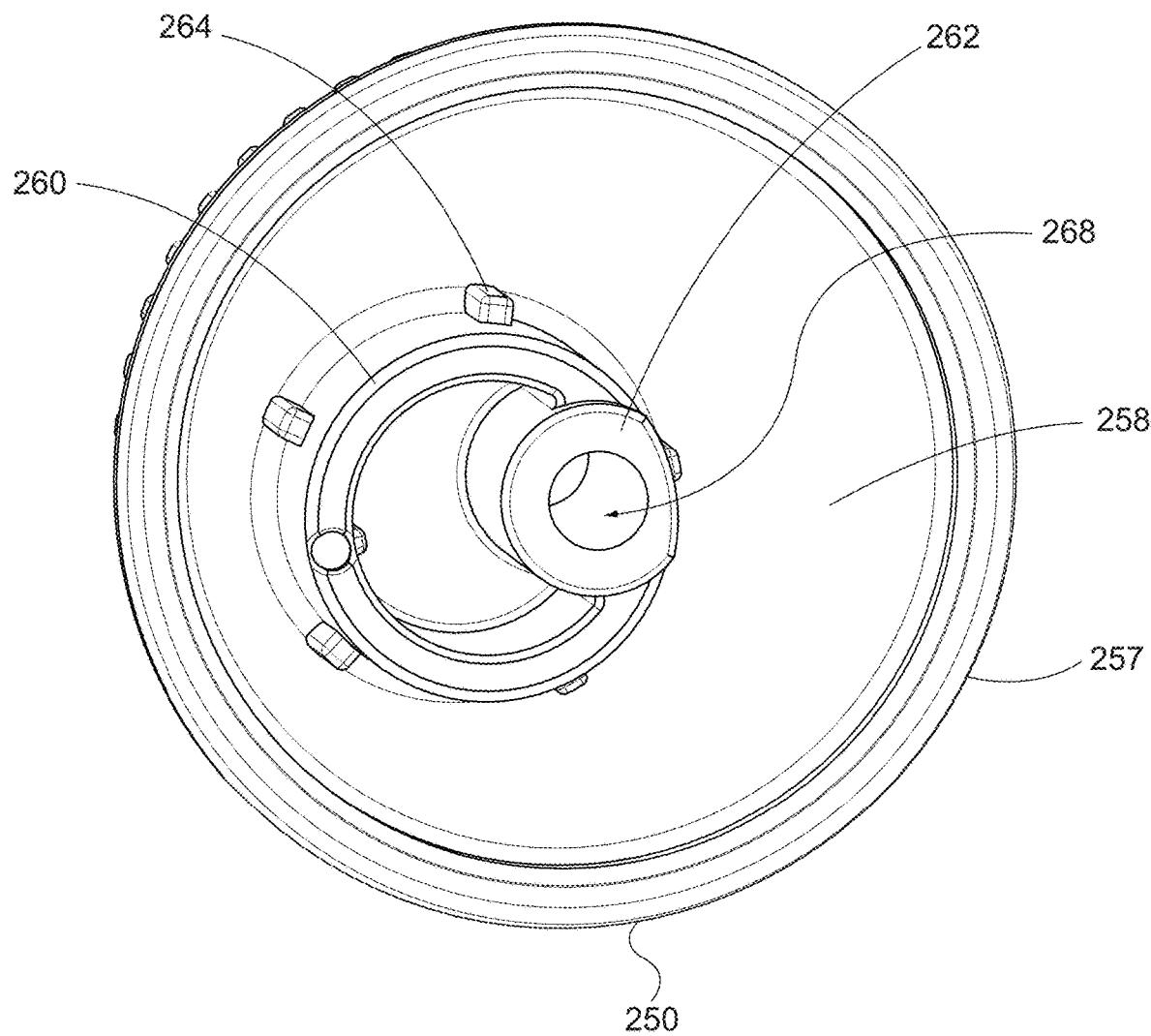
FIG. 8B is a side isometric view of the driven pulley for the drive assembly.

FIGS. 8A and 8B illustrate various views of the driven pulley 250. The driven pulley 250 is driven by the pinion pulley 240 via the belt 238. The driven pulley 250 may be a relatively cylindrically shaped disc having a first surface or side 258 and a second surface or side 266. In one embodiment, the driven pulley 250 includes a plurality of teeth 270 or other engagement elements that extend radially outward from the second surface 266 and are oriented to face outward away from a center of the pulley 250. A pin aperture 268 is defined through the driven pulley 250 and extends between the first and second surfaces 258, 266.

With reference to FIG. 8B, the driven pulley 250 also includes an engagement boss 260 that extends outward from the first surface 258. The engagement boss 260 may be formed as a cylindrical protrusion and may include one or more ribs 264 extending lengthwise on an outer surface thereof. In many embodiments, the engagement boss 260 is offset from a center axis of the driven pulley 250. The bearing race 252 (see FIG. 7B) may seat around the engagement boss 260 and is held in place by the ribs 264. For example, the pin aperture 268 is typically aligned with the center axis of the driven pulley 250 and the engagement boss 260 is offset relative thereto to form an eccentric post. As the engagement boss 260 extends away from the first surface 258, in some embodiments, a pin structure 262 may be arranged within the engagement boss 260 to increase the length of the pin aperture 268, extending it through the height of the engagement boss 260. In some embodiments, the pin structure 262 may be longer than the height of the engagement boss 260.

With continued reference to FIG. 8B, the driven pulley 250 may also include a lip 257 or edge that defines a perimeter of the first surface 258. The lip 257 may extend outward and upward from the first surface 258 such that the first surface 258 is partially recessed below the edge 257.

With reference again to FIG. 7B, the flanges 230, 248 are used for securing the belt 238 to the pulleys 240, 250 and as such may be configured to mate with and connect to the respective pulley. In some examples, the flanges 230, 248 may be secured to the pulleys 240, 250 using various attachment methods, such as ultrasonic welding, adhesive, riveting, etc. In some examples, the flanges 230, 248 may be integrated into each of the pulleys 240, 250.

The belt 238 transmits rotation from the pinion pulley 240 to the driven pulley 250. The belt 238 may include a plurality of teeth for engaging the pinion pulley 240 and the driven pulley 250. In one embodiment, the belt 238 is an MXL-type timing belt with a pitch of 0.08" and a 3/16" width. However, many other types of belts with different pitch length and widths may be used, such as additional synchronous belts with other timing profiles such as XL and L, or HTD type with pitches such as 3 mm, 5 mm, or 8 mm, GT type with pitches such as 2 mm, 3 mm, 5 mm, 8 mm pitches, chevron style synchronous belts; round belts; flat belts; elastic belts; and V-shaped belts.

Figure 9A:
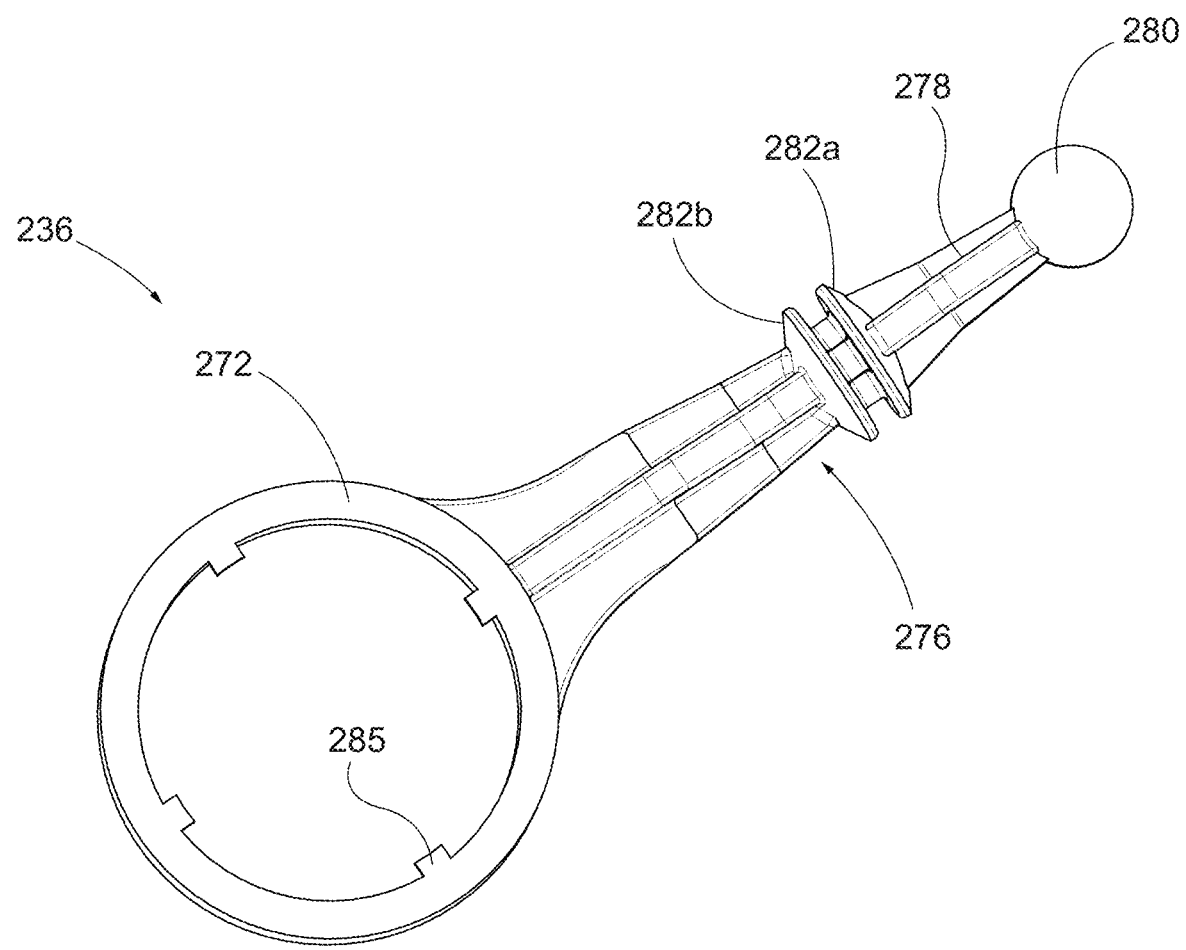
FIG. 9A is a top plan view of a connecting rod for the drive assembly.
Figure 9B:
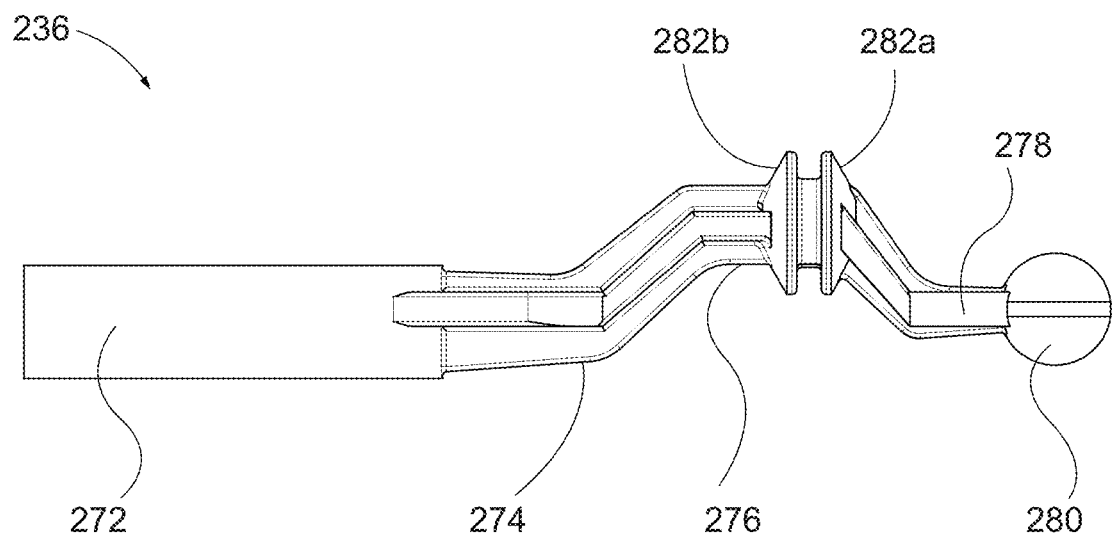
FIG. 9B is a side elevation view of the connecting rod.

FIG. 9A is a top plan view of the connecting rod 236. FIG. 9B is a side elevation view of the connecting rod 236. As shown in FIGS. 9A and 9B, the connecting rod 236 includes a connecting end 272 defining a cylindrical ring having a plurality of tabs 285 extending inward from an interior surface. The connecting end 272 is shaped and dimensioned to be received around the bearing race 252 and thereby around the engagement boss 260 of the driven pulley 250. The tabs 285 secure the connecting end 272 to the outer surface of the bearing race 252 (see FIG. 7B) thereby allowing the engagement boss 260 to rotate within the cylindrical ring of the connecting end 272. An arm 274 extends from the connecting end 272. The arm 274 is generally straight, but includes an angled bend 276 or elbow in a middle portion thereof. The angled bend 276 assists in allowing the drive assembly 216 to fit within the lower housing and maintain the reduced form factor of the oral irrigator 100. Additionally, the bend allows the connecting rod 236 to pass through and center on a seal between wet and dry compartments. From the angled bend 276, the arm 274 transitions to a terminal end 278 having a ball 280.

Figure 10:
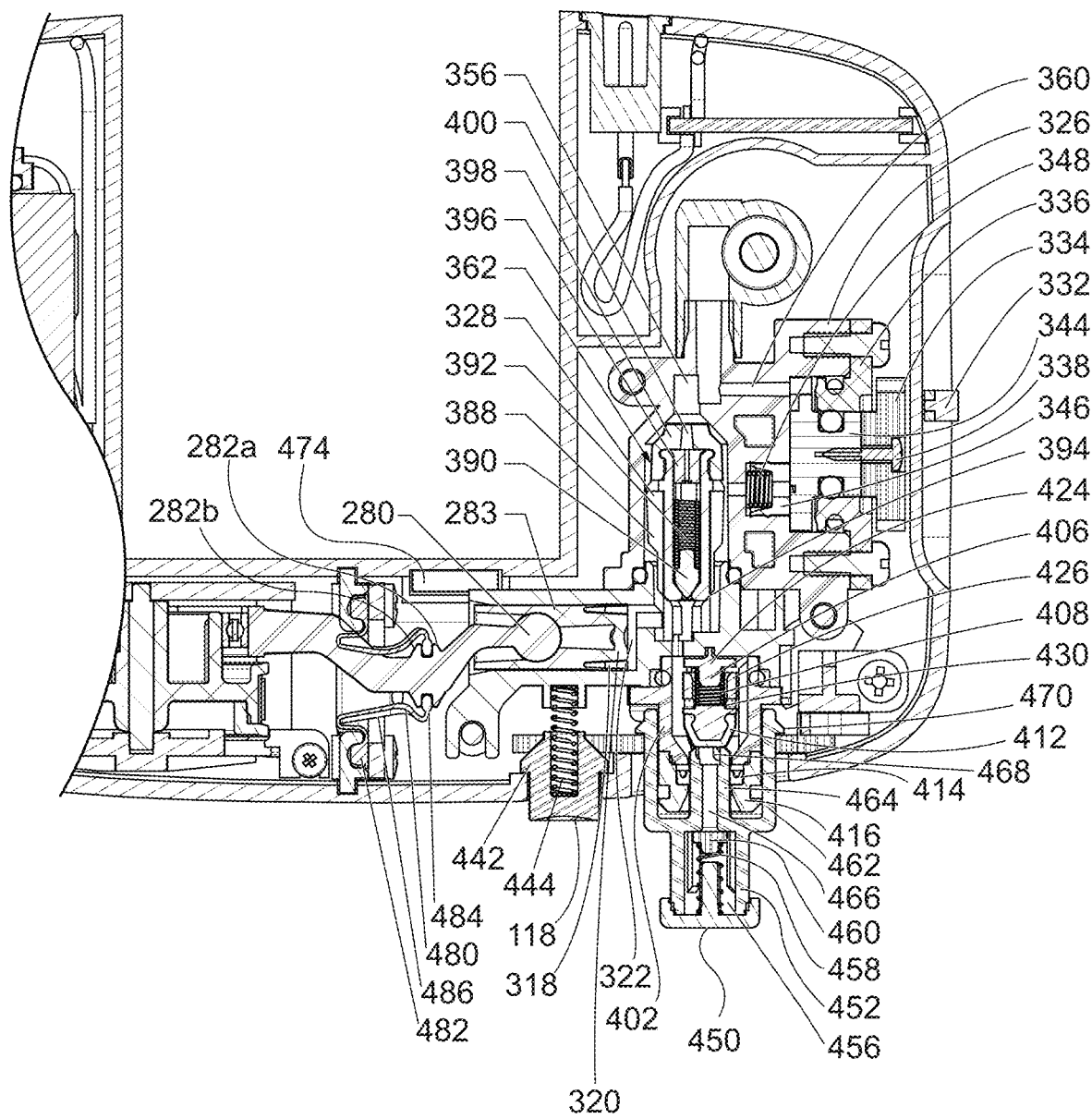
FIG. 10 is an enlarged view of the cross-sectional view of FIG. 6C.

As shown in FIG. 10, the drive assembly 216 also includes a diaphragm seal 480 having a seal top surface 484 and a rod aperture through a center thereof. The seal top surface 484 extends radially outward from the rod aperture and then downward at an angle to define a flexible skirt 486. The skirt 486 may be conical or frustum shaped and define a bellows. The skirt 486 is flexible and configured to resiliently deform and return to its original shape. A crease at the bottom of the skirt 486 varies as the seal is deformed. A beaded flange 482 extends radially outward from a top end of the crease. The flange 482 includes a flat top surface and a convexly curved bottom surface.

Pump Assembly

Figure 6C:
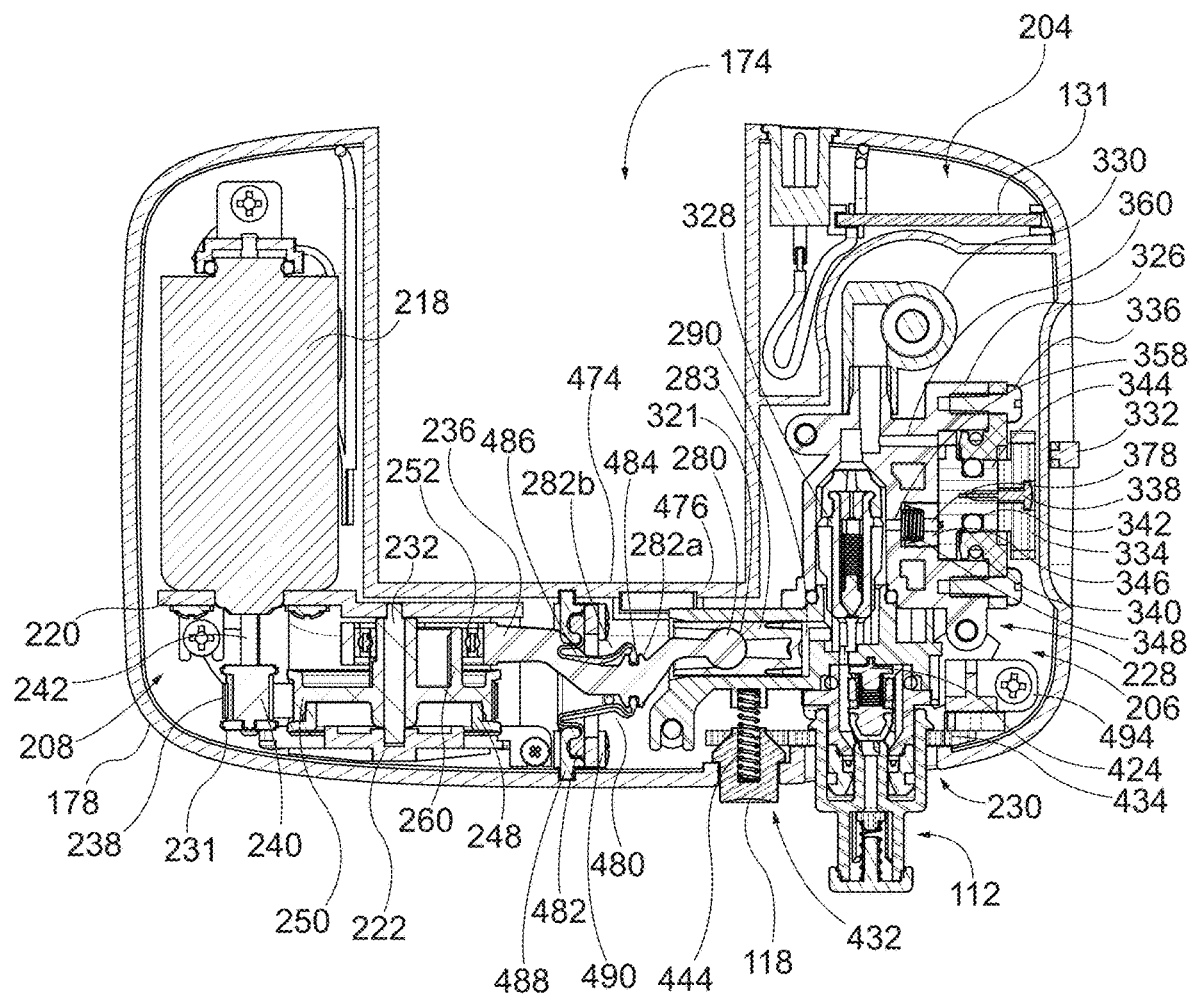
FIG. 6C is a cross-sectional view of the oral irrigator taken along line 6C-6C in FIG. 1C.

With reference to FIG. 10, which is an enlarged view of FIG. 6C, the pump assembly 214 includes a piston 283 that is driven by the drive assembly 216 and a pump body 284. The piston 283 is generally cylindrical and has on its top surface an annular flange 318 and an interior pedestal 320. An annular valley is defined between the annular flange 318 and interior pedestal 320. A curved interior surface 321 on the interior of the piston is configured to receiving the ball 280 of the connecting rod 236 in order to form a ball joint.

Figure 11A:
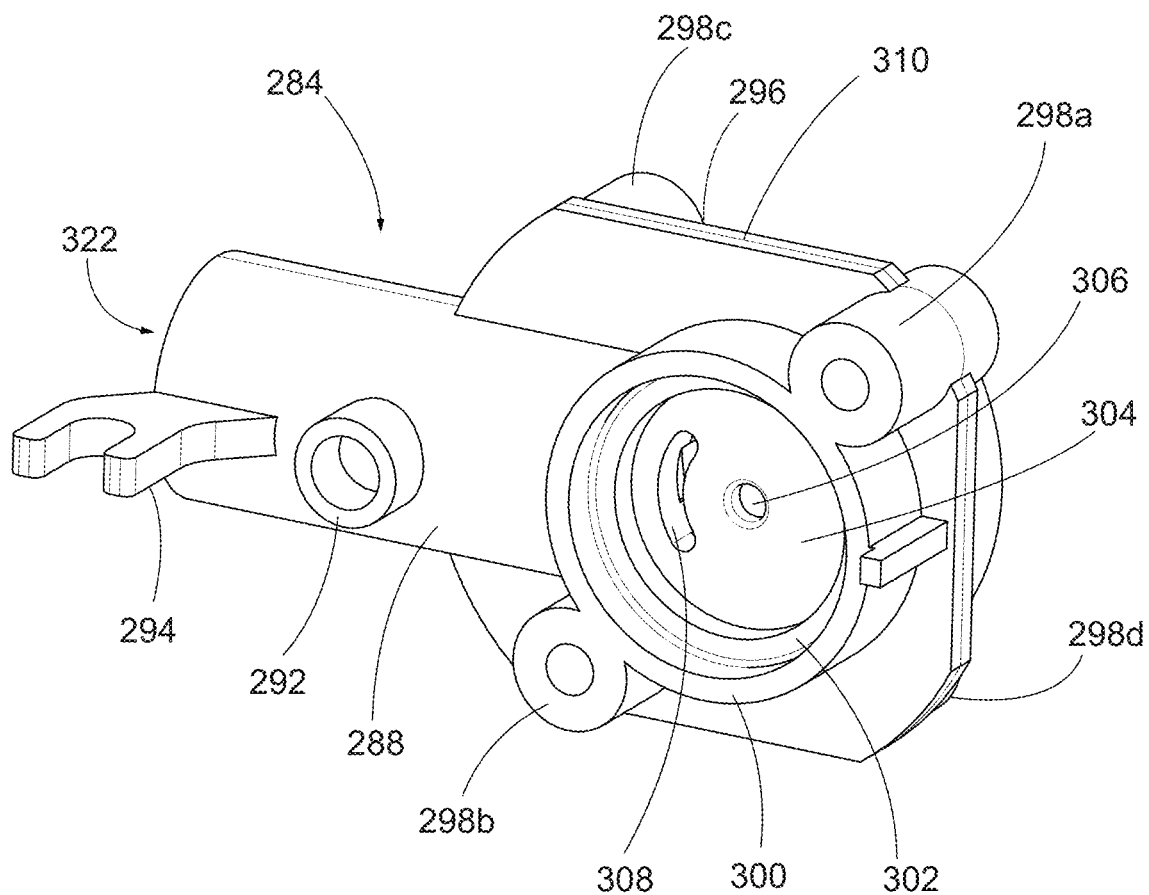
FIG. 11A is a front isometric view of a pump housing for a pump assembly.
Figure 11B:
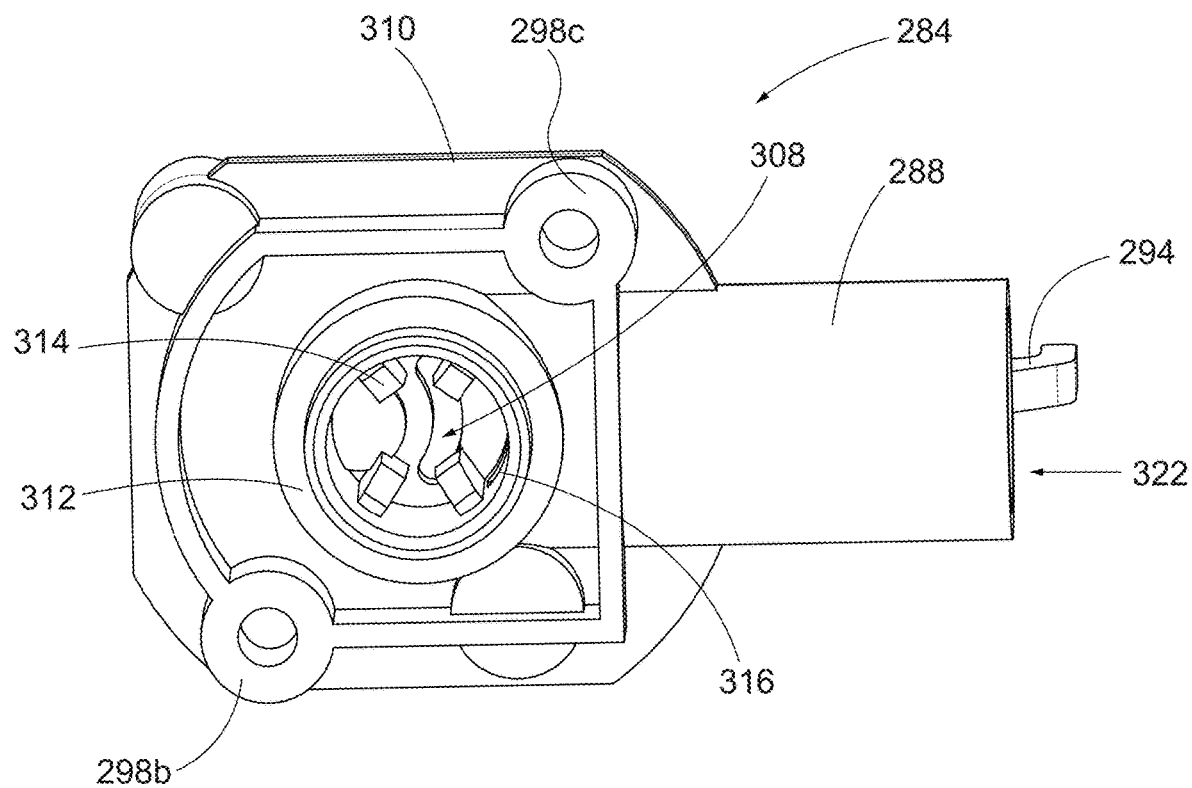
FIG. 11B is a rear isometric view of the pump housing of FIG. 11A.

FIGS. 11A and 11B illustrate front and rear isometric views of the pump body 284. The pump body 284 includes a pump wall 288 defining a pump chamber 322 therein. A securing bracket 294 is connected to a side surface of the pump wall 288 and is configured to receive a fastening element. Additionally, a spring wall or post 292 extends from the same side surface as the securing bracket 294 for receiving components of the eject button, discussed in more detail below. A hose interface 296 is connected to a first end of the pump wall 288 and includes a plate 310 having first and second sides with corresponding connection features for coupling the pump body 284 to internal and external valves.

In particular, with reference to FIG. 11A, a valve housing 300 for interfacing with the hose connector 112 extends from a first side of the plate 310. The valve housing 300 may be shaped as a cylindrical wall and include a ledge 302 extending concentrically within the valve housing 300 from the plate 310. The ledge 302 may be shorter than the valve housing 300 and terminate before an outer edge of the valve housing 300. The back wall 304 of the valve housing 300, which may form a portion of the first side of the plate 310, includes a pin recess 306 and a pump outlet 308. The pump outlet 308 is fluidly connected to the pump chamber 322.

With reference to FIG. 11B, the rear side of the plate 310 includes a tube 312 for interfacing with the pressure assembly 228 and corresponding valves. The tube 312 may include one or more prongs 314 extending from an interior surface thereof to engage with corresponding valve elements. A pump inlet 316 is defined as an aperture through the tube 312 and is fluidly connected to the tube 312 and the interior of the pump chamber 322.

Pressure Assembly

With reference again to FIGS. 6A and 6C, the pressure assembly 228 will now be discussed in more detail. The pressure assembly 228 allows a user to selectively adjust the pressure output by the oral irrigator 100. In one embodiment, the pressure assembly 228 includes a regulator housing 326, a dual valve assembly 328, and a pressure valve 344.

Figure 12A:
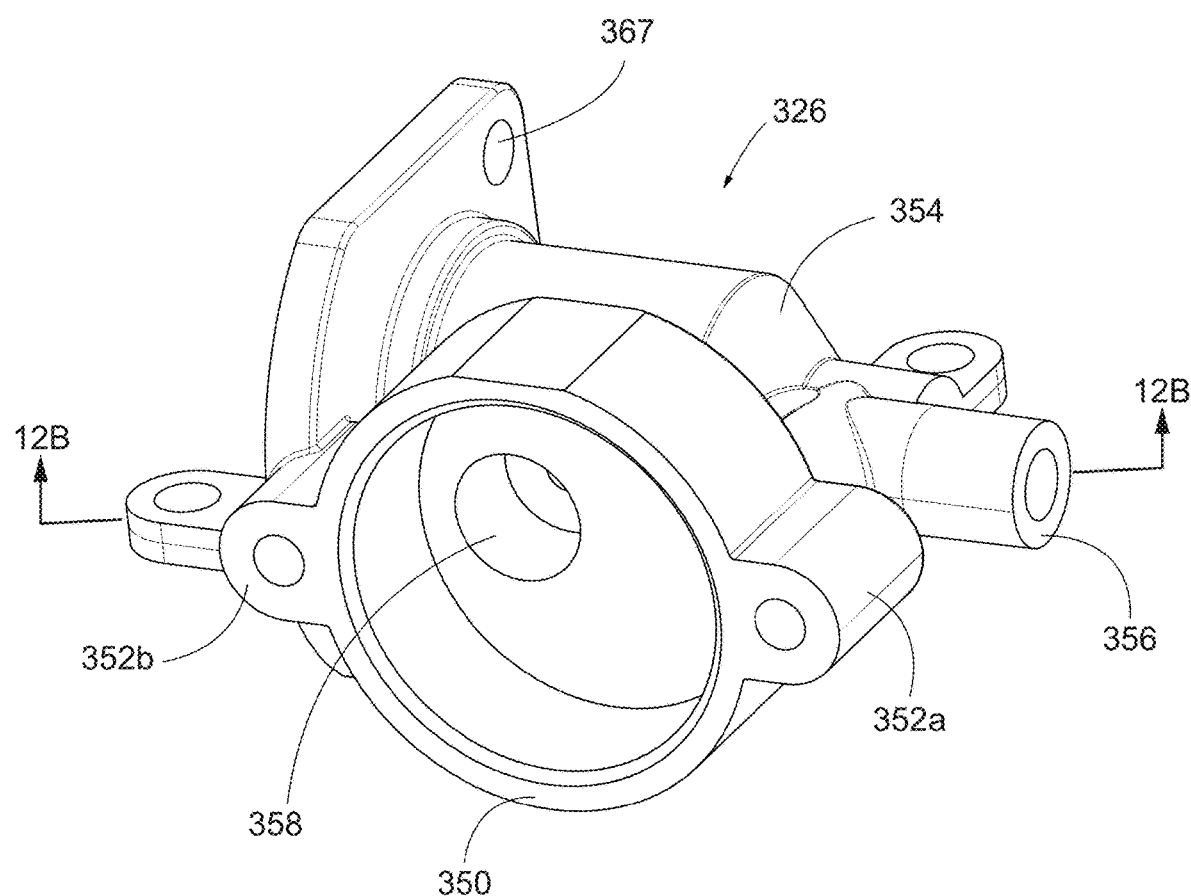
FIG. 12A is a front isometric view of a regulator housing for a pressure assembly.
Figure 12B:
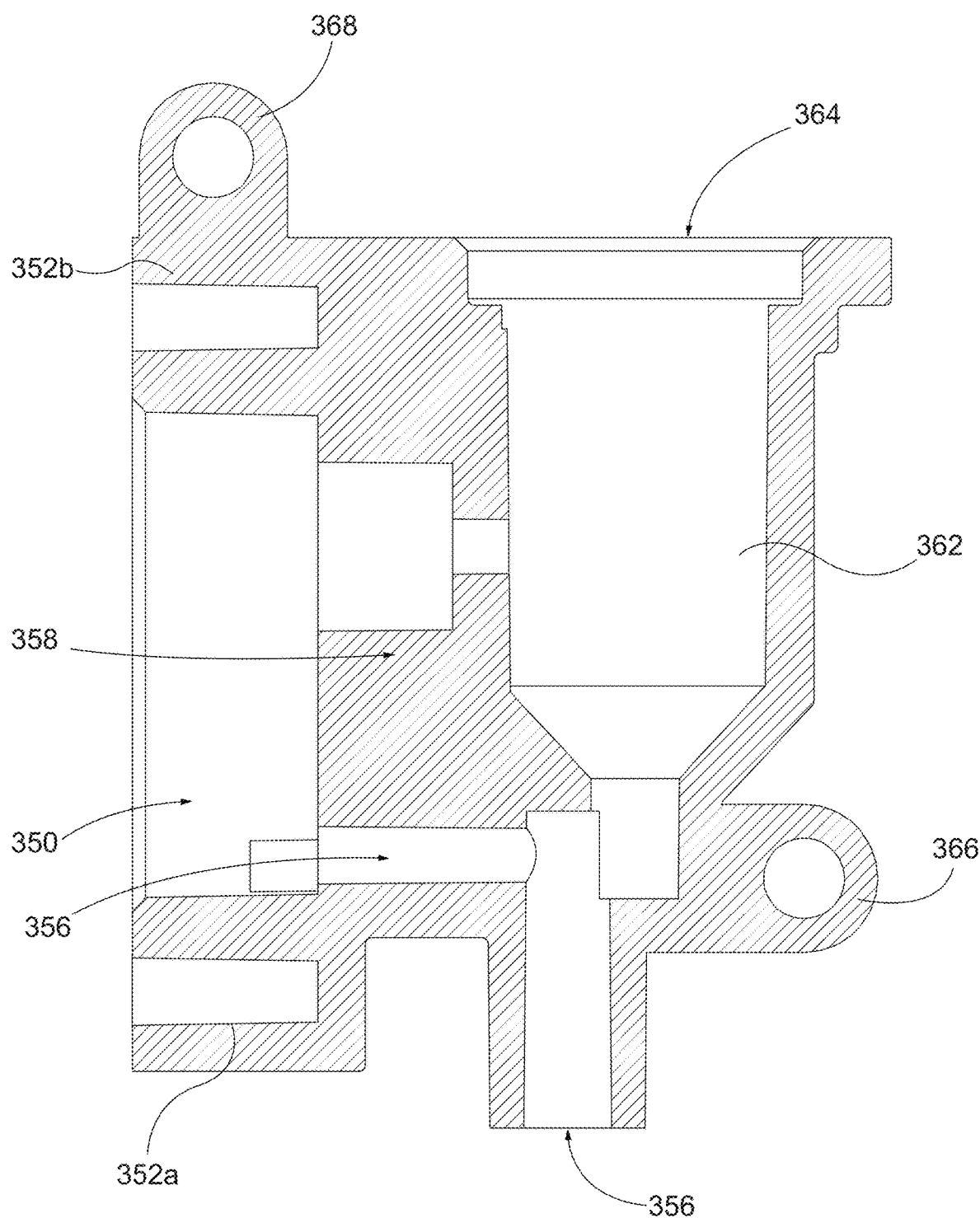
FIG. 12B is a cross-sectional view of the regulator housing taken along line 12B-12B of FIG. 12A.

FIGS. 12A and 12B illustrate an isometric view and a cross-sectional view, respectively, of the regulator housing 326. With reference to FIGS. 12A and 12B, the regulator housing 326 defines a body for receiving the pressure valve 344 and the dual valve assembly 328. Additionally, the regulator housing 326 defines a fluid flow path from the reservoir 104 to the pump assembly 214 and so, in some embodiments, may also form a part of the pump housing.

The regulator housing 326 includes a main body 354 that may have a generally cylindrical shape defining a main channel 362 therethrough. An inlet 356 is fluidly connected to the main channel 362 and extends from a first end of the main body 354. A regulator outlet 364 is defined on the opposite end of the main channel 362. A valve compartment 350 is defined on a side of the main body 354 and includes a cavity for receiving the pressure valve 344, two securing features 352a, 352b connected to either side of the compartment 350, a valve inlet 358 and a valve outlet 360. The valve inlet 358 is fluidly connected to the main channel 362 and the valve outlet 360 is fluidly connected to the housing inlet 356. In other words, fluid flows through the valve compartment 350 in the opposite direction it flows in the main channel 362 to in a sense siphon fluid headed to the pump assembly 214 and direct it back to the reservoir 104. The regulator housing 326 may include a plurality of securing features, such as brackets 366, 368 that are configured to receive fasteners for securing the housing within the base 102.

Figure 6D:
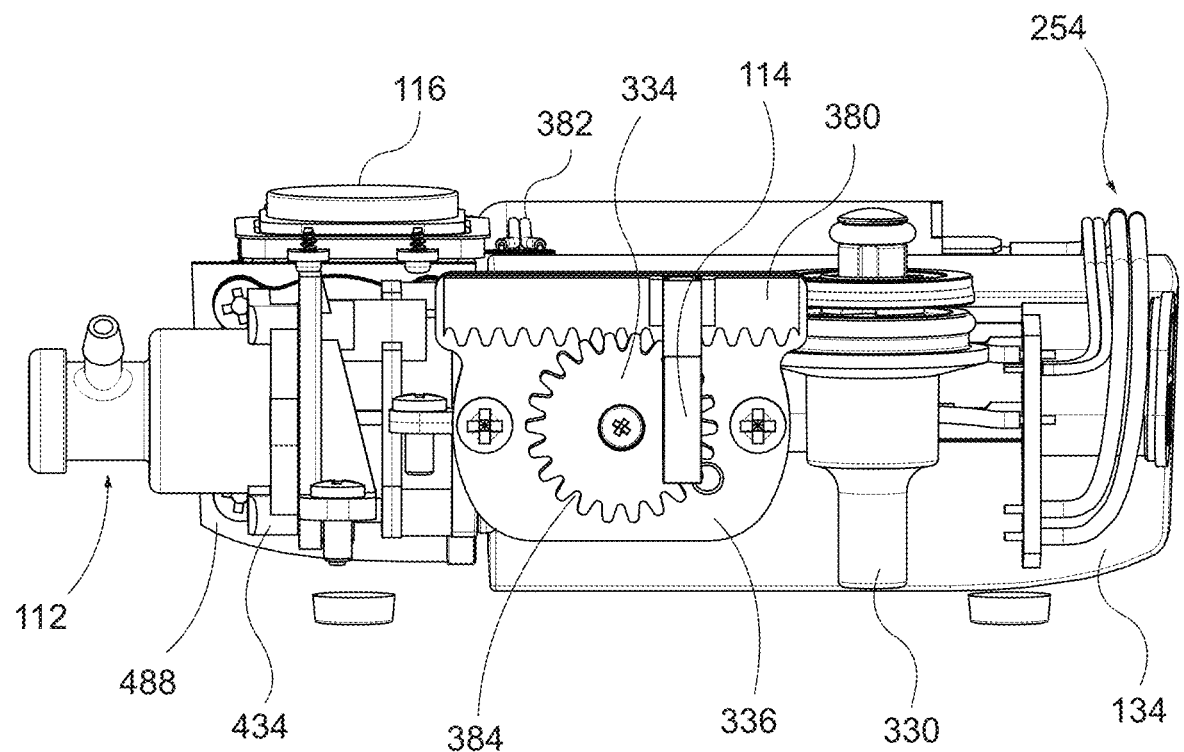
FIG. 6D is a side elevation view of the operating components of FIG. 6A.
Figure 13:
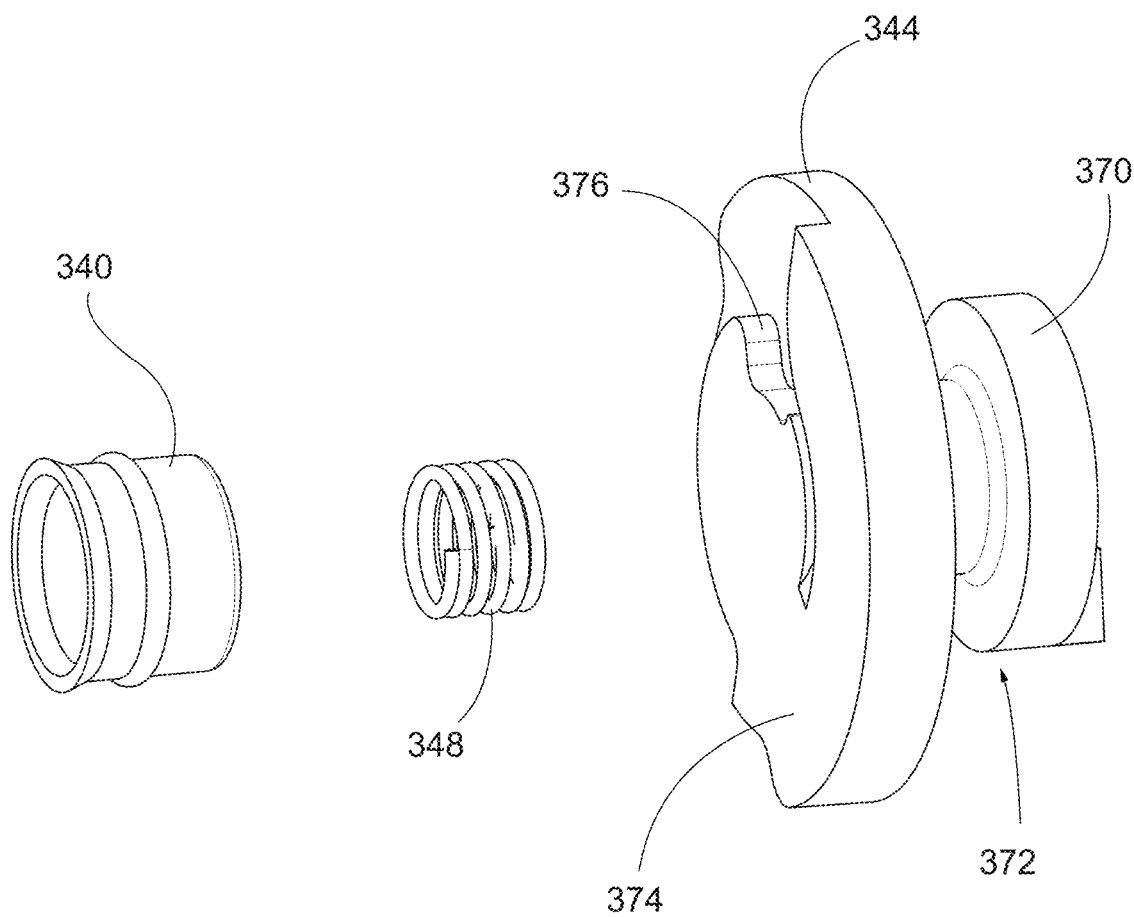
FIG. 13 is an exploded view of a pressure regulator valve.

FIG. 13 illustrates an exploded view of the pressure valve 344, the biasing element 348, and the seal 340. With reference to FIGS. 6C and 13, the pressure valve 344 is used to vary one or more characteristics of the flow channel between the inlet and outlet 360, 358 in the regulator housing 326. With reference to FIGS. 6C, 6D, and 13, the pressure valve 344 includes a gear face 370 for interfacing with and connecting to the gear 334 and a sealing face 374. The sealing face 374 varies in the thickness and includes a flow channel 376 defined therein. The flow channel 376 varies in dimension and shape and extends in a generally curved manner around a central area of the sealing face 374.

The seal 340 is biased against the sealing face 374 of the pressure valve 344 and includes a flow aperture 378 defined therethrough. The flow aperture 378 is typically in fluid communication with the flow channel 376 of the sealing face 374 and the main channel 362 but varies where it engages with the flow channel 376 based on the position of the pressure valve 344, as discussed in more detail below.

With reference to FIGS. 6C and 6D, the pressure assembly 228 includes the gear 334, a corresponding rack 380, and the actuator 114. The rack 380 includes a plurality of teeth 382 that engage with the teeth 384 on the gear 334. The actuator 114 is coupled to the rack 380, which moves laterally relative to the rack bracket 336. For example, the rack bracket 336 may include one or more longitudinal grooves and the rack 380 may include pegs that are received into the grooves to secure the rack 380 to the bracket 336. The grooves allow the rack 380 to slide laterally relative to the bracket 336. The actuator 114 is connected to the rack 380 and configured to move the rack 380 in the lateral direction to actuate the gear 334, as discussed in more detail below.

With reference to FIG. 10, the dual valve assembly 328 will now be discussed in more detail. The dual valve assembly 328 acts both as a regulator valve to regulate fluid into and out of the reservoir into the pump chamber 322, as well as to help prevent damage to the pump in the event of a blockage at the tip, such as activation of a pause button on the handle 106, such that the dual valve acts as a check valve. For the primary valve function of the dual valve assembly 328, the dual valve assembly 328 includes a valve housing 388 which may be a substantially cylindrical hollow component and is configured to slide within the main channel 362. The valve housing 388 terminates in a terminal end 394 having an aperture defined through a front surface thereof. The second end of the valve housing 388 includes a seal cap 398 that includes a flow channel 400 defined therethrough. The flow channel 400 is in communication with the reservoir connector 330.

For the secondary or check valve function, the dual valve assembly 328 includes a spring actuated valve within the valve housing 388, in some instances the spring actuated valve may be considered a third valve of the oral irrigator. In particular, a support post 396 having a flow channel defined therethrough is connected to the seal cap 398, a biasing element 392 is received within the valve housing 388 and aligned with the support post 396. A plunger 390 is connected to the biasing element 392 and configured to move therewith. The plunger 390 may include a tapered shape, such as a cone or frustum, and has a terminal end diameter that is the same diameter as that of the aperture in the terminal end 394 of the valve housing 388. The force of the biasing element 392 is selected to be overcome by fluid back pressure that exceeds a predetermined amount, such as the pressure build up due to a blockage of the jet tip 108.

Handle Connection Assembly

Figure 14:
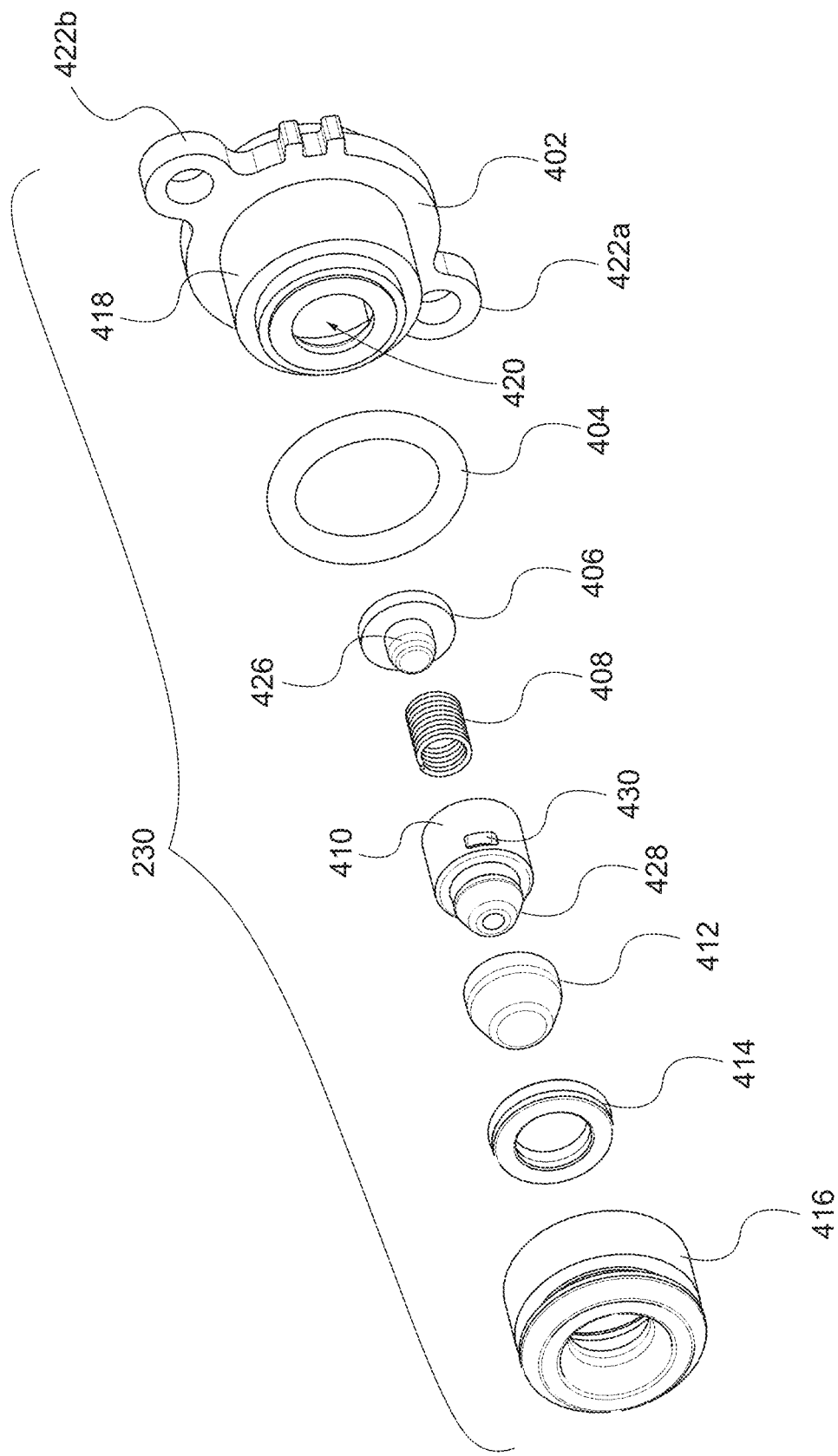
FIG. 14 is an exploded view of a connection assembly.

The connection assembly 230 will now be discussed in more detail. FIG. 14 illustrates an exploded view of the connection assembly 230. With reference to FIGS. 6C and 14, the connection assembly 230 includes an outlet fitting 402 and a spring bearing 406, as well as a first valve that may include a biasing element 408, a poppet 410, a poppet cap 412, a top cap 416, and sealing members 404, 414. The outlet fitting 402 interfaces with the pump body 284 and includes a central boss 418 having a cavity 420 defined therethrough. The outlet fitting 402 may include one or more securing flanges 422a, 422b for receiving fasteners to secure to the pump body, portions of the housing, etc.

The bearing 406 includes a support post 424 (see FIGS. 6C and 10) extending from a rear surface and a receiving post 426 extending from a front surface. The posts 424, 426 are configured to be positioned within a receiving recess in the pump body 284 and receive the biasing member 408, respectively.

As shown in FIG. 14, the poppet 410 is a generally cylindrical body having a tapered end with a closed tip 428. One or more fluid apertures 430 may be defined by the sidewalls of the body. The end cap 412 is configured to seat on the closed tip 428 of the poppet 410 and may be configured to correspond to the shape and dimension of the closed tip 428 such that it may be press fit onto the closed tip 428 end of the poppet 410.

The top cap 416 forms the end component of the connection assembly 230 and is connected to the outlet fitting 402 with the various components of the connection assembly 230 positioned between the two. The sealing components may be O-rings, such as seal element 404, or seal-cups, such as seal member 414 and may be positioned around select components of the connection assembly 230 or as desired to create fluid-proof connections.

The latch assembly 432 selectively connects and disconnects the hose connector 112 to the base 102 will now be discussed in more detail. With reference to FIGS. 6A, 6C, and 10, the latch assembly 432 includes the eject button 118, a biasing element 444, and a latch 434. The eject button 118 is configured to actuate the latch 434 and includes an outer surface that a user actuates, a central cavity 446 for receiving the biasing element 444 and a tapered interior actuation tip 442. The actuation tip 442 is shaped as a frustum or blunt ended cone that slowly increases in diameter from the most interior surface toward the outer surfaces. As will be discussed in more detail, the actuation tip 442 is configured to move the latch 434 from an engaged position to a released position. The latch 434 includes two latch arms 436a, 436b connected together at one end by a leaf spring 440. Each of the latch arms 436a, 436b are generally elongated members and include detents 438a, 438b extending inward from a first sidewall toward the opposite arm.

The hose connector 112 is used to fluidly connect the handle 106 to the base 102 and will now be discussed in more detail. With reference to FIGS. 3D and 10, the hose connector 112 includes a connector body 452 with a cap 450 connected thereto. The connector body 452 defines an interior lumen 456 housing a spring actuated valve and a lower body 462 that is partially inserted to the base 102, as discussed in more detail below. The interior lumen 456 of the connector body 452 is fluidly connected to a prong lumen 466 that is defined by a prong 464 extending downward from a bottom end of the connector body 452. The prong 464 is positioned within a central region of the lower body 462 and includes one or more fluid apertures 468 defined as cutouts in its bottom end for fully connecting the prong lumen 466 to the pump assembly 214. The bottom end of the lower body 462 includes an external flange 470 extending circumferentially around the lower body 462. The external flange 470 selectively engages the latch 434 to secure the hose connector 112 to the base 102.

With reference to FIGS. 3D and 10, the hose connector 112 includes a leak valve, which in some instances may be considered a second valve, and may be in the form of a poppet 460 and a biasing element 458. The biasing element 458 is secured to a post extending from a bottom surface of the cap 450 and biases the poppet 460 toward the entrance to the prong lumen 466. The poppet 460 is selected to have a diameter that is larger than the entrance to the lumen 466 such that when activated the poppet 460 seals the entrance and prevents fluid, such as water stuck in the hose 110 after use of the irrigator, from leaking out when the hose connector 112 is removed from the base. However, the biasing element 458 is selected such that its force is able to be easily overcome by the fluid pressure expelled by the pump assembly 214.

Assembly of the Oral Irrigator

The assembly of the oral irrigator 100 will now be discussed. It should be noted that the below discussion is not meant to convey a particular assembly order, but merely to describe the connection of different elements to one another. As such, the below discussion is meant as illustrative only. With reference to FIGS. 5, 6B, 6C, 7A, and 7B, the drive assembly 216 is connected together and secured to the lower housing 178 of the base 102. The chassis 220 and the motor 218 are connected together and secured in the dry compartment 208 of the lower housing 178.

The pinion pulley 240 is positioned on the drive shaft 242 of the motor 218 and the belt 238 is slid over the outer surface of the pinion pulley 240 with the belt teeth meshing with the teeth 256 on the outer surface of the pinion pulley 240. The flange 231 is then connected to the outer perimeter of the pinion pulley 240 to secure the belt on the outer surface of the pinion pulley 240. The ball bearing race 252 is received around the outer surface of the engagement boss 260 of the driven pulley 250 and the connecting end 272 of the connecting rod 236 or crank is received around the outer surface of the ball bearing race 252. The belt 238 is positioned on the outer surface of the driven pulley 250 and the flange 248 is connected to the pulley 250 to secure the belt 238 on the pulley. The belt 238 may alternatively be connected to the pulleys 240, 250 after the pulleys are connected to their driving components or respective shafts.

The gear pin 232 is then received through the aperture in the pin structure 262 of the driven pulley 250 and connected to a corresponding groove in the chassis 220. The securing bracket 222 (see FIG. 7A) is then connected to the chassis 220 via a plurality of fasteners connected to bosses extended from the chassis 220, such as bosses 220a, 220b, 220c. With reference to FIGS. 6C and 10, the connecting rod 236 is inserted into an aperture defined through the first sealing plate 488 and the top surface 484 of the diaphragm seal 480 is positioned between the two sealing flanges 282a, 282b of the connecting rod 236. The beaded flange 482 of the seal is clamped in position and the second sealing plate 490 is positioned over the edge of the diaphragm seal 480 and engages with the outer surface of the first sealing plate 488. The first and second sealing plates 488, 490 are then clamped together with fasteners, with the edges of the diaphragm seal being clamped therebetween and the connecting rod extending between apertures in the two plates 488, 490. In this configuration, the connecting rod 236 and the seal 480 create a fluid seal between the dry compartment 208 and the wet compartment 206 in the lower housing 178 of the base 102.

The pump assembly 214 is connected and coupled to the drive assembly 216. With reference FIGS. 6C and 10, the piston 283 is connected to the ball 280 of the connecting rod 236. The pump body 284 is secured to the lower housing 178 of the base unit via fasteners connected to the securing bracket 294.

With reference to FIGS. 10, 11A, and 14, the connection assembly 230 is assembled and connected to the pump body 284. In particular, the support post 424 of the bearing 406 is received within the pin recess 306 in the back wall 304 of the valve housing 300 in the pump body 284. The biasing element 408 is then positioned around the post 426 of the bearing 406. The poppet 410 is received around the biasing element 408 with the cap 412 connected to the end portion of the poppet 410 with the closed tip 428. The outlet fitting 402 is positioned over the valve assembly such that the poppet 410 is positioned within the boss 418. The O-ring 404 is received between the fitting 402 and the pump body 284 and in one embodiment is held in position by the securing flanges 422*a*, 422*b*, which are connected by fasteners to the securing posts 298*a*, 298*b* of the pump body 284. The seal member 414 may be a cup that is positioned within the top cap 416, which is then press fit or otherwise secured to the top end of the boss 418.

With reference to FIGS. 10 and 11A, the eject button 118 and biasing element 444 are connected to the pump body 284. In particular, the biasing element 444 is received in the spring wall or post 292 and the latch 434 is connected around the biasing element 444 with the arms extending around the connection assembly 230. Then, the eject button 118 is connected to the biasing element 444 with the latch 434 positioned between the eject button 118 and the pump body 284. The biasing element 444 is received within the central cavity 446 of the eject button 118 with the actuation tip 442 being oriented toward the pump body 284.

The pressure assembly 228 is assembled and the dual or check valve assembly 328 is received within the main channel 362 of the regulator housing 326. The end portion of the dual valve assembly 328 is positioned within the tube 312 of the pump body 284 and abuts against the prongs 314. The inlet 356 to the regulator housing is connected to the reservoir connector 330 and the regulator housing 326 is then secured to the lower housing 178 via the securing bracket 366, 368 and two fasteners. The reservoir connector 330 and the regulator housing 326 are positioned in the wet compartment 206 of the lower housing 178. The regulator housing 326 and the pump body 284 are connected together via fasteners securing the securing posts 298*c*, 298*c* of the pump body 284 and the securing brackets 367 of the regulator housing 326 together.

With reference to FIGS. 6C, 12A, 12B, and 13 the pressure valve 344 is connected to the regulator housing 326. For example, the biasing element 348 is received within the inlet 358 of the valve compartment 350 in the regulator housing 326 and the seal 340 is received around the biasing element 348. An O-ring 342 is positioned in the groove 372 in the valve 344 and the valve 344 is positioned in the valve compartment 350 with the sealing face 374 positioned to face the back wall of the valve compartment 350.

With reference to FIGS. 6C and 6D, the actuation assembly is then connected to the pressure valve 344. In particular, the rack bracket 336 is positioned against the regulator housing 326 aligned such that the fastening posts 352*a*, 352*b* align with corresponding features on the rack bracket 336. The rack bracket 336 is secured via fasteners to the regulator housing 326. The gear 334 is connected to the valve 344 by a fastener, such as a screw, and the rack 380 is press fit into the longitudinal slots in the rack bracket 336. The actuator 114 is then connected to the rack 380 and select teeth 382 are positioned to engage select teeth 384 of the gear 334.

Power Button

With reference to FIGS. 6B and 6D, the power button 116 is secured on a bracket 431 and is electrically connected to the motor 218 through a circuit board 131 that electrically connects the motor 218 to a power source coupled to the power port formed by the male power connector socket 136 and the power assembly 134.

With reference to FIGS. 6B and 6D, in the assembled positioned, the drive assembly 216, pump assembly 214, connection assembly 230, and pressure assembly 228 are arranged in a U type shape when viewed from a top plan view. In this manner, the central region of the base 102 can be hollow to allow insertion of the power assembly 134 in the storage configuration or to define a battery compartment for receiving a battery (or other accessory storage). In one embodiment, the motor 218 is arranged so as to be substantially perpendicular to the pump body 284 and substantially parallel to the regulator housing 326. Further, the pump body 284 is arranged to be perpendicular to the reservoir connector 330 and the reservoir outlet. These types of arrangements allow the oral irrigator 100 to have a reduced size, both in width and height.

With reference to FIG. 4, once the internal components are connected together and received within the lower housing 178, the upper housing 180 is secured to the lower housing 178. The sealing wall 192 of the lower housing assists in sealing the dry compartment 208 from the wet compartment 206 in the lower housing 178. The port wall 194 of the upper housing 180 is positioned around a portion of the reservoir connector 330 to help prevent fluids from leaking from the reservoir connector into the secondary dry compartment 204. The upper housing 180 is secured in a number of different manners, such as press fit, sonic welding, adhesive, fasteners, or the like. The face plate 182 is secured on top of the upper housing 180 and the trim ring 126 is positioned underneath the face plate 182 to surround the perimeter of the face plate 182. The face plate 182 and the upper housing 180 to secure the position of the trim ring 126.

Separable Power Assembly

Figure 3C:
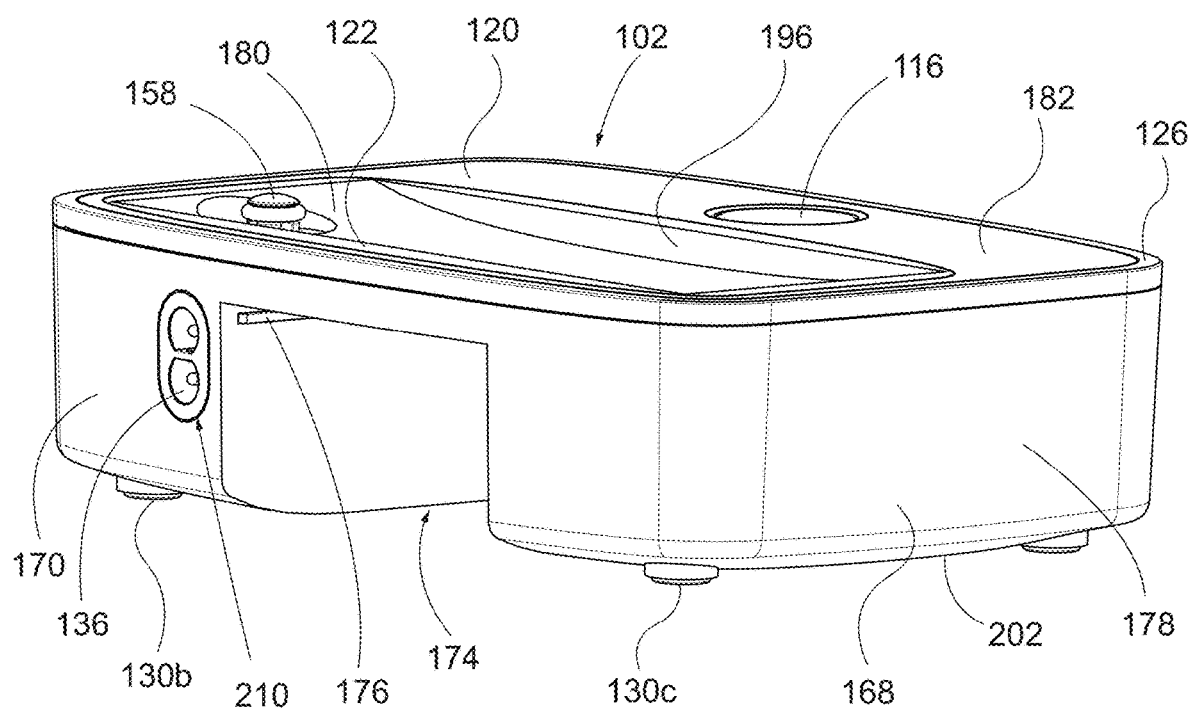
FIG. 3C is a front isometric view of the base of FIG. 3A.
Figure 3D:
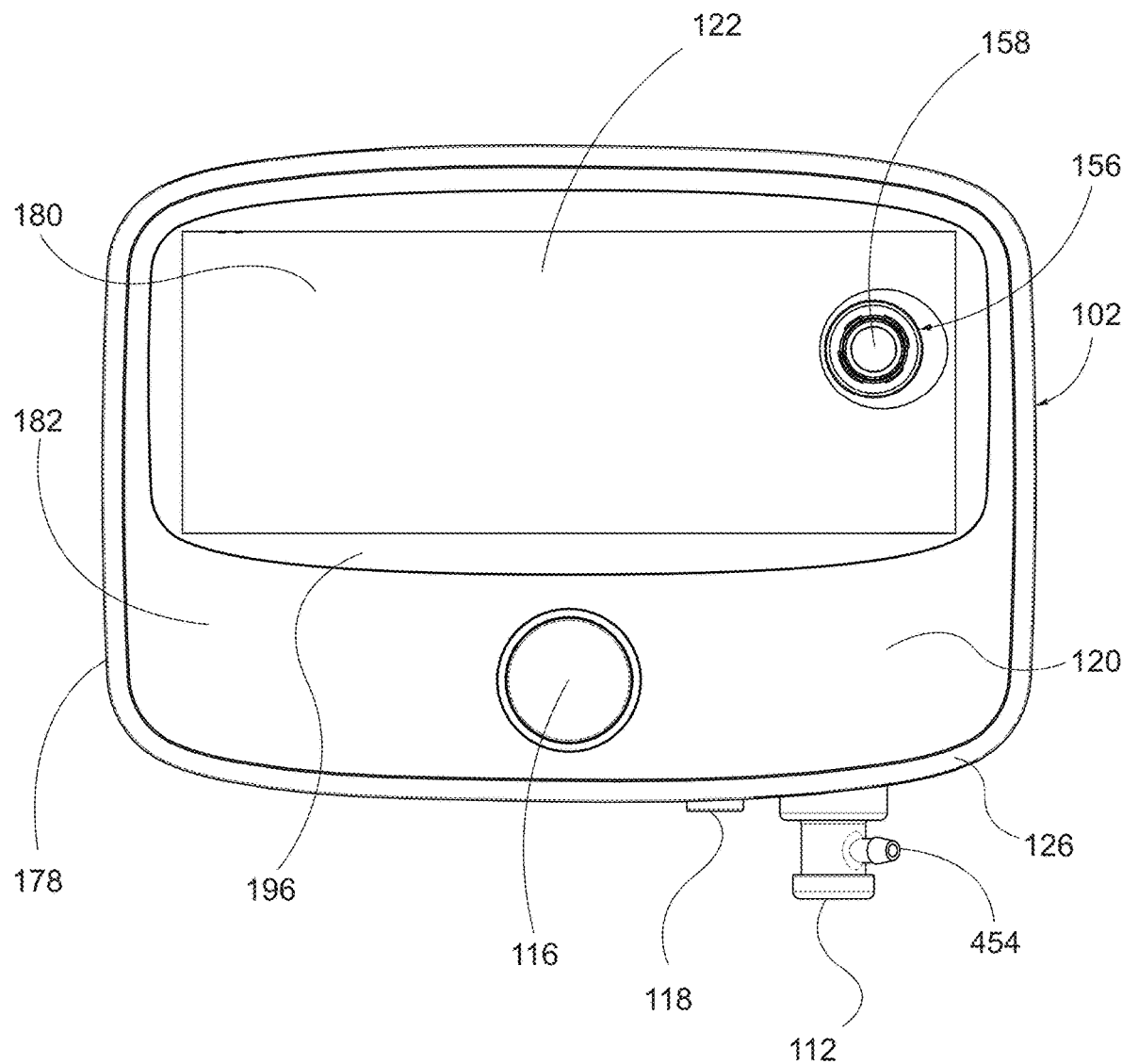
FIG. 3D is a top plan view of the base of FIG. 3A.

With reference to FIGS. 10 and 3C, in the storage position, the power assembly 134 is inserted into the power block cavity 174 of the lower housing 178. The alignment ribs 176 align with corresponding grooves on the power assembly 134 to guide the power assembly 134 into the power block cavity 174. Additionally, the magnet 474 (see FIG. 5) in the lower housing 178 attracts a corresponding magnet in the power assembly 134 to secure the power assembly 134 in place with the front wall of the power assembly resting against the back wall of the power block cavity 174.

Figure 16:
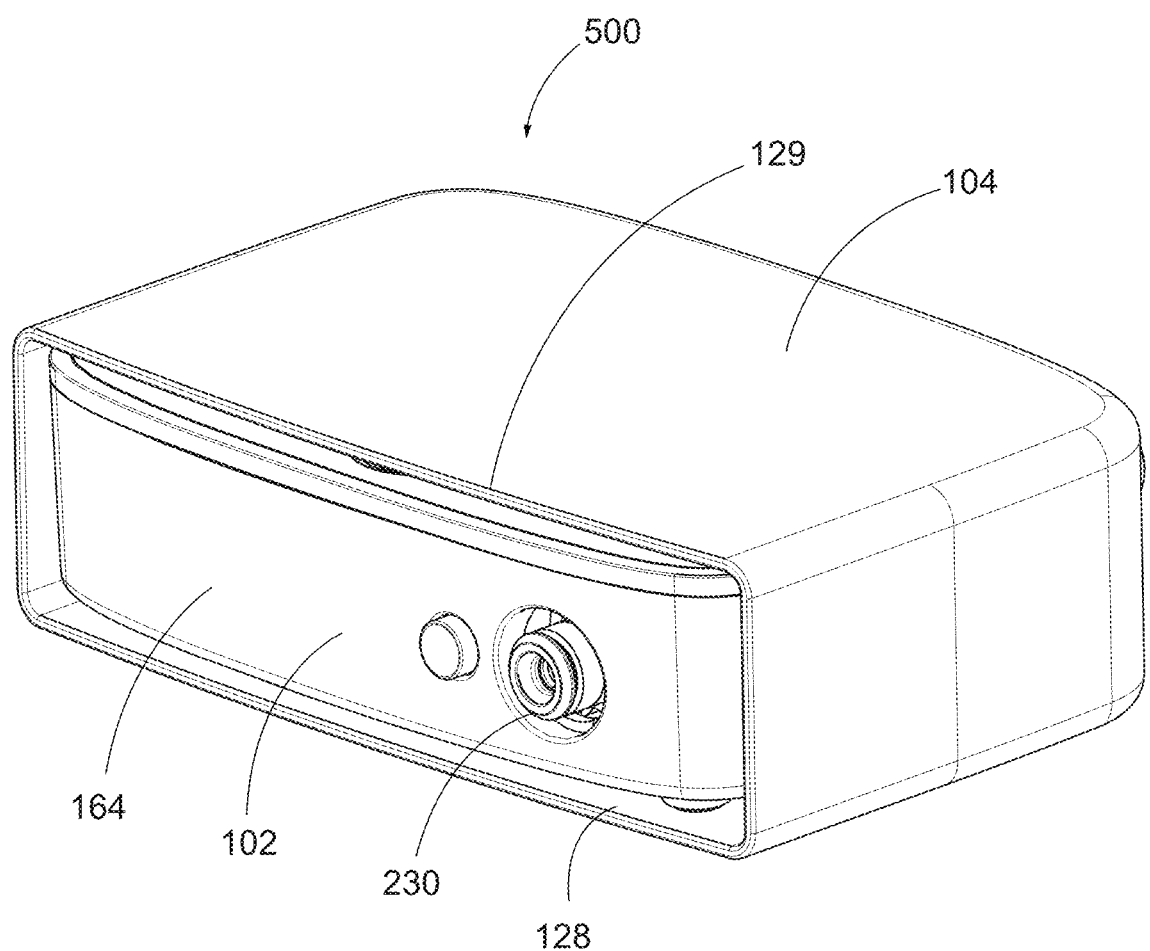
FIG. 16 is a front isometric view of the oral irrigator of FIG. 1A in a storage or collapsed position.

With reference to FIG. 16, in the storage configuration 500, the base 102 with the power assembly 134 secured in the power block cavity 174 is inserted into the reservoir 104. As shown in FIG. 16, the base 102 is sized to fit completely within the reservoir 104 and the top edges 128, 129 of the reservoir 104 may extend partially beyond the front wall 164 of the base 102. The eject button 118 and the top cap 416 of the connection assembly 230 do not extend past the edge of the reservoir 104 and so will not snag on fabric or other elements if the oral irrigator 100 is received within a carrying case. In the storage configuration 500, the oral irrigator 100 is configured to be easily inserted into a case or compartment and the reservoir 104 acts as a hard container for protecting the internal components of the base 102 and also enhances the ability of the oral irrigator 100 to easily slide into a fabric or other similar type of case.

Operation of the Oral Irrigator

Figure 15A:
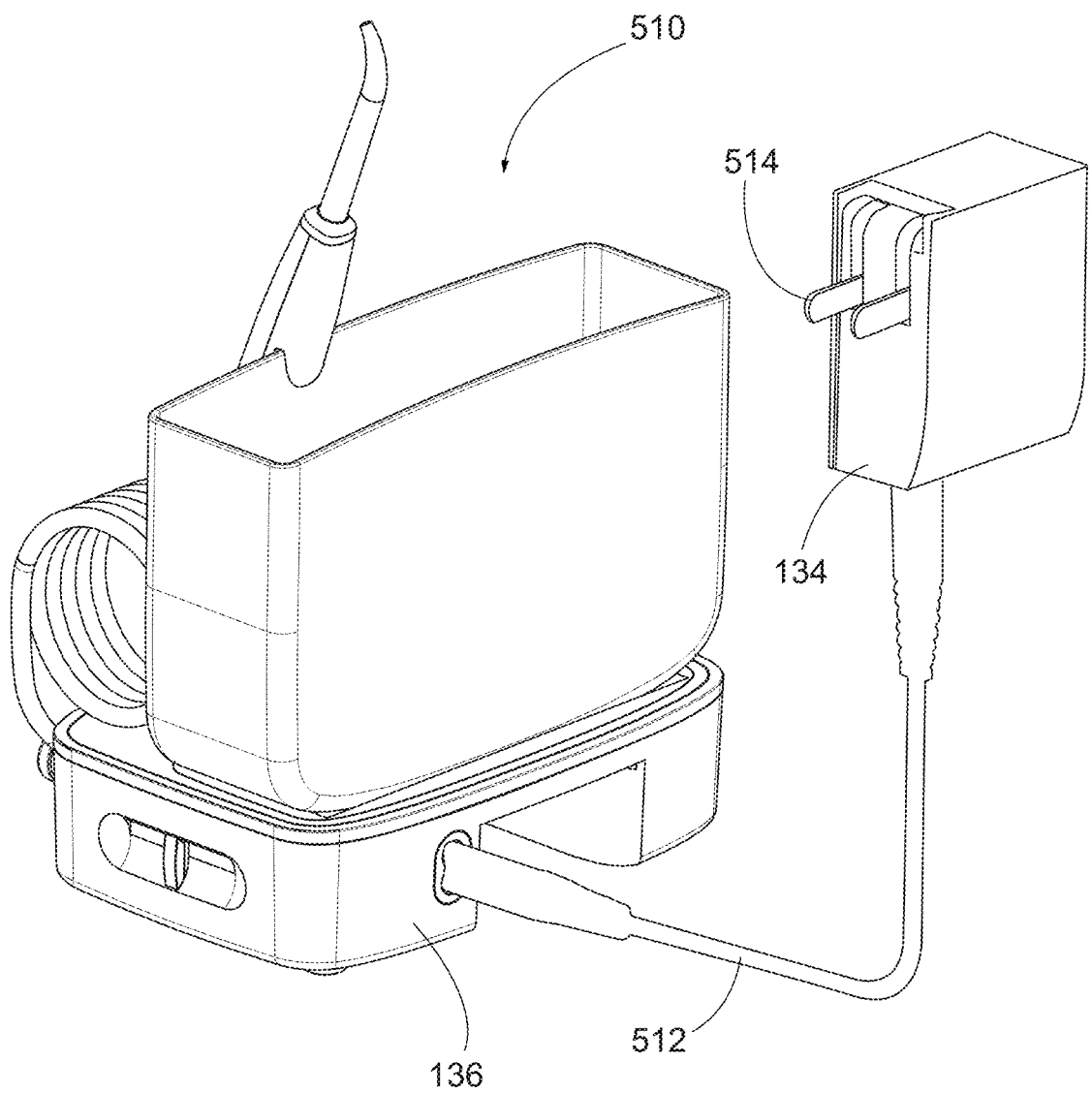
FIG. 15A is a rear isometric view of the oral irrigator of FIG. 1A with the power assembly in a use orientation.
Figure 15B:
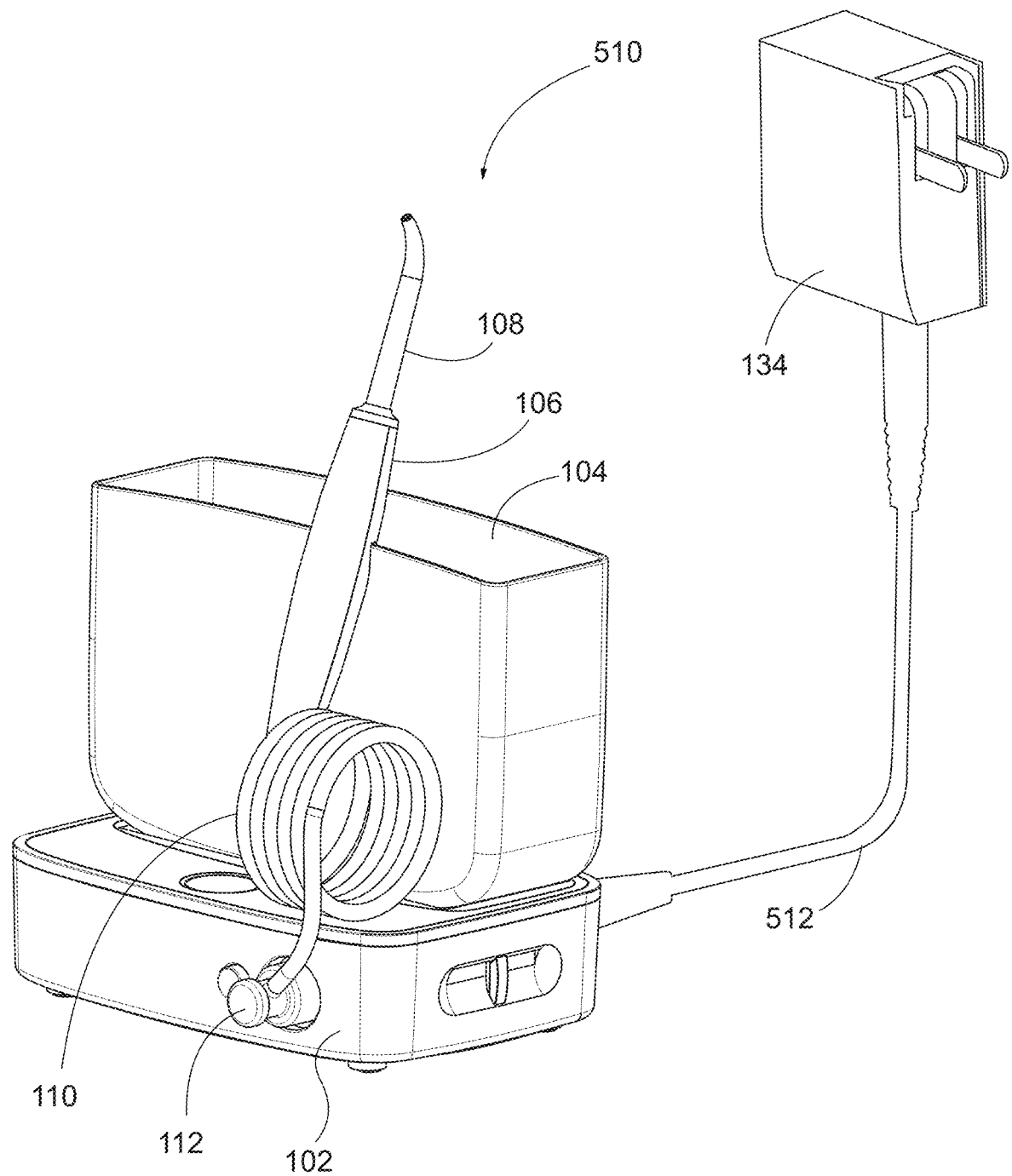
FIG. 15B is front isometric view of the oral irrigator of FIG. 15A.

Operation of the oral irrigator 100 will now be discussed in more detail. FIGS. 15A and 15B illustrate rear and front isometric views, respectively, of the oral irrigator 100 in the use configuration 510. To use the irrigator, the base 102 is removed from the reservoir 104 and the reservoir 104 is connected to the top of the base 102. The reservoir 104 sits within and on top of the engagement surface 122. The engagement surface 122 may be contoured to match the shape of the reservoir 104 and the lip 196 surrounding the engagement surface 122 helps to prevent fluid from the reservoir 104 from leaking out of the base 102. The reservoir port 142 (see FIG. 2) is received within the reservoir aperture 156 defined in the base 102. The reservoir port 142 is positioned around the reservoir connector 330 and the reservoir valve 158, which activates the valve to allow flow from the reservoir to the pressure assembly 228.

The power assembly 134 is removed from the power block cavity 174 in the base 102 and the prongs 514 are unfolded from the housing. A power cord 512 can then be connected to the male power connector socket 136 of the power port in the base 102 and the power assembly 134. When the power assembly 134 is connected to a power source, such as a wall outlet, electricity can flow from the power assembly 134 to the circuit board 131 in the base 102 to provide power to the oral irrigator 100. In some embodiments the power assembly 134 may include one or more converting components that convert the power source from alternating current to direct current, but the type of conversion (if any) depends on the type of motor and the components that may be positioned within the base 102.

The handle 106 is then fluidly connected to the base 102. The hose connector 112 is connected to the connection assembly 230. With reference to FIG. 10, the lower body 462 of the hose connector 112 is inserted such that the prong 464 is inserted into the top cap 416 of the connection assembly 230. The prong 464 compresses the cap 412 of the poppet 410, which in turn compresses the biasing element 408. As the cap 412 moves downward with the compression of the biasing element 408, the cap 412 unseats from the top end of the outlet fitting 402, allowing fluid to flow from the outlet fitting 402 into the fluid apertures 468 in the prong 464. Additionally, the hose connector 112 biases the arms 436*a*, 436*b* (see FIG. 6A) of the latch 434, which flex due to the spring 440 to open to engage the outer surface of the lower body 462 of the hose connector 112. The detents 438*a*, 438*b* are positioned around the lower body 462 to secure the hose connector 112 in position. To release the hose connector 112, a user presses the eject button 118, which compresses the biasing element 444, and moves the eject button 118 such that the tapered actuation tip 442 moves toward the latch 434, moving the arms 436*a*, 436*b* away from one another, moving the detents 438*a*, 438*b* away from another. As this occurs, the biasing element 408 of the connection assembly 230 exerts a force against the poppet 410 and the poppet cap 412 that pushes the prong 464 outward away from the fitting 402. This acts to help force the hose connector 112 out of engagement with the connection assembly 230. The user can then remove the hose connector 112.

When the hose connector 112 is removed from the connection assembly 230, the biasing element 458 seals the poppet 460 in the hose connector 112 to prevent fluid from leaking from the hose connector 112 through the entrance to the prong 464.

With the handle 106 fluidly connected to the base 102, the user turns the oral irrigator 100 on by pressing the power button 116. The motor 218 is then electrically connected to the power source and turns on. With reference to FIG. 6C, as the motor 218 operates, the drive shaft 242 rotates, rotating the pinion pulley 240. As the pinion pulley 240 rotates, the belt 238 moves, causing the driven pulley 250 to rotate about the gear pin 232. The rotation of the driven pulley 250 causes the connecting rod 236 to move correspondingly, slipping by its engagement with the bearing race 252. This causes the connecting rod 236 to move in a substantially lateral movement, although the driven pulley 250 is moving in a rotational movement. The belt drive for the drive assembly 216 allows the size of the base unit 102 to be reduced because there is no need for a separate gear housing that is typically used to prevent grease from possibly mixing into the fluid and/or interfere with the operation of other components. Further, the belt drive reduces the noise as the teeth of the pulleys do not directly mesh with one another, eliminating the need for the drive assembly to be mounted above the bottom floor of the lower housing 178, which may typically be done in conventional oral irrigators to reduce vibrations.

As the connecting rod 236 moves laterally with respect to the sealing plates 488, 490, the diaphragm seal 480 moves therewith. Because the diaphragm seal 480 merely changes in length (as the bellows expands and contracts), the seal 480 does not exert a drag force on the connecting rod 236, enhancing the efficiency of the drive assembly 216, while maintaining the seal between the dry and wet compartments 206, 208.

With continued reference to FIG. 6C, as the connecting rod 236 moves, the piston 283 moves laterally within the pump chamber 290 in the pump body 284. On a downward stroke, the piston 283 moves toward the sealing plates 488, 490, increasing the available volume within the pump chamber 290, creating a vacuum pull. This vacuum causes fluid from the reservoir 104 to flow through the reservoir valve, into the reservoir connector 330 and into the regulator housing 326. The force created by the piston 283 movement also pulls the dual valve assembly 328 toward the pump housing 234, unseating the dual valve assembly 328 from the inlet 356 of the regulator housing 326. This allows fluid from the reservoir connector 330 to flow into the main channel 362, around the dual valve assembly 328, and into the pump chamber 290.

On an upward stroke, the piston 283 moves toward the valve housing 300 of the pump body 284. This forces fluid within the pump chamber 290 out of the pump chamber 290 and into the outlet 308 in the pump body 284. The fluid then flows into the outlet fitting 402, around the poppet valve 410 and into the fluid apertures 468 in the prong lumen 466 of the prong 464 of the hose connector 112. The fluid force overcomes the biasing force exerted by the biasing element 458 in the hose connector 112, and unseats the poppet form the aperture connecting the prong lumen 466 to the interior lumen 456 of the housing, which then flows into the hose 110 and into the handle 106 and out the tip 108.

To adjust the pressure during operation, the user moves the actuator 114. With reference to FIGS. 6C and 6D, lateral movement of the actuator 114 causes the rack 380 to slide relative to the rack bracket 336, causing the gear 334 to rotate. As the gear 334 rotates, with reference to FIGS. 6C and 13, the pressure valve rotates, causing the inlet 358 to the valve compartment 350 in the regulator housing 326 to open, allowing fluid to bypass from entering into the pump body 284. The fluid flows through the inlet 358 through the valve compartment 350 within the flow channel 376 in the pressure valve 344 to the valve outlet 360 and back to the reservoir 104. The amount of fluid allowed to flow through the bypass channel defined by the sealing face 374 varies based on the location of the sealing face 374 relative to the valve inlet 358, thus rotating the gear 334 further in a particular direction will align a wider or shorter portion of the channel 376 with the inlet 358, decrease or increasing, respectively, the pressure output by the pump to the tip 108.

Handle

Figure 1B:
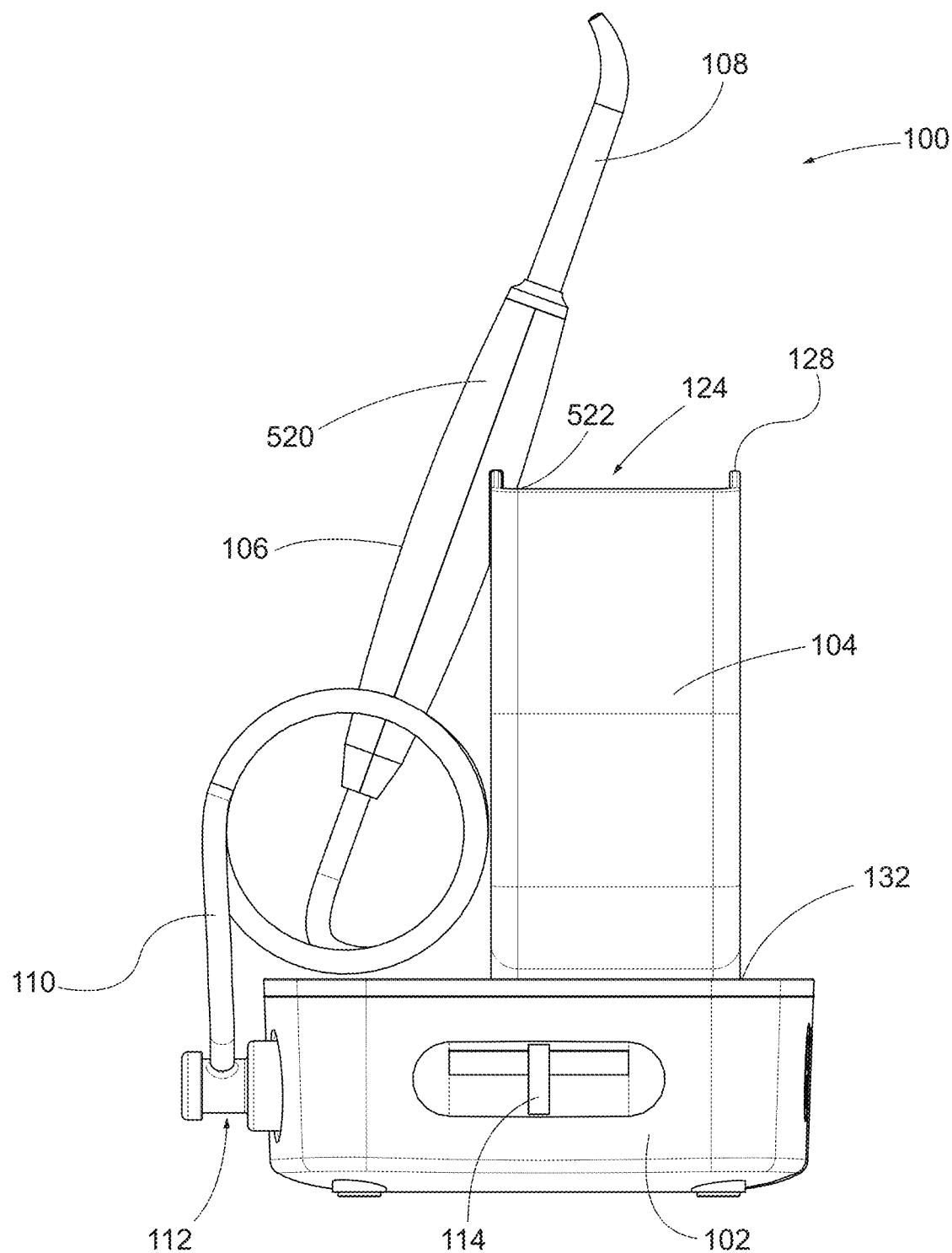
FIG. 1B is a side elevation view of the oral irrigator of FIG. 1A.
Figure 1C:
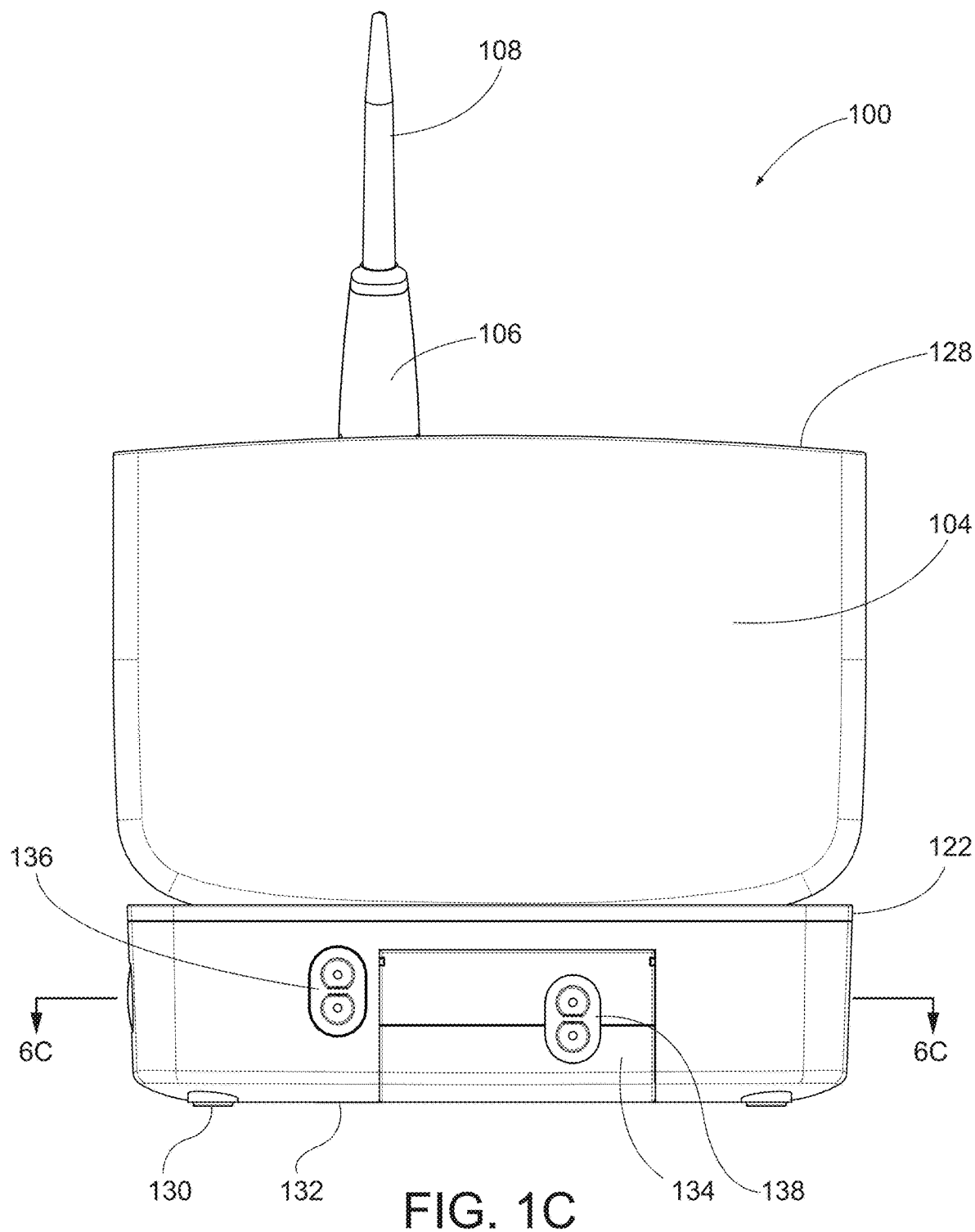
FIG. 1C is a rear elevation view of the oral irrigator of FIG. 1A.
Figure 1D:
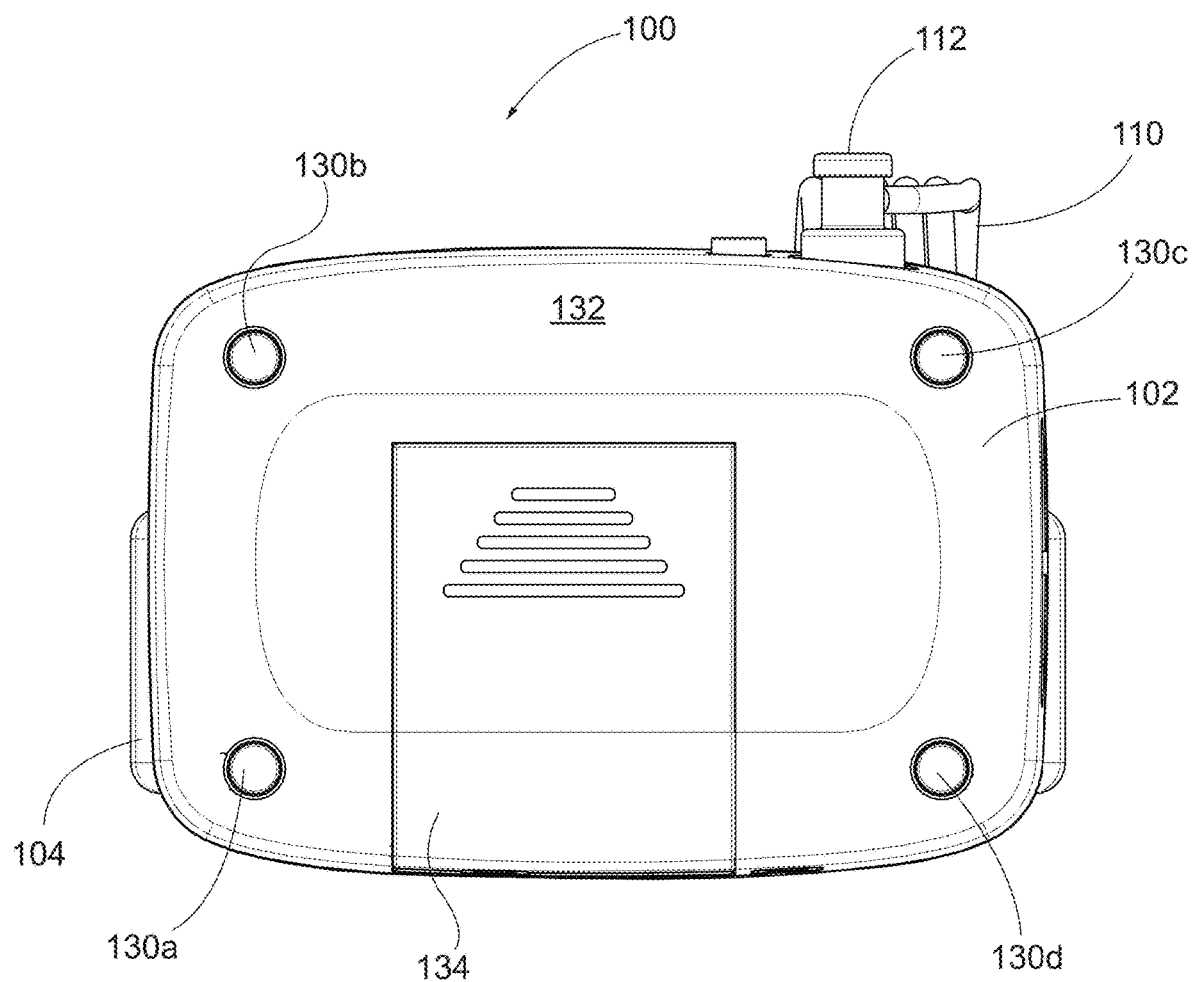
FIG. 1D is a bottom plan view of the oral irrigator of FIG. 1A.
Figure 25:
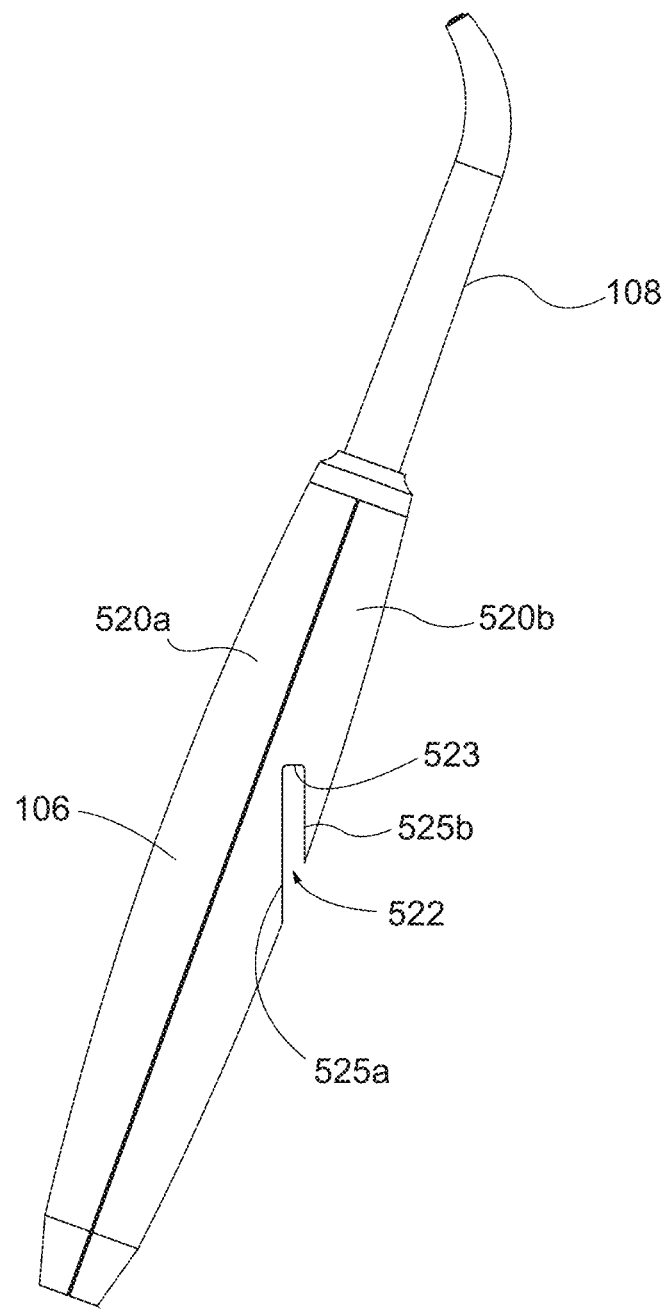
FIG. 25 is a right side elevation view of the handle of the oral irrigator of FIG. 1.

With reference to FIGS. 1B and 25, the handle 106 may include a handle housing 520 having a front housing half 520*a* and a rear handle housing 520*b*. An angled hanging slot 522 may be formed in the rear handle housing 520*b* generally extending between each lateral side of the rear handle housing 520*b* and further extending in depth toward the tip 108. The hanging slot 522 may be bounded by two opposing walls 525a, 525b spaced apart from each other and a transverse wall 523 at a terminal interior end of the opposing walls 525a, 525b such that the outer wall of the rear handle housing 520b is open to the hanging slot 522 at lateral sides of the two opposing walls 525a, 525b and at a base end of the opposing walls 525a, 525b opposite the transverse wall 525. In some embodiments the opposing walls may be parallel to each other, planar, or both. The hanging slot 522 may be centered along the length of the handle housing 520 or otherwise positioned to be centered on the center of mass of the handle 106 in order to aid in balancing the handle 106 when hung on a support using the hanging slot 522. The width of the hanging slot 522 may be congruent with the thickness of the walls of the reservoir 104 at the top edges 128, 129. The top edges 128, 129 of the reservoir 104 may thus fit within the hanging slot until a location at the top edges 128, 129 abuts the support surface 523. The hanging slot 522 thereby allows the handle 106 to hang from the top edges 128, 129 of the reservoir 104. With this hanging slot 522, typical handle support element, such as C-clamps, cradles, or the like, can be omitted, reducing the number of parts for the oral irrigator 100, thus decreasing costs. The angle of the slot 522 may be selected to intersect the longitudinal axis of the handle 106 such that the handle 106 does not hang parallel to the reservoir 104, to make it easier for a user to grip around the handle 106 in the space between the reservoir 104 and the housing 520. However, in other embodiments, the groove may be substantially vertical relative to a length of the housing 520 to allow the handle 106 to hang more parallel to the reservoir walls.

The handle 106 may also include elements such as a pause button, tip eject, swivel, or the like. An example of these types of components and a handle that can be used with the oral irrigator 100 is described in related U.S. patent application Ser. No. 15/415,836, filed on 25 Jan. 2017 entitled "Swivel Assembly for Oral Irrigator Handle," (which claims priority to U.S. provisional patent application No. 62/286,792 filed on 25 Jan. 2016), which is hereby incorporated by reference in its entirety.

Alternate Embodiment

An alternate embodiment of an oral irrigator 1700 is additionally contemplated, which is substantially similar to the embodiment of FIGS. 1-16 and incorporates the components and operation as previously described. The alternate embodiment and components thereof are shown in FIGS. 17-21. In this alternate embodiment, the size and arrangement of the components installed within the lower base unit have been altered in order to achieve different benefits than offered in the embodiment of FIGS. 1-16. Such benefits may include a power assembly with non-adjustable prongs, a circuit board positioned centrally within the unit to create a generally balanced assembly, a stronger connection between the power connector and power connector socket, and a linear mechanical power transmission assembly. It should be noted that features not specifically referenced in FIGS. 17-21 may be the same as those shown and described with respect to FIGS. 1-16. For example, the valves shown in the oral irrigator base and/or hose connector may be the same as those shown and described with respect to FIG. 10.

Figure 17:
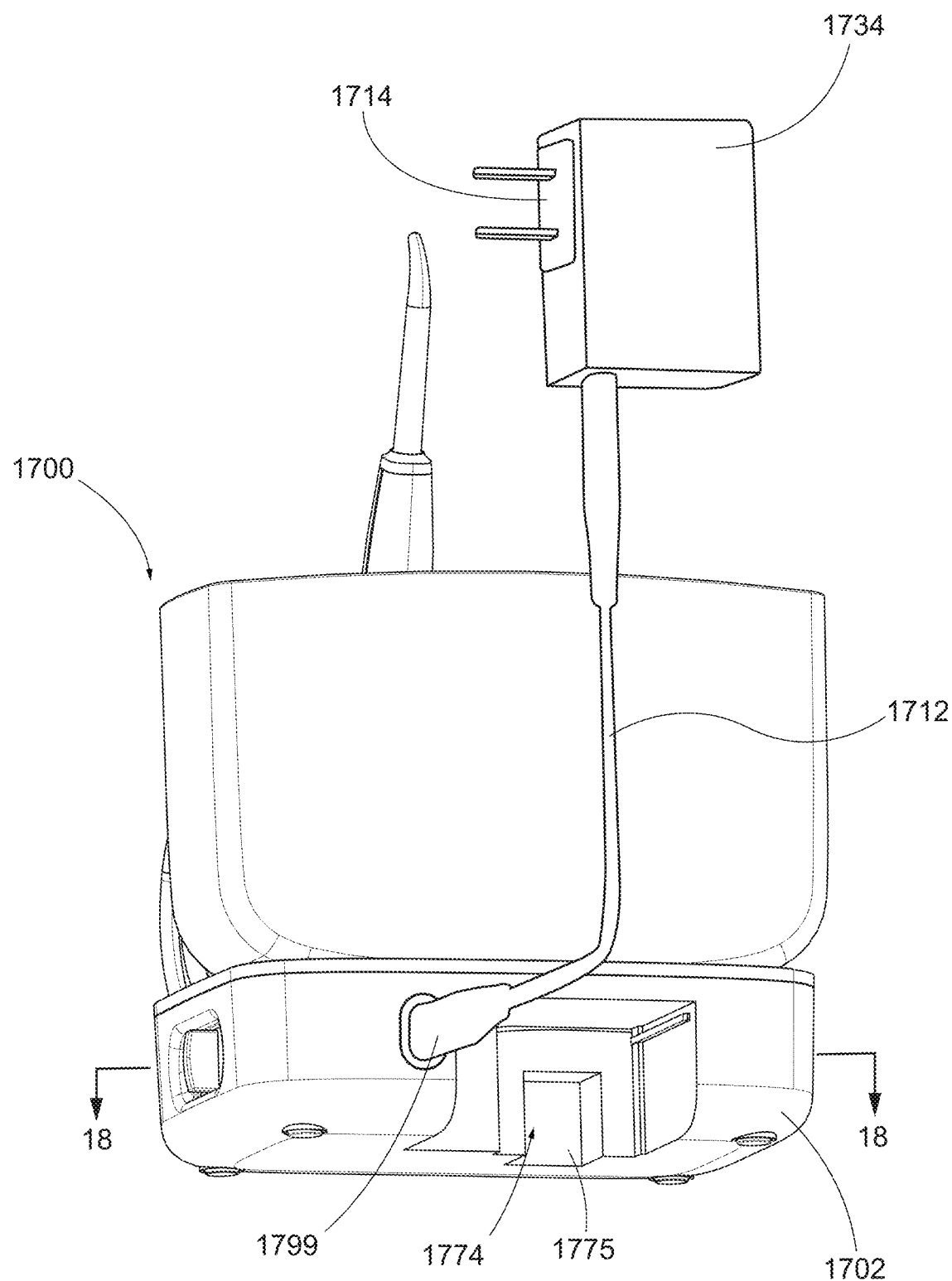
FIG. 17 is a rear isometric view of an alternate embodiment of an oral irrigator.

With reference to FIG. 17, in general, the location of the components positioned within the base 1702 have been reconfigured to, at least in part, create additional space for the power assembly and its prongs. Additional differences are discussed further below.

Power Assembly

Figure 18:
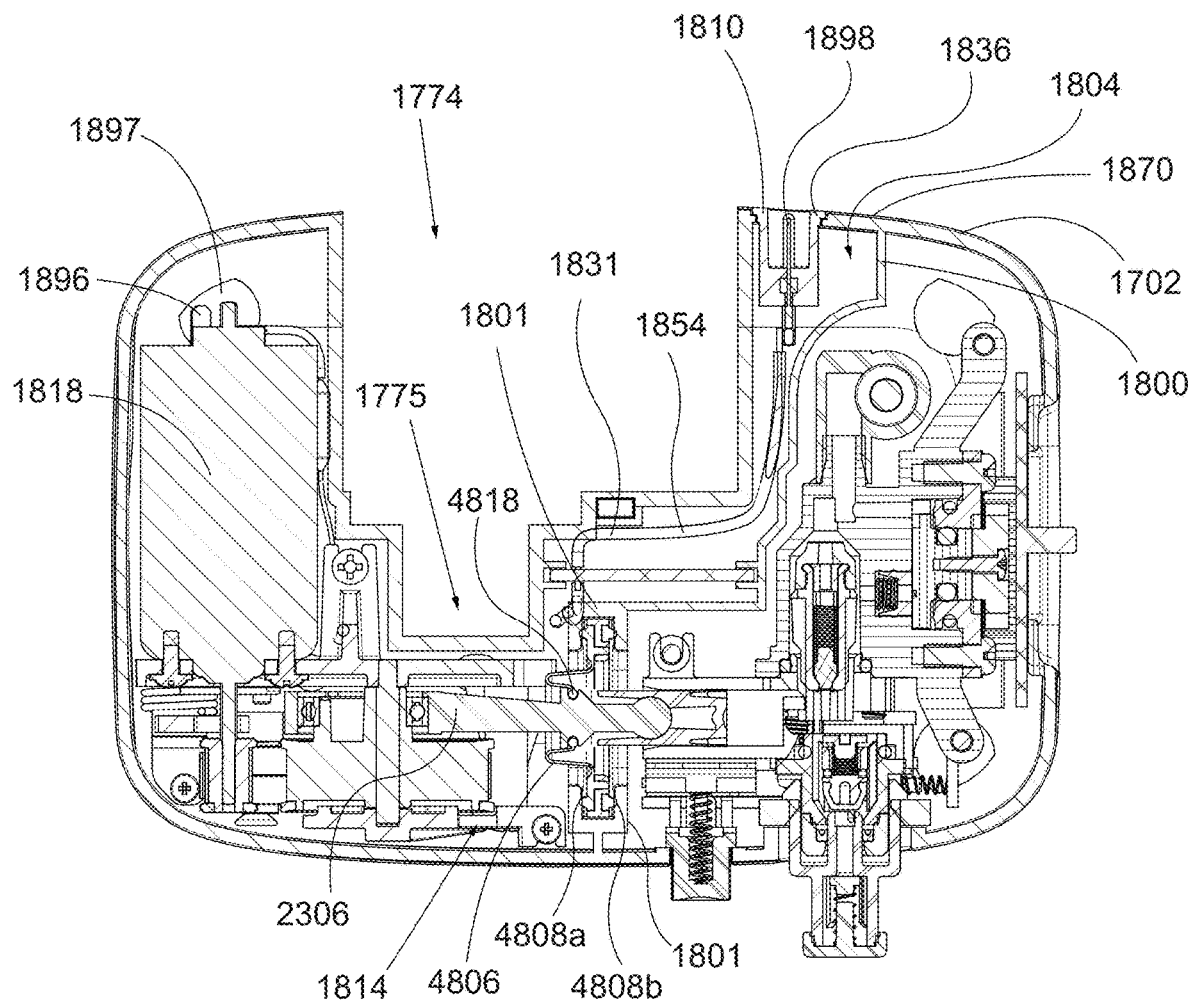
FIG. 18 is a cross-sectional view of the oral irrigator taken along line 18-18 of FIG. 17.

Similar to the embodiment shown in FIGS. 15A and 15B and with reference to FIG. 17, the power assembly 1734 is configured to fit within the power block cavity 1774 of the base 1702. The layout of the components within the base 1702 has been rearranged, thereby creating additional space for the power assembly 1734 and enabling the power assembly 1734 to no longer require prongs 1714 that are adjustable and collapse when stored within the power block cavity 1774. The size of the power assembly 1734 has also been reduced, creating more space in the main body of the base 1702. The alternate configuration of the various components within the base 1702 and the decreased power assembly 1734 size creates a prong space 1775 for the non-collapsible or non-adjustable extended prongs 1714 of the power assembly 1734 to slide into. With reference to FIGS. 17 and 18, the extended prongs 1714 may fit within the additional space 1775 of the power block cavity 1774 such that the power assembly 1734 no longer requires collapsible or adjustable prongs in order to fit within the power block cavity 1774, and therefore the extended prongs 1714 do not unfold, collapse, or adjust with respect to the power assembly 1734. The power assembly 1734 fits within the power block cavity 1774 in the base 1702.

Circuit Board Location

An alternate embodiment of the oral irrigator base 1702 as shown in FIG. 18 relocates the circuit board 131 from the position shown in FIG. 6C. With reference to FIG. 18, the optimized configuration of the components installed within the base 1702 also allows for the circuit board 1831 to be located central to the overall base 1702, between the drive assembly 1814 and the power block cavity 1774. The circuit board 1831 electrically connects the motor 1818 to a power source coupled to the power connector socket 1836 and the power assembly 1734. The central location of the circuit board 1831 allows for the simplified location of the wires 1854 connecting the motor 1818, the power button 1916 (shown in FIGS. 19A and 19B), and the power connector socket 1836, as compared to the circuit board 131 of the embodiment of FIGS. 1-16, which is located in the dry compartment 204 (shown in FIG. 6C), and wires 254 connecting the various powered elements are run in a space between the lower housing 178 and the upper housing 180 above the power block cavity 174 (shown in FIGS. 6A-6D). The simplified location of wires 1854 in the embodiment of FIG. 18 may require less wire 1854 to be used than in the embodiment of FIGS. 1-16 and require a potentially less circuitous routing of the wires throughout the base 1702, potentially decreasing the assembly cost of the oral irrigator and creating a more robust design overall. This placement of the circuit board 1831 in this location is near the center of the oral irrigator base 1702 to help protect the circuit board 1831 against electrostatic discharges which may impact the outer walls of the main enclosure.

Power Button Structure

Figure 19A:
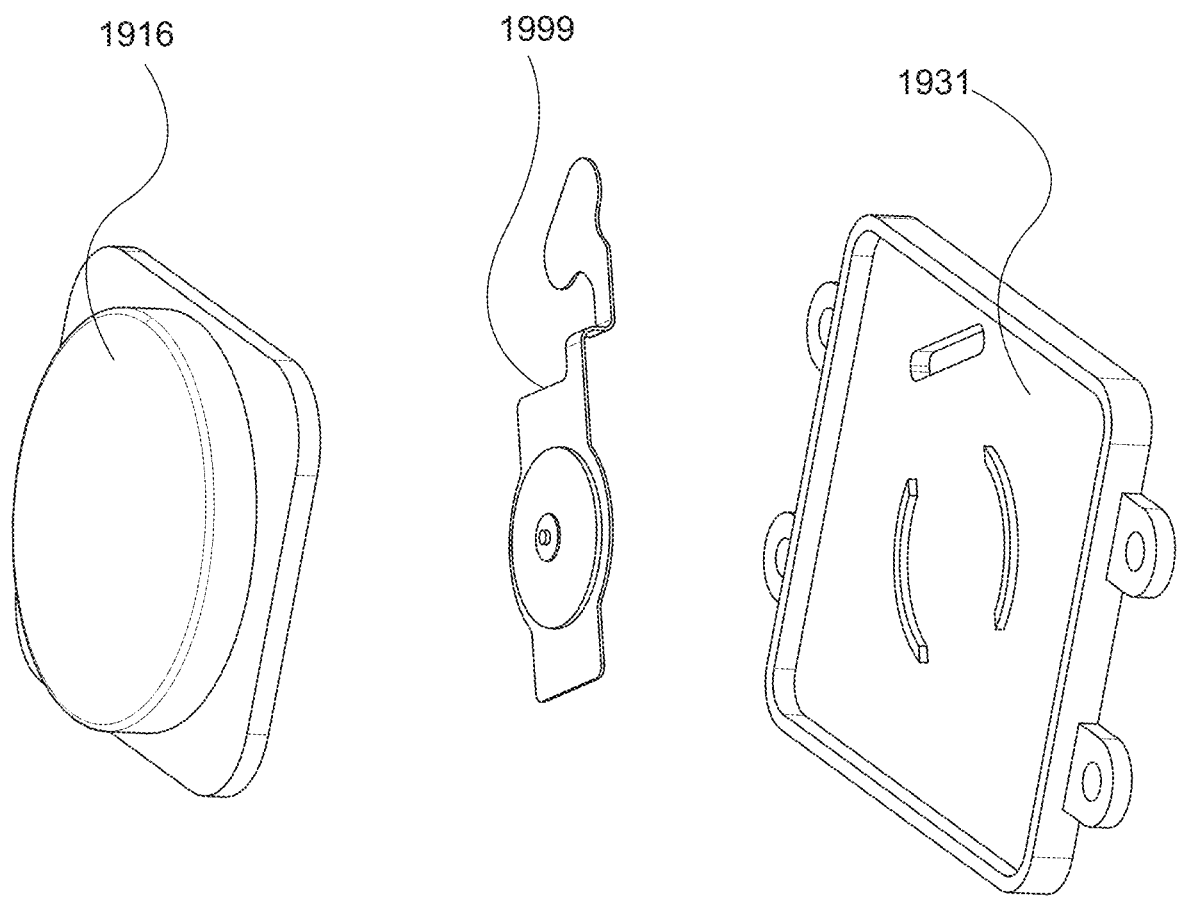
FIG. 19A is an exploded top isometric view of a power button assembly of the oral irrigator of FIG. 17.
Figure 19B:
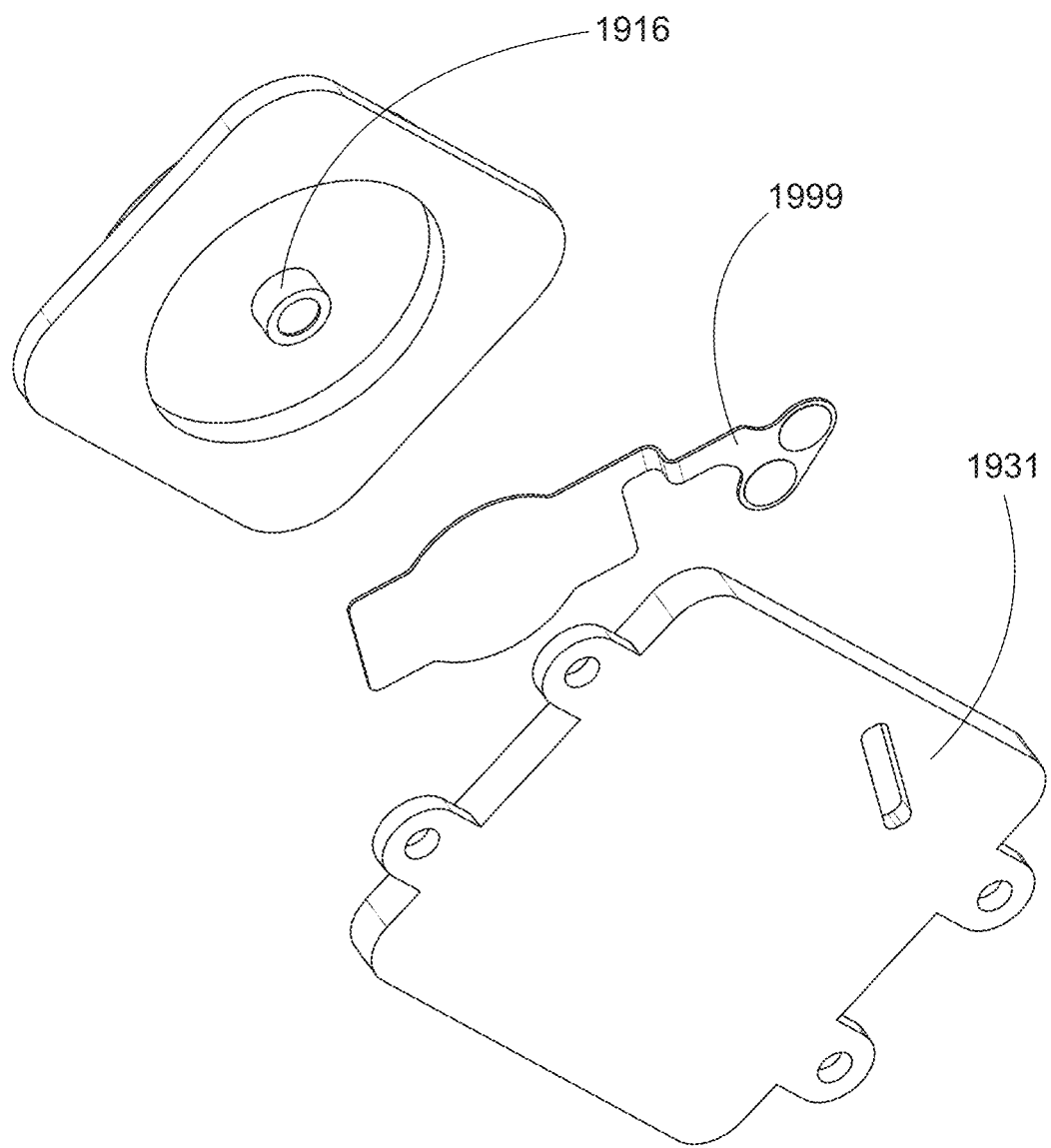
FIG. 19B is an exploded bottom isometric view of a power button assembly of the oral irrigator of FIG. 17.

An alternate embodiment of the structure surrounding the power button 1916 is shown in FIGS. 19A and 19B. The power button 1916 may include a flexible PCB 1999 with a dome switch and an adhesive backing. The flexible PCB 1999 is installed between the button 1916 and the bracket 1931, and the adhesive side of the flexible PCB 1999 may be positioned adjacent bracket 1931. The flexible PCB 1999 may help provide the user with a tactile feel when the button 1916 is depressed, which may help enhance the user experience. A silicone seal may be adhesively coupled to the button 1916. When assembled, the button 1916 is sandwiched between the bracket 1931 and the upper housing 194, with the outer edge of the silicone seal compressed between the bracket 1931 and the housing 194. This seal further protects the internal components connected to the power button 1916 from exposure to liquids that may inadvertently contact the power button 1916.

Power Connector Connection

An alternate embodiment for the male power connector socket 136 of the base 102 within the power connector aperture 210 is also provided. With reference to FIG. 18, and similar to the original embodiment shown in FIG. 3C, the power connector aperture 1810 is defined through the back wall 1870 and extends into the dry compartment 1804 of the base 1702. The male power connector socket 1836 is installed within the power connector aperture 1810, and has two pins 1898. After installation, the male power connector socket 1836 is then connected to the base 1702 by way of welding, applying epoxy or other waterproof adhesive between the components, using a press fit, or other similar techniques. In an example where the male power connector socket 1836 is welded to the base 1702, a waterproof membrane is created. The male power connector socket 1836 may be manufactured using an insert molding technique, which may create a male power connector socket 1836 that has good wear resistance and tensile strength. In addition, the male power connector socket 1836 may be welded to the power block cavity 1774, increasing the strength and durability of the connection of the power connector socket 1836 to the power block cavity 1774 and the base 1702. In addition, the welding and insert molding technique may create waterproof connections that would otherwise require additional seals, which would otherwise require additional costs and assembly time. Furthermore, these features may be desirable as the male power connector socket 1836 will be repeatedly exposed to wear through repeated engagement and disengagement with the female power connector plug 1799 of the power assembly 1734 with the oral irrigator. With reference to FIGS. 17 and 18, the female power connector plug 1799 is attached to the power cord 1712 connected to the inverter and mechanically and electrically couples with the male power connector socket 1836 to provide an electrical connection to allow the transfer of electrical power through the power assembly 1734 to the oral irrigator 1700.

Vibrational Dampening

The embodiment shown in FIG. 18 may also feature an alternate connection between the motor 1818 and the base 1702. The motor 1818 may be connected to the base 1702 through a bracket 1897. To dampen vibrations transmitted between the motor 1818 and the base 1702, an O-ring 1896 may be installed between the motor and the bracket 1897. In addition to dampening vibrations, the O-ring 1896 may also help shift the ambient resonant frequency of the bracket away from an ambient resonant frequency of the oral irrigator 1700 during operation to further decrease potential vibrations transmitted between the motor 1818 and the base 1702 and reduce the possibility of the system operating at its natural frequency or a multiple thereof during use. While not shown, it is also contemplated that the pump assembly 214 may be modified with additional vibration reduction components. This may help decrease vibrations and shift any resonant frequencies that may exist between the pump assembly 214 and its connection to the base 1702.

Piston and Wet/Dry Compartment Seal

Figure 26:
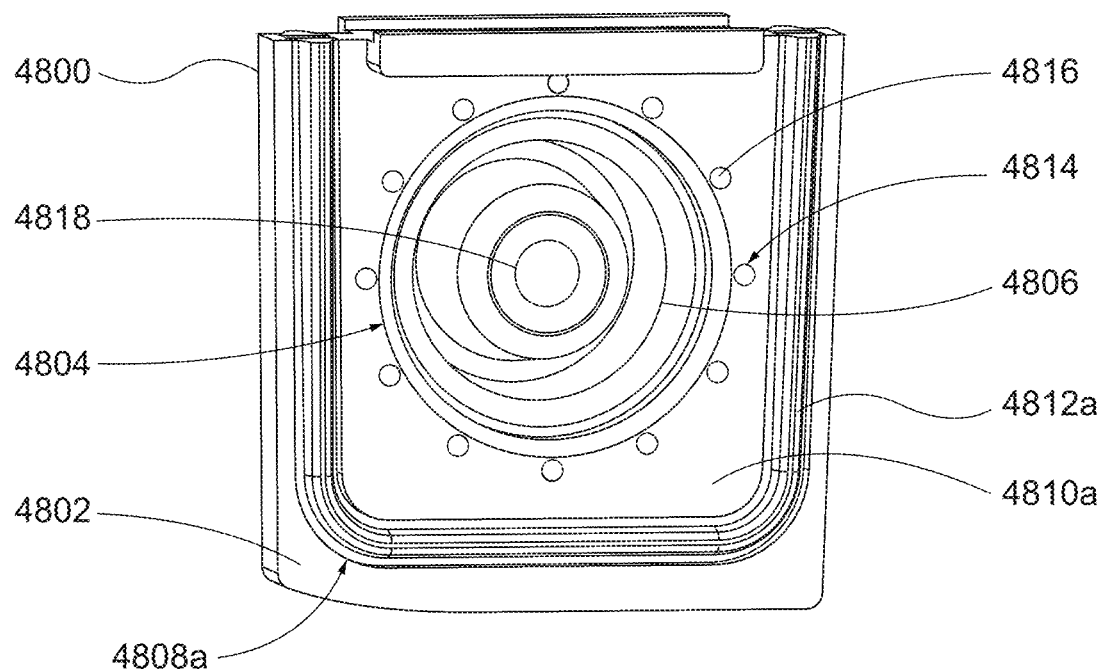
FIG. 26 is a right side isometric view of a diaphragm seal of the oral irrigator of FIG. 17.
Figure 27:
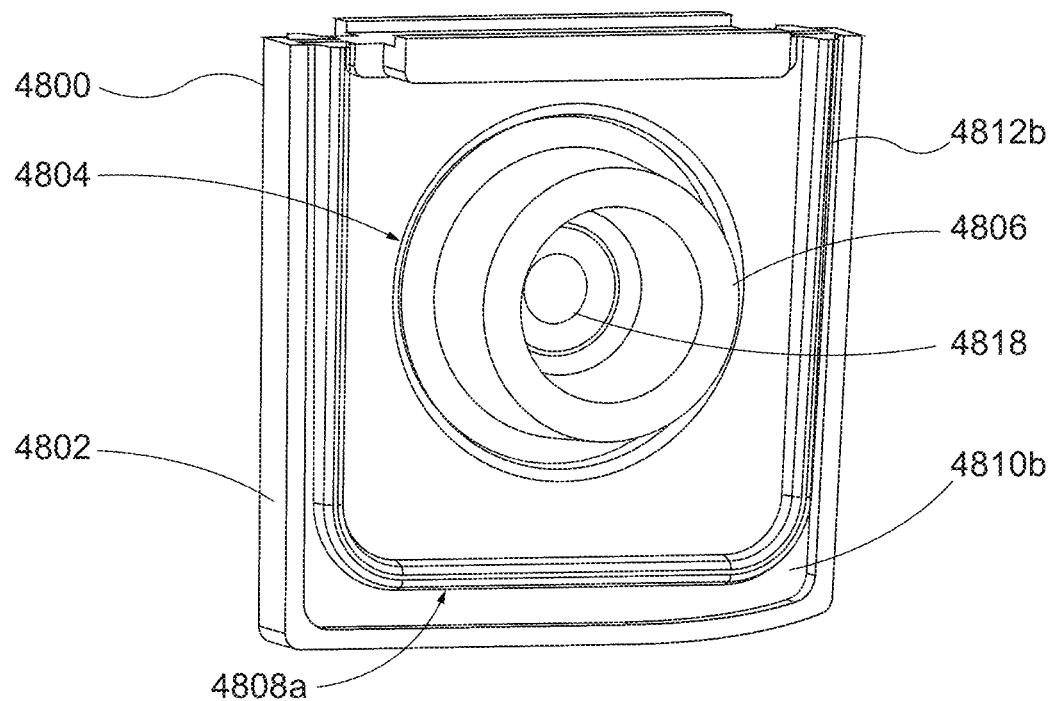
FIG. 27 is a left side isometric view of the diaphragm seal of FIG. 26.

Another embodiment for a diaphragm seal 4800 for use in the design of the irrigator base in FIG. 18 is shown in greater detail in FIGS. 26 and 27. The diaphragm seal 4800 may be manufactured using an overmold-type design in which a hard plastic frame 4802 defines a center aperture 4804 across which the bellows 4806 extends. Additionally, U-shaped channels 4808a, 4808b may be form directly opposite each other in opposing faces of the frame 4802, i.e., a dry face 4810a (facing the motor and electrical compartments) and a wet face 4810b (facing the compartment with the pump and valve components). A number of pass-through holes (not visible) may be formed spaced apart from each other along the lengths of the U-shaped channels 4808a, 4808 to extend between the U-shaped channels 4808a, 4808. A pair of U-shaped bead seals 4812a, 4812b may be positioned within the U-shaped channels 4808a, 4808 and extend above a surface of each of the dry face 4810a and the wet face 4810b, respectively. Additionally, a number of through holes 4814 may be formed in the plastic frame 4802 spaced apart surrounding the center aperture 4804 and the bellows 4806.

In these examples, the bellows 4806 and the bead seals 4812a, 4812b may be manufactured by overmolding a flexible rubber, such as NBR or HNBR or other nitrile, on the hard plastic frame 4802. During the molding process, the injected rubber may flow through the pass-through holes in the channels 4808a, 4808 to form the bead seals 4812a, 4812b. The rubber ma further coat the frame on the dry face 4810a of the frame 4802 in order to connect the bellows 4806 to the bead seal 4812a. The rubber may further fill the through holes 4814 to form a number of plugs 4816 that provide additional structural support to hold the bellows 4806 in place as it rolls back and forth under the action of the connecting rod 2036. The bead seals 4812a, 4812b may extend above the each of the faces 4810a, 4810b to extend a distance between the top surface of each that is slightly larger than the width of the C-channel in the C-channel bracket 1801.

The embodiment of FIG. 18 may also feature an alternate structure to secure the diaphragm seal 4800 within the base 1702. The partition wall 1800 may feature a C-channel bracket 1801 to hold the diaphragm seal 4800, as opposed to in the embodiment of FIG. 6C, wherein the first and second sealing plates 488, 490 are clamped together with fasteners, with the edges of the diaphragm seal 480 being clamped therebetween. The overmold diaphragm seal 4800 may be installed into the base by pressing the bead seals 4812a, 4812b into the C-channel of the C-channel bracket 1801 to seal off the slot formed between components. The center ring 4818 of the bellows 4806 will clamp and seal onto the connecting rod maintaining a water-proof seal. The use of the integrated C-channel bracket 1801 may help simplify installation of the diaphragm seal 4800. The use of overmold technique may reduce or eliminate the need to clamp a rubber diaphragm (such as those shown in FIG. 6C) between two plastic parts with fasteners. This may reduce the number of assembly parts, decreasing manufacturing and assembly costs.

The embodiment of FIG. 18 may also feature an alternate structure for connecting the wall 200 of the base 102 to the upper housing 180. The partition wall 1800 forms a portion of the dry compartment 1804, which extends from the male power connector socket 1836 to the pump assembly 1814 and motor 1818 mounting areas. The diaphragm seal 480 forms the additional seal and separation structure between the wet and dry compartments. The partition wall 1800 may take on a different shape than the wall 200 of the prior embodiment, which formed a completely separate compartment from the motor and pump in the prior embodiment. The perimeter wall of the base 1702 and the partition wall 1800 may be secured to the upper housing (not shown) with epoxy glue for mechanical connection and water proofing to ensure the seal and separation of the dry compartments from the wet compartment. Use of such water-proof glue may provide a significant water proofing benefit over merely sonically welding the housing components. Further, the vibration reduction components described above may impede the ability to create a secure sonic weld of the housing components, thus making a water-proof adhesive a more attractive connective option.

Mechanical Power Transmission Assembly

Figure 22A:
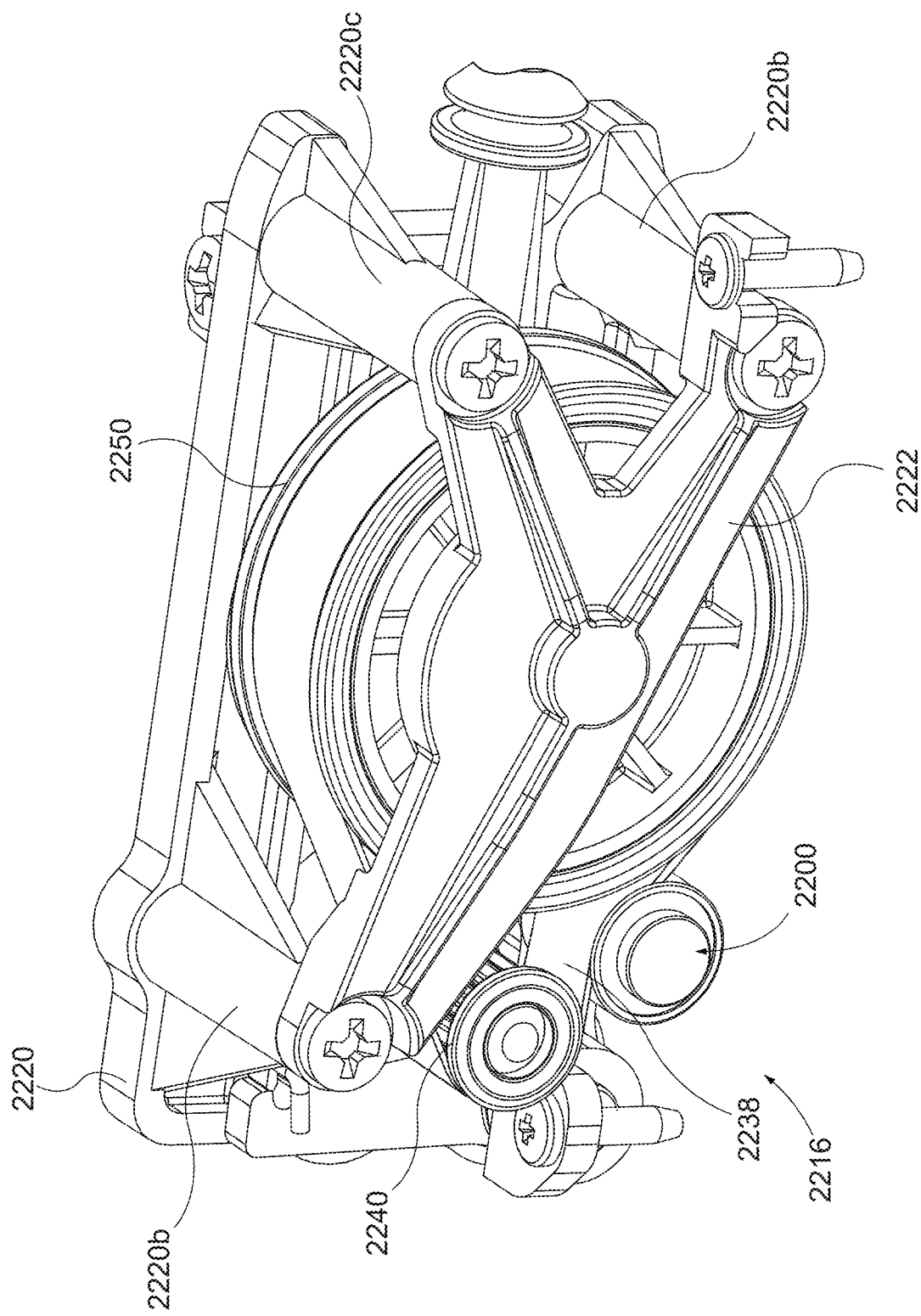
FIG. 22A is an isometric view of an alternate embodiment of a drive assembly.
Figure 22B:
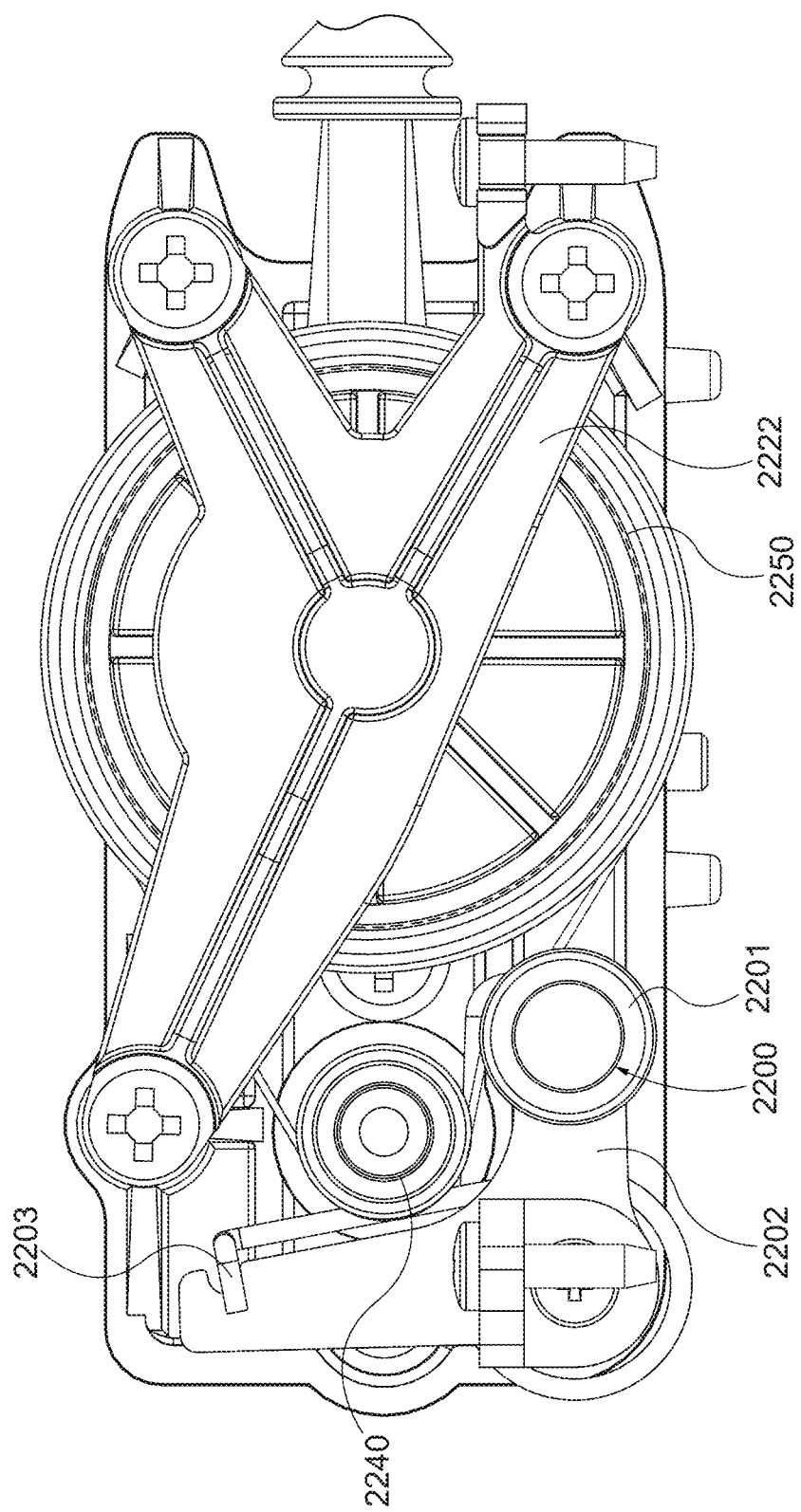
FIG. 22B is a front elevation view of the drive assembly of FIG. 22A.

Another embodiment of a mechanical power transmission assembly is shown in FIGS. 22A and 22B. Similar to the chassis 220 of FIGS. 7A and 7B, a chassis 2200 supports a driven pulley 2250 which is mechanically coupled to a pinion pulley 2240 by a belt 2238. A securing bracket 2222 may help correctly position the pulleys 2240, 2250 and connect the motor 1818 and the belt drive system to the chassis 2200 by way of bosses, 2220a, 2220b, and 2220c. In the embodiment of FIGS. 22A-22B, the bracket 1897 of FIG. 18 may be eliminated, as the securing bracket 2222 acts as a main motor bracket to secure the motor 1818 within the main unit. This allows the motor 1818 to mostly "float" such that vibrational resonance and noise may be reduced. To further reduce vibrational resonance and noise, foam tape may be wrapped about the motor 1818.

A tension assembly 2200 may be used to increase the belt tension of the installed belt 2238 about the pulleys 2240, 2250. The tension assembly 2200 may feature a tension assembly bracket 2202 which couples the tension assembly 2200 to the chassis 2220 and is positioned adjacent to the belt 2238. The tension assembly 2200 may have an idler pulley 2201 and a tension member 2203. The idler pulley 2201 may be positioned such that it is an inside idler, and it contacts the inside of the belt 2238, or a backside or outside idler, where it contacts the outside or backside of the belt 2238. The idler 2201 of FIG. 22B is shown as a backside idler. In some examples, the idler pulley 2201 may be made of bearings with a pin acting as the shaft and may be connected to the tension assembly bracket 2202. When coupled with the tension member 2203, the idler pulley 2201 exerts a force on the backside of the belt 2238, as the tension member 2203 is forced to expand from its normal resting spring state. This force varies as the belt 2238 is rotated by the pinion pulley 2240. The force is smaller when the pinion pulley 2240 is not rotating. The force is increased when the pinion pulley 2240 begins to rotate, as the tension in the belt 2238 increases to transmit rotational power from the pinion pulley 2240 to the driven pulley 2250. The use of a spring, such as tension member 2203, allows the system to adjust to correspond to the belt tension generated from the rotational speed and load transmitted through the belt 2238.

Most belt drive assemblies require either a tension assembly or a method to adjust the center distance between the driver and driven pulleys so that the appropriate belt installation tension may be achieved. Having the ability to adjust the center distance between pulleys requires that the location of at least one of the pulleys is adjustable. This adjustability requirement may increase manufacturing costs, as components may need to be made using tighter manufacturing tolerances, and a larger footprint may be necessary. The belt tension changes when the belt drive is operated as opposed to when it is stationary, and it may vary as the load on the motor changes. The ability to use a spring-loaded tension assembly may be beneficial to help insure that the belt drive is tensioned to the optimum tension given various loading scenarios, particularly in an enclosed case with an inability to access the pulley system to adjust the tension. A belt drive that uses fixed center distances and does not use a tension assembly may result in an improperly tensioned belt drive, which can result in excess noise, poor performance, increased bearing loads on bearings used with the pulleys and the associated driver and driven components, and decreased belt life.

In some cases, the correct use of a tension assembly 2200 may help improve an acoustic attribute of the mechanical power transmission assembly. A properly tensioned belt drive will likely be quieter than an improperly tensioned belt drive. The tension assembly 2200 increases the wrap angle of the belt 2238 about the pinion pulley 2240, which may increase the overall efficiency of the system, as more of the belt is engaged with the pinion pulley 2240 to then transmit power to the driven pulley 2250. In addition, an increase in wrap angle may also increase the overall tension of the belt 2238 when positioned on the pulleys 2240, 2250. The increase of tension may help the belt properly seat against the pulleys such that a more efficient power transmission is achieved. In addition, a properly tensioned, and therefore seated, belt 2238 may decrease the overall noise of the belt drive, as the belt may not slip (if a v-belt or round belt), or the belt teeth will not jump or ratchet on the pulley teeth (if using a synchronous belt). This arrangement may also help improve the overall life of the belt, as slippage and ratcheting may cause unnecessary damage to the belt and result in premature failure.

The tension assembly 2200 may also help decrease overall manufacturing costs of the oral irrigator assembly, as the dimensional tolerances on the pulleys 2240, 2250 may be increased as the tension assembly 2200 can adjust for any changes in center distance based on dimensional changes of the pulleys 2240, 2250. In addition, the tolerances associated with the center distance between the pulleys 2240, 2250 may be slightly relaxed, as the tension assembly 2200 may account for small changes in distance associated with manufacturing tolerances. The tension assembly may also be used to account for the dimensional tolerances associated with the overall belt length and tooth pitch. The problem of potential belt stretch over the life of the belt drive is also mitigated, as a spring loaded tension assembly, such as the tension assembly 2200, may be able to account for an increase in belt length due to stretching.

Figure 20:
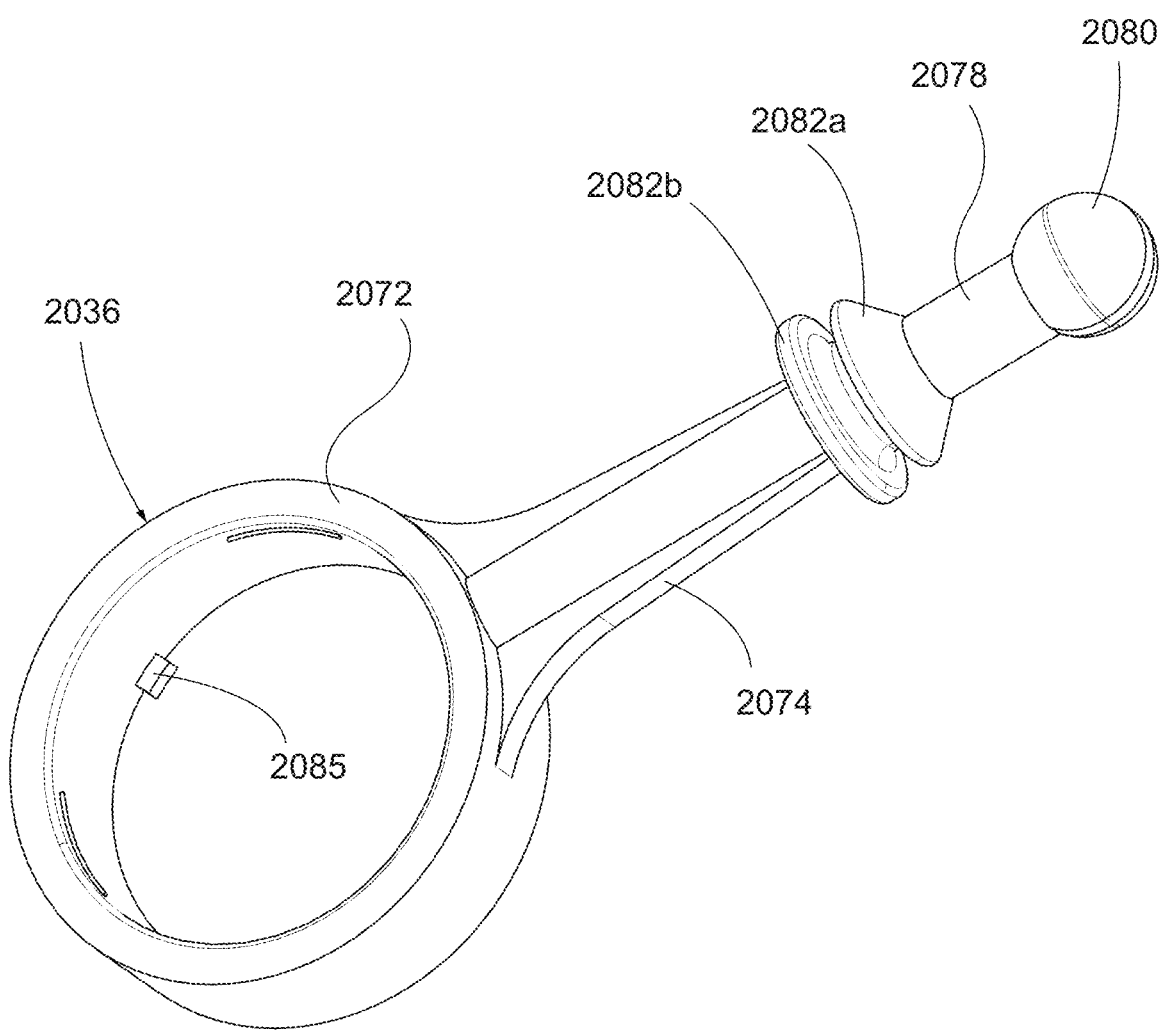
FIG. 20 is a front isometric view of a connecting rod of the oral irrigator of FIG. 17.

An alternate connecting rod 2036 is shown in FIG. 20. The connecting rod 2036 includes a connecting end 2072 defining a cylindrical ring having a plurality of tabs 2085 extending inward from an interior surface of the connecting end 2072. The connecting end 2072 is shaped and dimensioned to be received around the bearing race 252 (see FIG. 7B) and thereby around the engagement boss 2160 (see FIG. 21) to rotate within the cylindrical ring of the connecting end 2072. An arm 2074 extends from the connecting end 2072. The arm 2074 transitions to a terminal end 2078 having a ball 2080. The arm 2074 of the connecting rod 2036 may be straight, rather than featuring the angled bend 276 in the middle portion thereof as in the first embodiment of the connecting rod 236. The alternate spacing of the internal components within the base 1702 allows for the connecting rod 2036 to be straight, as opposed to the connecting rod 236 of FIGS. 9A and 9B, which required the angled bend 276 so that the reduced form factor of the oral irrigator could be maintained. The straight arm 2074 of the connecting rod 2036 still allows the connecting rod 2036 to pass through the center of the diaphragm seal 4818 between wet and dry compartments. The diaphragm seal 4818 is positioned between the two sealing flanges 2082b and 2082a. The overall form factor of the base 1702 is not increased with the connecting rod 2036 being straight, such that the desired user experience of a reduced form factor oral irrigator is still maintained.

Figure 21:
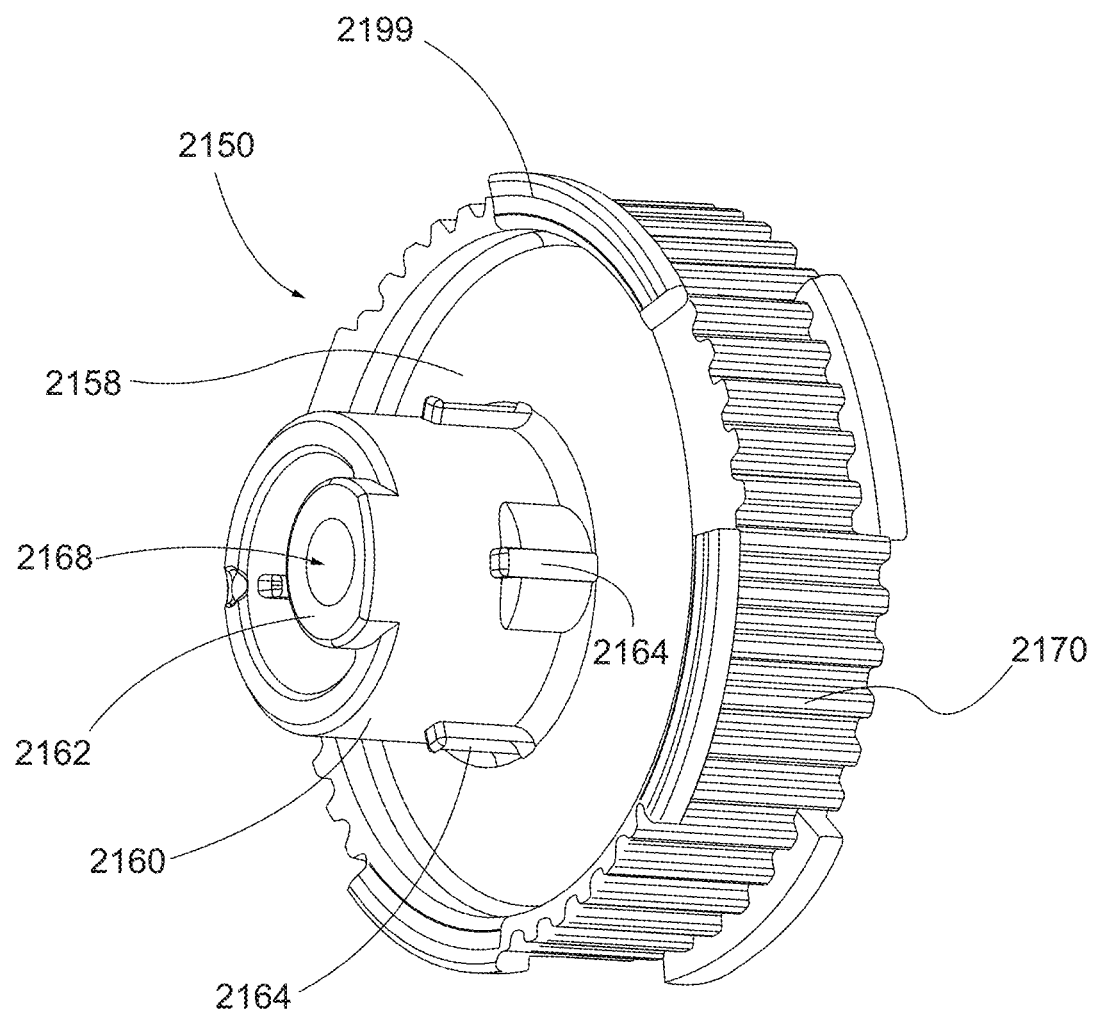
FIG. 21 is a front isometric view of a driven pulley of the oral irrigator of FIG. 17.

An alternate embodiment may also feature a driven pulley 2150 as shown in FIG. 21. Similar to driven pulley 250 of FIGS. 8A-8B, the driven pulley 2150 may be relatively cylindrical with a plurality of teeth 2170 or grip elements for enhancing frictional engagement with the belt 238. The driven pulley 2150 includes an engagement boss 2160 that extends from a first surface 2158. The engagement boss 2160 may be formed as a cylindrical protrusion and many include one or more ribs 2064 extending lengthwise on an outer surface thereof. The bearing race 252 may seat around the engagement boss 2160 and is held in place by the ribs 2064. A pin aperture 2168 may be aligned with the center of the axis of the driven pulley 2150 and the engagement boss 2160 may be offset relative thereto to form an eccentric post. The engagement boss 2160 extends away from the first surface 2158 and, in some embodiments, the pin structure 262 may be arranged within the engagement boss 2160 to increase the length of the pin aperture 2168, extending through the height of the boss 2160. In some embodiments, the pin structure 2162 may be longer than the height of the boss 2160.

The driven pulley 2150 in this embodiment as shown in FIG. 21 may be a single molded pulley with teeth 2170 and integrated staggered flanges 2199 formed on opposite sides of the ends of the teeth 2170. In one embodiment, a staggered flange 2199 may be formed so that a flange structure exists next to only some of the teeth 2170 surrounding the driven pulley 2150. In some embodiments, the staggered flanges 2199 on each side of the driven pulley 2150 are aligned with each other. In some embodiments, the staggered flanges 2199 on each side of the driven pulley 2150 may be offset from each other, as shown in FIG. 21. The staggered flanges 2199 may be used to help initially determine the alignment of the drive assembly 216 during installation and also help prevent the belt 238 from tracking off the drive assembly 216 while the belt 238 is rotating due to belt tracking forces, thereby preventing a potential failure mode of the oral irrigator 1700. The molded driven pulley 2150 with staggered flanges 2199 may improve the overall oral irrigator 1700 by eliminating the need for a separate flange. The elimination of the separate flange (as shown with flange 248 and original driven pulley 250 in FIG. 7B) may decrease the overall production cost of the driven pulley 2150 by eliminating a component with a certain individual part cost and the production time attributed to assembling the original driven pulley 250 and flange 248.

Pressure Control Slider

Figure 29:
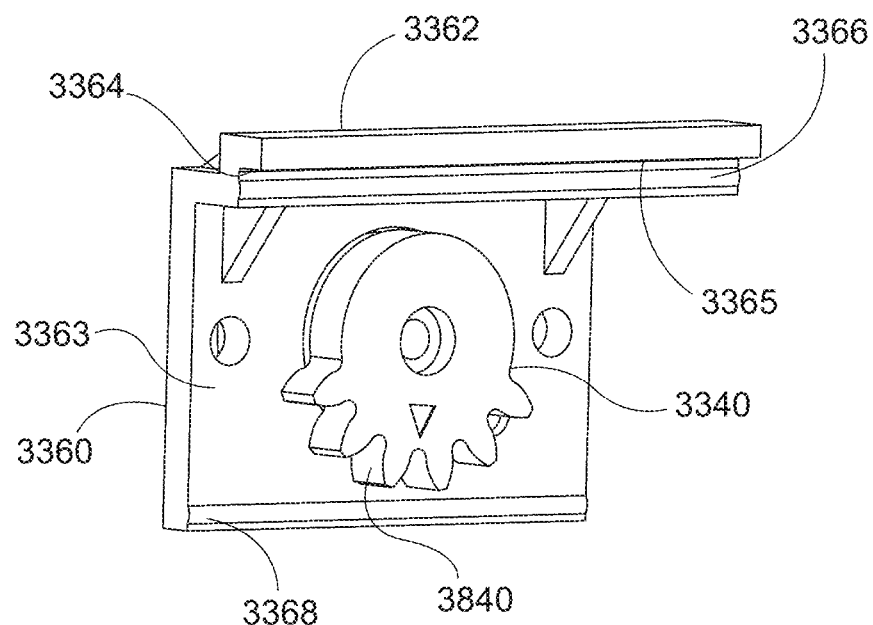
FIG. 29 is an isometric view of a gear assembly attached to the pump assembly which interfaces with the rack gear of FIG. 28.
Figure 28:
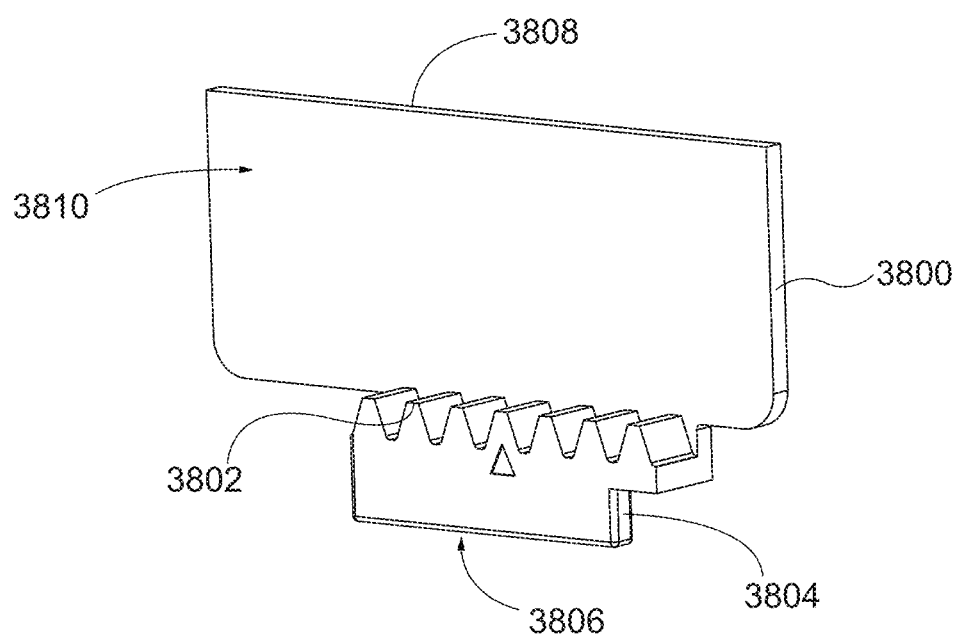
FIG. 28 is an isometric view of an actuator with a rack gear from the oral irrigator of FIG. 17.
Figure 30:
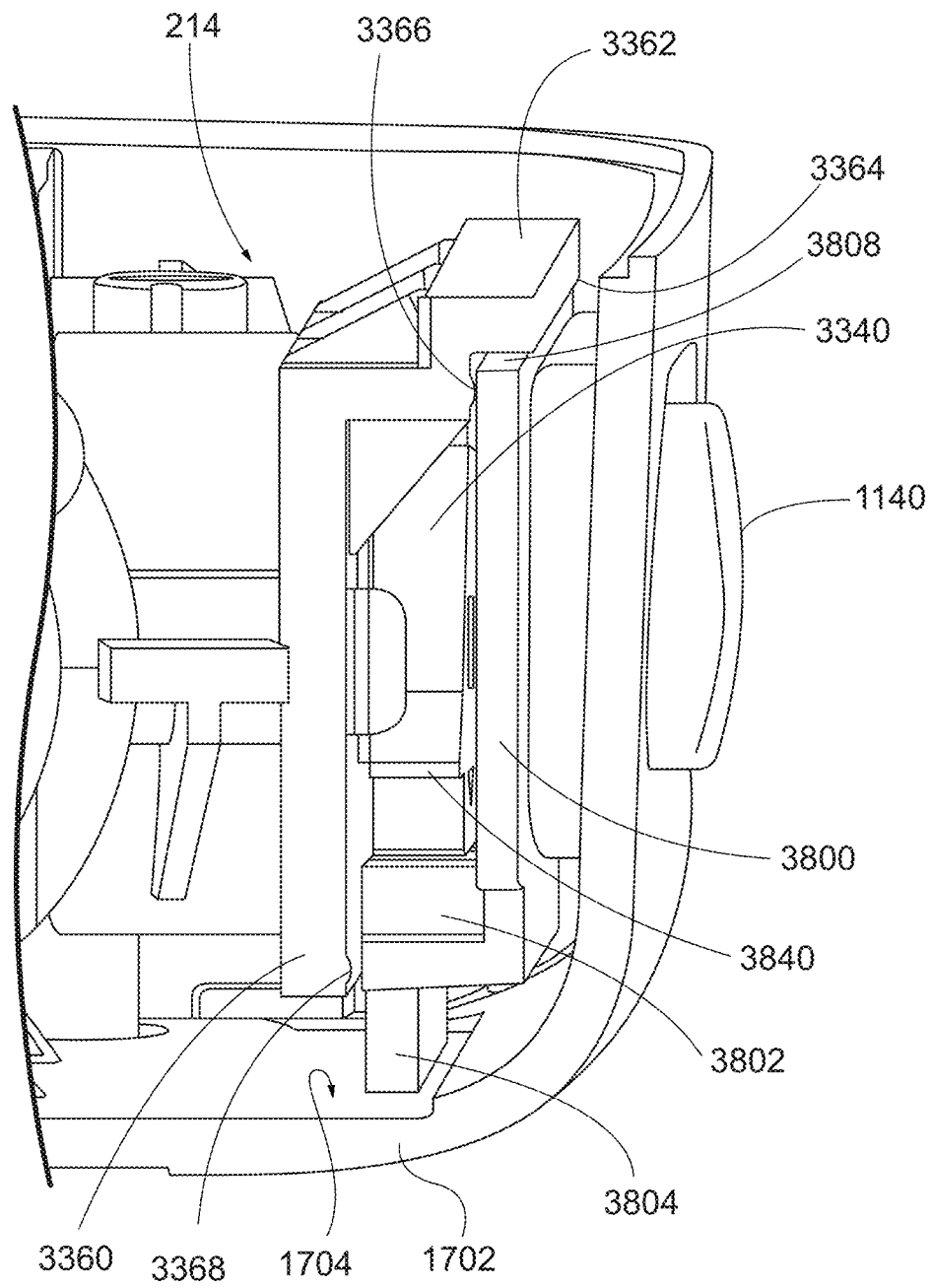
FIG. 30 is a front isometric view in cross section of the actuator of FIG. 28 interfacing with the gear assembly of FIG. 29.

In the embodiment of FIG. 18, the rack 3800 and actuator 1140 may be manufactured as a single element, and may be integrated to slide with respect to the base 1702 and the pump assembly 214 as shown in greater detail in FIGS. 28-30. As in the prior embodiment, the teeth 3802 of the rack 3800 interfaces with the teeth 3840 of the gear 3340 connected to the pump assembly 214. In this embodiment, a gear bracket 3360 is mounted to the pump assembly 214 and the gear 3340 is mounted thereon via a shaft extending therethrough to the pump assembly 214. The teeth 3840 of the gear 3340 need extend entirely around the circumference of the gear 3340, but rather only along a bottom arc as the travel distance of the rack 3800 need not interfaces with additional teeth or cause additional rotation of the gear 3340. The gear bracket 3360 may be formed as a vertical wall 3363 with a planar face and a horizontal shelf 3362 extending normally from the planar face at a top edge of the vertical wall 3363. The shelf 3362 may be formed with a step 3364. A first linear boss 3366 may be formed on a vertical face of the step 3364 and lintel 3365 may extend outward from the vertical face over the first linear boss 3366. A second linear boss 3368 may be formed along the bottom edge of the vertical wall 3363 parallel to the first linear boss 3366. The absence of teeth on the top edge of the gear 3340 allows additional room for the extension of the shelf 3362.

As noted above, the rack 3800 and actuator 1140 may be formed as a single piece. The actuator 1140 may extend normally from a planar guide wall 3810. The teeth 3802 of the rack 3800 may be positioned adjacent to a bottom edge of the inner face of the guide wall 3810 extending upward for engagement with the teeth of the gear 3340 as shown in FIG. 30. A kick plate 3804 may extend from a bottom edge of the bed from which the teeth 3802 extend. The kick plate 3804 may be oriented parallel to the guide wall 3810 and offset from the plane of the inner face by a portion of the width of the teeth 3802.

When the actuator 1140 is assembled in the base 1702 and the teeth 3802 of the rack 3800 mesh with the teeth 3840 of the gear 3340, a bottom edge 3806 of the kick plate 3804 seats upon a planar recess 1704 in the base 1702 and travels along the planar recess 1704 as the actuator 1140 is moved laterally back and forth. Similarly, the top edge of the guide wall 3810 seats against the underside of the lintel 3365 of the step 3364. In this configuration, possible vertical movement of the rack 3800 is constrained. Additionally, the inner face of the guide wall 3810 seats against the first linear boss 3366 on the step 3364. Similarly, the inner face of the kick plate 3804 seats against the second linear boss at the bottom of the gear bracket 3360. The rack 3800 thereby glides along the first and second linear bosses 3366, 3368 as the actuator 1140 is moved back and forth This embodiment may be more robust as fewer elements are assembled together and move with respect to each other.

Hose Latch Assembly

Figure 23A:
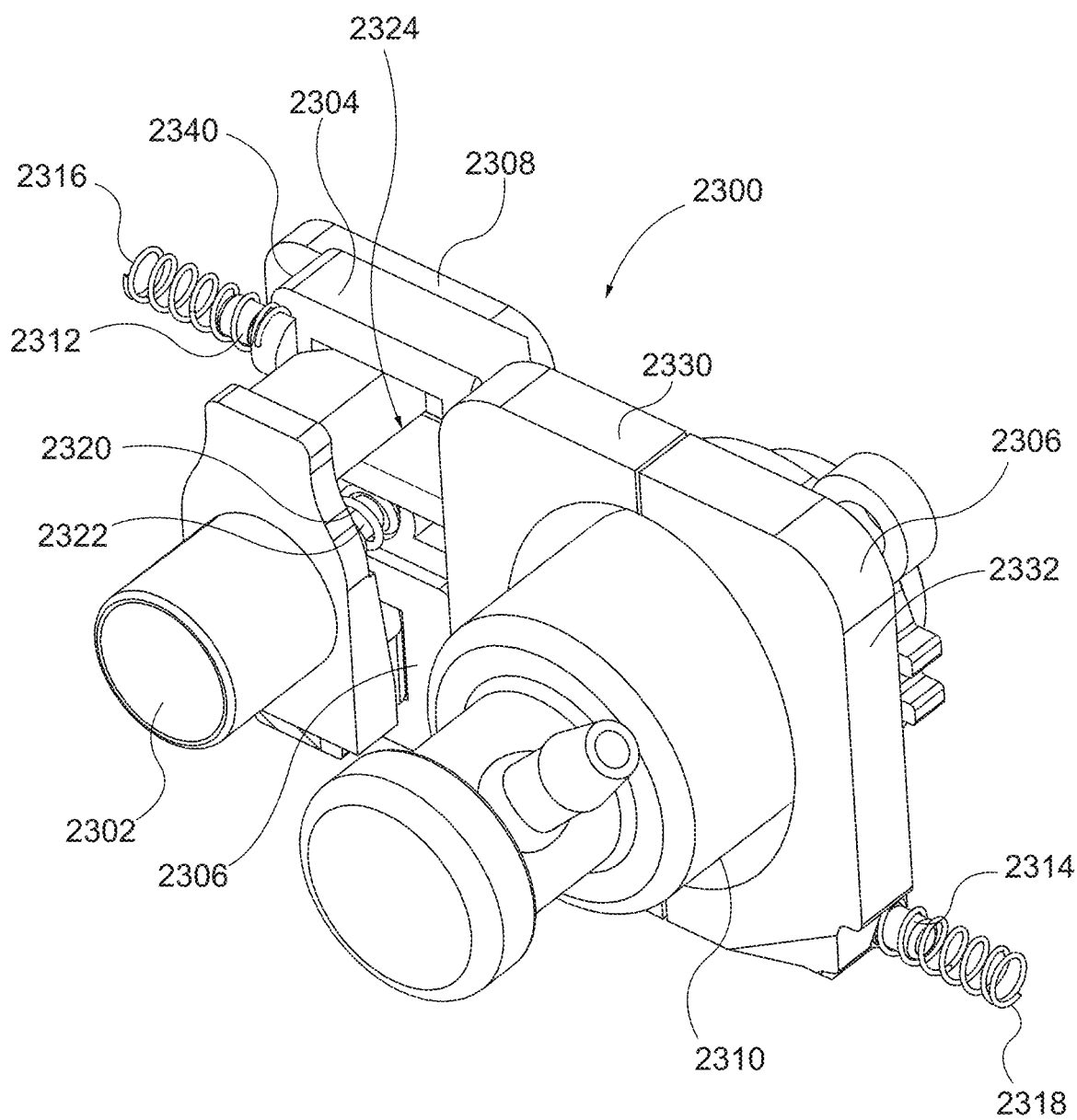
FIG. 23A is a front isometric view of an alternate embodiment of a hose latch assembly.
Figure 23B:
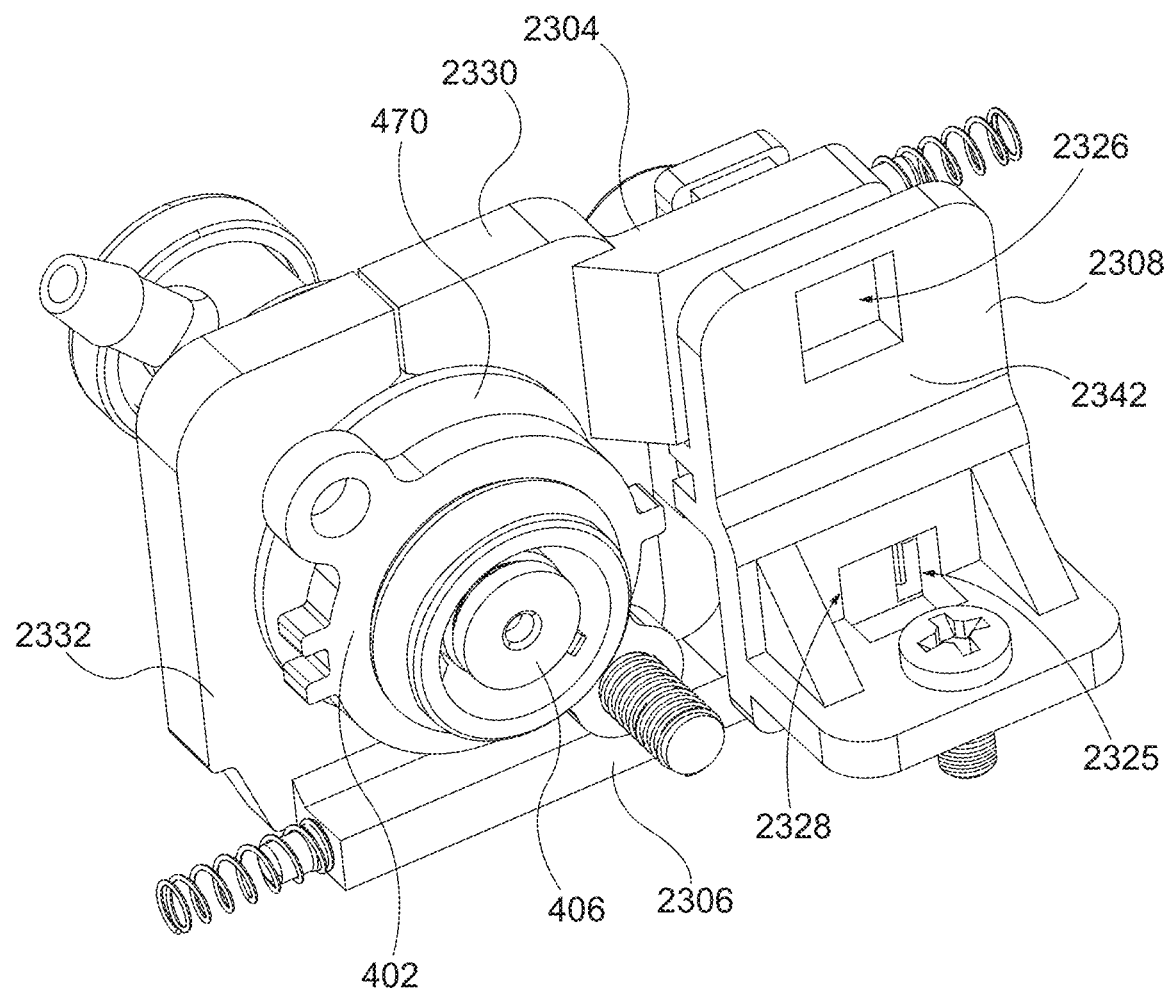
FIG. 23B is rear isometric view of the hose latch assembly of FIG. 23A

An alternate hose latch assembly 2300 is shown in FIGS. 23A and 23B. Instead of the leaf spring 430 and arms latch arms 436a, 436b of FIGS. 6C, and 10, the hose latch assembly 2300 utilizes a left slider 2304 and a right slider 2306 which adjustably encase the hose connector 2310 to fluidly connect the hose connector 2310 to the reservoir 104. The left slider 2304 has a post 2312 extending from a side of the left slider 2304 around which a bias element 2316 may be positioned. The left slider 2304 may also have a window 2324 which is a through-hole from a front surface to the rear surface. The window 2324 may be generally rectangular shaped. The left slider 2304 may also have a hose connector bracket 2330, which may be configured to engage with a portion of the hose connector 2310. In some examples, the hose connector bracket 2330 of the left slider 2304 may be hemispherical with a concave shape curved away from the hose connector 2310.

The right slider 2306 may be similar in shape to the left slider 2304, with a post 2314 extending from a side of the right slider 2304 and a bias element 2318 positioned about the post 2314. The right slider 2306 may also have a window 2325 which is a through-hole from a front surface of the right slider 2306 to a rear surface. The window 2325 may be generally rectangular shaped. The right slider 2306 may also have a hose connector bracket 2332. In some examples, the hose connector bracket 2332 of the right slider 2306 is shaped similarly to and positioned symmetrically opposite the hose connect bracket 2330 of the left slider 2304.

An eject bracket 2308 may have a front face 2340 and a rear face 2342 opposite the front face 2340. As shown in FIG. 23B, the eject bracket 2308 has an upper window 2326 positioned vertically above a lower window 2328. The windows 2326, 2328 may be rectangular shaped through-holes which extend from the front face 2340 to the rear face 2342.

Figure 24:
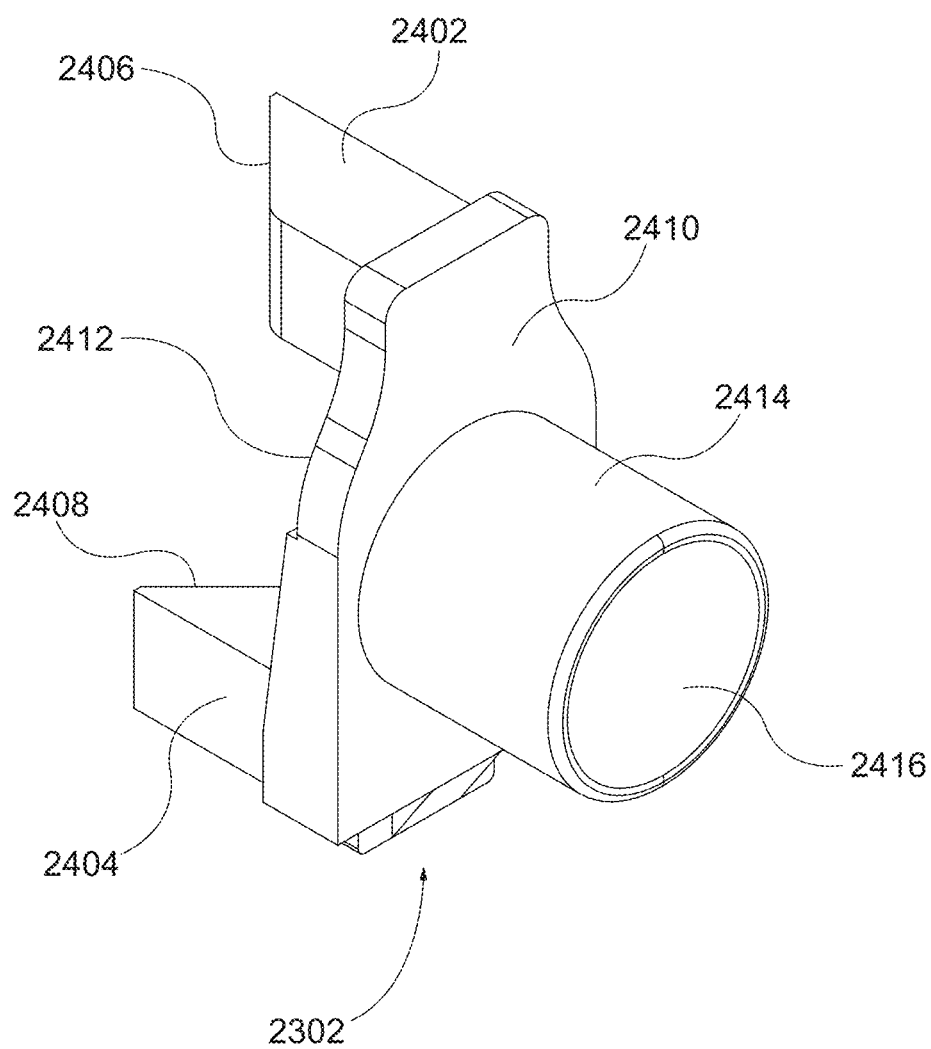
FIG. 24 is an isometric view of an alternate embodiment of an eject button.

As shown in FIG. 24, the eject button 2302 may feature a front face 2410 opposite a rear face 2412, with a left engagement post 2402 and a right engagement post 2404 extending from the rear face 2412. In some examples, the left engagement post 2402 may be positioned vertically above the right engagement post 2404. A user engagement protrusion 2414 may extend from the front face 2410. In some examples, the user engagement protrusion 2414 may be cylindrical shaped with a user engagement surface 2416 on an end opposite the front face 2410. The user engagement surface 2416 may be concave and curved away from the front face 4210.

The left engagement post 2402 may be rectangular shaped with an end of the post 2402 opposite the rear face 2412 being a sloped engagement surface. The right engagement post 2404 may be similarly shaped to the left engagement post 2402, but with a sloped engagement surface 2408 that is angled opposite the sloped engagement surface 2406 of the left engagement post 2402.

When the hose latch assembly 2300 assembled, the left slider 2304 and the right slider 2306 are positioned adjacent each other, with the hose connector bracket 2332 of the right slider 2306 adjacent to and contacting the hose connector bracket 2330 of the left slider 2304, forming a circular shape with a diameter smaller than a largest diameter of the external flange 470 (see FIG. 10) of the hose connector 2310. The left engagement post 2402 of the eject button 2302 extends through the left slider window 2324 of the left slider 2304. The right engagement post 2404 of the eject button of the eject button 2303 extends through the right slider window 2325 of the eject button. The rear face 2412 of the eject button 2412 may be adjacent and contact the bias element 2320 that is adjacent the eject bracket 2308. The eject bracket 2303 may be positioned adjacent the left slider 2304 and on a side opposite of the eject button 2302. The left engagement post 2404 of the eject button 2302 may be aligned with the upper window 2326 of the eject bracket 2308. The right engagement post 2404 of the eject button 2302 may be aligned with the lower window 2328 of the eject bracket 2308.

When the hose latch assembly 2300 is use, a user may engage the user engagement surface 2416 of the eject button 2303 to release or install the hose connector 2310. A user may contact the user engagement surface 2416 of the eject button 2308 to compress the bias element 2320 positioned between the eject button 2302 and the front face 2340 of the eject bracket 2308. The compression of the bias element 2320 allows the eject button 2302 to move toward the eject bracket 2308. This movement causes the sloped engagement surface 2406 of the left engagement post 2402 of the eject button 2302 to contact an edge of the left slider window 2324 of the left slider 2304, forcing the left slider 2304 to compress the bias element 2316. As the button 2302 is further compressed, the left slider 2304 further compresses the bias element 2316, and the left slider 2304 is shifted left with respect to the eject button 2308. This causes the hose connector bracket 2330 to shift to the left as well and away from the hose connector 2310. The left engagement post 2404 of the eject button 2302 may then extend into the upper window 2326 of the eject bracket 2308.

The movement of the eject button 2302 causes a similar movement in the right slider 2306 in an opposite direction, to the right, as the left slider 2304 is forced to move left. As the eject button 2302 is depressed toward eject bracket 2308, the sloped engagement surface 2408 of the right engagement post 2404 contacts an edge of the right slider window 2325 of the right slider 2306. This contact forces the right slider 2306 to compress the bias element 2318, and the right slider 2306 is shifted away from the left slider 2304. As the eject button 2302 is further depressed, the right engagement post 2404 continues to contact the right slider window 2325 and force the right slider 2306 away from the left slider 2304. As the right slider 2304 is moved to the right, the hose connector bracket 2332 of the right slider moves away from the hose connector 2310. Eventually, the spacing between the hose connector bracket 2330 of the left slider 2304 and the hose connector bracket 2332 of the right slider 2306 is large enough so that the flange 470 of the hose connector 2310 may be released or installed from the hose latch assembly 2300.

When a user is not contacting the eject button 2302, the hose latch assembly 2300 is biased so that the left slider 2304 and the right slider 2306 are biased to contact each other. This allows for an installed hose connector 2310 to remain fluidly connected to the reservoir 104 without the user engaging the eject button 2302. In addition, the use of the semi-circular shape of the hose connector brackets 2330. 2332 block a user's view into the oral irrigator assembly when the hose is not connected, therefore potentially enhance as aesthetic aspect of the unit.

CONCLUSION

The foregoing description has broad application. For example, while examples disclosed herein may focus on a portable, reduced form factor irrigator, it should be appreciated that the concepts disclosed herein may equally apply to other irrigating devices, such as large countertop units or handheld units. Accordingly, the discussion of any example is meant only to be exemplary and is not intended to suggest that the scope of the disclosure, including the claims, is limited to these examples.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order, and relative sizes reflected in the drawings attached hereto may vary.

The above specification, examples, and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A handle for an oral irrigator for directing a focused stream of fluid, the handle comprising:
a housing having a first end and a second end, the housing comprising:
a front housing half;
a rear housing half comprising a convex outer wall; and
a slot formed in the convex outer wall of the rear housing half, the slot comprising:
two opposing walls spaced apart from each other; and
a transverse wall at a terminal interior end of the opposing walls such that the convex outer wall of the housing is open to the slot at lateral sides of the two opposing walls and at a base end of the opposing walls opposite the transverse wall;
a fluid tip coupled to the first end of the housing; wherein:
the slot is positioned adjacent to a center of mass of the handle;
the slot is configured to receive a portion of a reservoir wall of the oral irrigator; and
the slot extends upwards and inwards towards the first end of the housing and towards an internal cavity of the handle defined by the housing, wherein an interior surface of the housing defines an angled wall extending towards a longitudinal axis of the housing, wherein the angled wall is defined by the transverse wall of the slot, and wherein the handle is configured to hang via the slot with the fluid tip positioned above the housing.

2. The handle of claim 1, wherein the two opposing walls are planar.

3. The handle of claim 1, wherein the two opposing walls are parallel.

4. The handle of claim 3, wherein the two opposing walls are planar.

5. The handle of claim 1, wherein the handle extends from a first end to a second end in a generally elongate form along the longitudinal axis and the opposing walls defining the slot extend at an angle with respect to the longitudinal axis.

6. The handle of claim 1, wherein the slot is positioned such that a length of the slot is centered between a length of the handle from a base end to the first end where the fluid tip attaches to the handle.

7. The oral irrigator of claim 1, further comprising a fluid tube extending through the housing, wherein the fluid tube is routed around the angled wall as it extends between the first end of the housing and the second end of the housing.

8. A handle for an oral irrigator for directing a focused stream of fluid, the handle comprising:
a housing having a first end and a second end, the housing comprising:
a front housing half;
a rear housing half comprising a convex outer wall; and
a slot formed in the convex outer wall of a rear portion of the rear housing half, wherein the convex outer wall is open to the slot, the slot comprising:
two opposing walls spaced apart from each other; and
a transverse wall at a terminal interior end of the opposing walls such that the convex outer wall of the housing is open to the slot at lateral sides of the two opposing walls and at a base end of the opposing walls opposite the transverse wall;
wherein:
the slot is positioned adjacent to a center of mass of the handle;
the slot is configured to receive a portion of a reservoir wall of the oral irrigator; and
the slot extends upwards and inwards in a direction towards the first end of the housing and towards an internal cavity of the handle defined by the housing, the slot defining an angled wall on an interior surface of the housing, the angled wall extending towards a longitudinal axis of the housing, and wherein the oral irrigator is configured to hang via the slot with a fluid tip positioned above the housing.

9. The handle of claim 8, wherein the two opposing walls are parallel and planar.

10. The handle of claim 8, wherein the handle extends from a first end to a second end in a generally elongate form along the longitudinal axis and the slot extends upwards and inwards at an angle with respect to the longitudinal axis.

11. The handle of claim 8, wherein the slot is positioned such that a length of the slot is centered between a length of the handle from a base end to a top end where the fluid tip attaches to the handle.

12. An oral irrigator for directing a focused stream of fluid, the oral irrigator comprising:
a handle comprising:
a housing having a first end, a second end, and a rear housing half comprising a convex outer wall, the housing comprising:
a slot formed in the convex outer wall of the rear housing half, the slot comprising:
two opposing walls spaced apart from each other; and
a transverse wall at a terminal interior end of the opposing walls such that the convex outer wall of the rear housing half is open to the slot at lateral sides of the two opposing walls and at a base end of the opposing walls opposite the transverse wall;
wherein:
the slot is positioned adjacent to a center of mass of the handle;
the slot is configured to receive a portion of a reservoir wall of the oral irrigator; and
the slot extends upwards and inwards towards the first end of the housing and towards an internal cavity of the handle defined by the housing, wherein an interior surface of the housing defines an angled wall extending towards a longitudinal axis of the housing, wherein the angled wall is defined by the transverse wall of the slot, and wherein the oral irrigator is configured to hang via the slot in an upright position such that a fluid tip is above the housing.

13. The oral irrigator of claim 12, wherein the two opposing walls are planar.

14. The oral irrigator of claim 12, wherein the two opposing walls are parallel.

15. The oral irrigator of claim 12, wherein the handle extends from a first end to a second end in a generally elongate form along the longitudinal axis and the two opposing walls defining the slot extend at an angle with respect to the longitudinal axis.

16. The oral irrigator of claim 12, wherein the slot is positioned such that a length of the slot is centered between a length of the handle from a base end to a top end and the fluid tip attaches to the handle at the top end.

\* \* \* \* \*